United States Patent
Muraoka et al.

(10) Patent No.: US 6,300,500 B1
(45) Date of Patent: Oct. 9, 2001

(54) PREPARATION OF PYRIDONE DERIVATIVES USING PHTHALIMIDO CONTAINING STARTING MATERIAL

(75) Inventors: Masami Muraoka, Toyonaka; Koji Morishita, Nishinomiya; Nagisa Aida, Hokkaido; Masashi Tanaka, Takaishi; Masatoshi Yuri, Nishinomiya; Naohito Ohashi, Takatsuki, all of (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 40 days.

(21) Appl. No.: 09/623,030

(22) PCT Filed: Feb. 17, 1999

(86) PCT No.: PCT/JP99/00718

§ 371 Date: Aug. 25, 2000

§ 102(e) Date: Aug. 25, 2000

(87) PCT Pub. No.: WO99/43659

PCT Pub. Date: Sep. 2, 1999

(30) Foreign Application Priority Data

Feb. 25, 1998 (JP) .................................. 10-062346
Mar. 19, 1998 (JP) .................................. 10-092567

(51) Int. Cl.[7] ........................ C07D 471/04; C07D 211/02
(52) U.S. Cl. .......................................... 546/122; 546/249
(58) Field of Search .................... 546/122, 249

(56) References Cited

U.S. PATENT DOCUMENTS

| | | | |
|---|---|---|---|
| 5,223,513 | 6/1993 | Meguro et al. | 514/312 |
| 5,256,782 | 10/1993 | Meguro et al. | 546/114 |
| 5,362,742 | 11/1994 | Meguro et al. | 514/312 |
| 5,565,472 | 10/1996 | Hamanaka | 514/312 |

FOREIGN PATENT DOCUMENTS

| | | |
|---|---|---|
| 0418071 A2 | 3/1991 | (EP) . |
| 0842933 A1 | 5/1998 | (EP) . |
| 0947515 A1 | 10/1999 | (EP) . |
| 0987254 A1 | 3/2000 | (EP) . |
| 120243 | 5/1991 | (JP) . |
| 503712 | 4/1995 | (JP) . |
| 948780 | 2/1997 | (JP) . |
| 212288 | 8/1998 | (JP) . |
| 510512 | 10/1998 | (JP) . |
| WO 9219614 A1 | 11/1992 | (WO) . |
| WO 9610559 A1 | 4/1996 | (WO) . |
| 854153 | 12/1998 | (WO) . |

OTHER PUBLICATIONS

March, Advanced Organic Chemistry, Third Edition, pp. 983–984 (1985).
Shantare et al., Chemistry of Heterocyclic Compounds, vol. 33, No. 2, pp. 208–215 (1997).
Shartare et al., Chemistry of Hererocyclic Compounds, vol. 34, No. 3, pp. 351–358 (1998).
Gudriniece et al., khim. Geterotsikl. Sodin., No. 2, pp. 271–272 (1995).

Primary Examiner—Bernard Dentz

(57) ABSTRACT

A process for preparing a pyridone derivative (4), which comprises reacting the compound (1) with a hypochlorite or a hypobromite or with lead tetraacetate to give the compound (2), and reacting the compound (2) with the compound (3). Said process is preferably especially from the standpoint of safety.

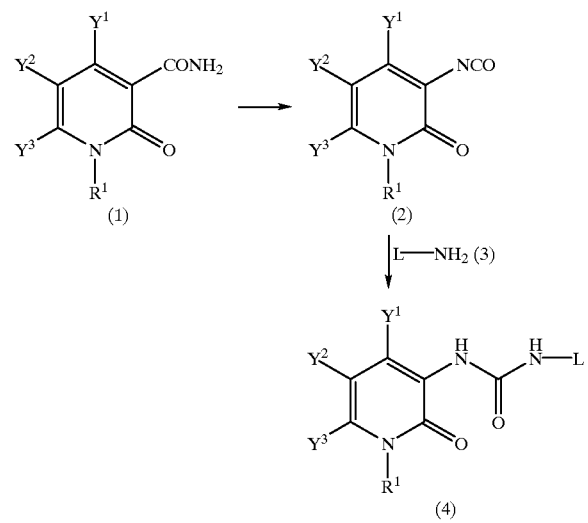

wherein $R^1$ is hydrogen, alkyl, substituted alkyl, etc.; $Y^1$ is hydrogen, alky, substituted alky, etc.; $Y^2$ and $Y^3$ are indenpently hydrogen, halogen, etc.; and L is alkyl, substituted alky, etc.

5 Claims, No Drawings

PREPARATION OF PYRIDONE DERIVATIVES USING PHTHALIMIDO CONTAINING STARTING MATERIAL

This application is the national phase under 35 U.S.C. § 371 of PCT International Application No. PCT/JP99/00718 which has an International filing date of Feb. 17, 1999, which designated the United States of America.

TECHNICAL FIELD

The present invention relates to a pyridone derivative or a salt thereof, which exhibits acyl-CoA: cholesterol acyl transferase (ACAT) inhibitory activity, and is useful as an agent for treatment of hyperlipidemia and atherosclerosis, and a process for preparing the same.

PRIOR ART

Cerebral vessel disorders such as stroke, and myocardial infarction, which rank in high in causes of death in developed countries, break out with being accompanied by atherosclerosis as basal disease. From the results of epidemiology research, it is pointed out that hypercholesterolemia is one of risk factors for atherosclerosis, and there are mainly used anti-hyperlipidemic agents, which can reduce cholesterol level in blood, in the prophylaxis or treatment thereof. However, there is no sufficiently effective agent in terms of the efficacy thereof. Recently, it is observed that cells derived from macrophage accumulate cholesterol ester droplet within the cells and become foam cells in atherosclerotic lesions, and it is clarified that these foam cells deeply participate in the developments of atherosclerotic lesions (Arteriosclerosis, 10, 164–177, 1990). In addition, it is reported that ACAT activity is increased and cholesterol esters are accumulated in the vascular wall of atherosclerotic lesions (Biochem. Biophys. Acta, 617, 458–471, 1980). Therefore, an inhibitor of ACAT, which catalyses cholesterol esterification, is expected to suppress the formation or the development of atherosclerotic lesions as a result of the inhibition of foam cell formation and of cholesterol ester accumulation in lesions.

On the other hand, cholesterol in food is absorbed in the free form at intestinal epidermal cells, and then released in the form of chylomicron esterified by ACAT into the blood. Therefore, an inhibitor of ACAT is expected to reduce the cholesterol level in the blood by the inhibition of absorption of cholesterol in food at the intestine and of reabsorption of cholesterol released into the intestine (J. Lipid. Research, 34, 279–294, 1993).

JP-A-3-181465, JP-A-3-223254 and JP-A-6-501025 disclose some kinds of quinoline derivatives having an ACAT inhibitory activity, and JP-A-5-32666 discloses some kinds of thienopyridine derivatives having an ACAT inhibitory activity, and further JP-A-9-48780 discloses some kinds of naphthyridine derivatives having an ACAT inhibitory activity.

These patent publications disclose processes for preparation of these compounds, for example, in the above JP-A-9-48780, an ureidonaphthyridine derivative which is a pyridone derivative and its intermediate, an amino derivative are prepared by the following process.

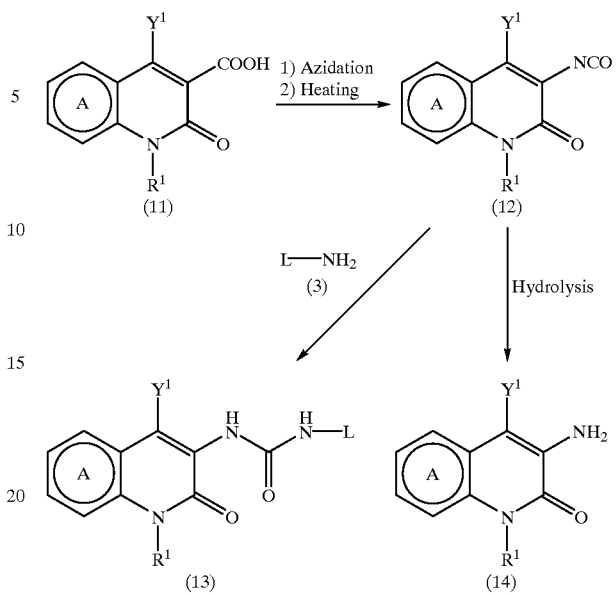

wherein Ring A is a substituted or unsubstituted pyridine ring; $R^1$ is a hydrogen atom, an alkyl group, a substituted alkyl group, a cycloalkyl group, or a substituted cycloalkyl group; $Y^1$ is an alkyl group, a substituted. alkyl group, a cycloalkyl group, a substituted cycloalkyl group, an aromatic group, or a substituted aromatic group; L is an alkyl group, a substituted alkyl group, an alkenyl group, a substituted alkenyl group, a cycloalkyl group, a substituted cycloalkyl group, an aromatic group, or a substituted aromatic group.

That is, a carboxy derivative of the formula (11) is azidated with an azidating agent, and subsequently heated to convert into an isocyanate derivative of the formula (12), which is further reacted with an amine derivative of the formula (3) to give an ureido derivative of the formula (13), or alternatively the isocyanate derivative (12) is hydrolyzed to give an amine derivative of the formula (14).

DISCLOSURE OF INVENTION

However, the present inventors have found that the azidating agents used in the above process and the compounds prepared by azidating the carboxyl derivative of the formula (II) have a risk of explosion and therefore, they are not suitable for large-scale production with respect to safety.

An object of the present invention is to provide a process for preparing pyridone derivatives and aminopyridone derivatives, especially a preferable process thereof with respect to safety, and to provide a novel pyridone derivative.

The present inventors have intensively studied in order to solve the above problems, and have found that pyridone derivatives and aminopyridone derivatives can safely be prepared by the following Processes [1] to [37], and further have found that novel pyridone derivatives of the following [38] to [54] exhibit a potent ACAT inhibitory activity, and then have accomplished the present invention.

That is, the gist of the present invention is as follows.

[1] A process for preparing a pyridone derivative of the formula (4):

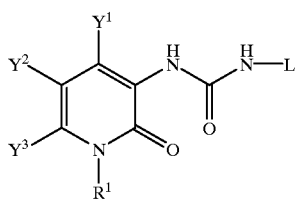

(4)

wherein $R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; $Y^1$ is a hydrogen atom, an alkyl group, a substituted alkyl group, a cycloalkyl group, a substituted cycloalkyl group, an aromatic group, or a substituted aromatic group; $Y^2$ and $Y^3$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, a substituted aromatic group, or $Y^2$ and $Y^3$ may combine each other together with the carbon atoms to which they bond, and form a substituted or unsubstituted pyridine ring; and L is an alkyl group, a substituted alkyl group, an alkenyl group, a substituted alkenyl group, a cycloalkyl group, a substituted cycloalkyl group, an aromatic group, or a substituted aromatic group, which comprises reacting a compound of the formula (1):

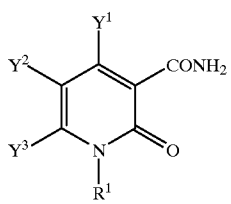

(1)

wherein $R^1$, $Y^1$, $Y^2$ and $Y^3$ are as defined above, with a hypochlorite or a hypobromite or with lead tetraacetate to give a compound of the formula (2):

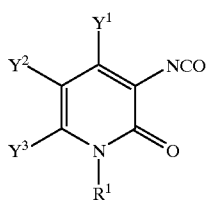

(2)

wherein $R^1$, $Y^1$, $Y^2$ and $Y^3$ are as defined above, followed by reacting the compound (2) with a compound of the formula (3):

   (3)

wherein L is as defined above.

[2] The process according to the above [1], wherein a sodium hypochlorite or a sodium hypobromite is used in the reaction from the compound (1) to the compound (2).

[3] The process according to the above [1], wherein lead tetraacetate is used in the reaction from the compound (1) to the compound (2).

[4] The process for preparing the pyridone derivative according to any one of the above [1] to [3], wherein $Y^2$ and $Y^3$ combine each other together with the carbon atoms to which they bond, and form a substituted or unsubstituted pyridine ring, and said pyridine ring is a group of the following formula (a), (b) or (c):

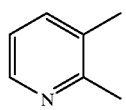

(a)

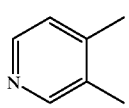

(b)

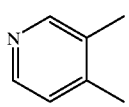

(c)

[5] The process for preparing the pyridone derivative according to any one of the above [1] to [3], wherein $Y^2$ and $Y^3$ combine each other together with the carbon atoms to which they bond, and form a substituted or unsubstituted pyridine ring, and said pyridine ring is a group of the following formula (a):

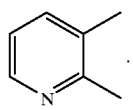

(a)

[6] The process for preparing the pyridone derivative according to the above [1] or [5], wherein $Y^1$ and L are a substituted aromatic group, and $R^1$ is a substituted or unsubstituted alkyl group.

[7] The process for preparing the pyridone derivative according to the above [6], wherein $Y^1$ is a 3-methoxyphenyl group, L is a 2,6-diisopropylphenyl group, and $R^1$ is a butyl group.

[8] A process for preparing a pyridone derivative of the formula (4):

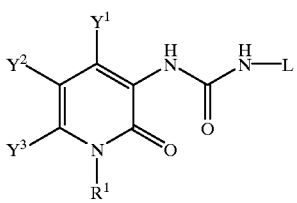

(4)

wherein $R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; $Y^1$ is a hydrogen atom, an alkyl group, a substituted alkyl group, a cycloalkyl group, a substituted cycloalkyl group, an aromatic group, or a substituted aromatic group; $Y^2$ and $Y^3$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, a substituted aromatic group, or $Y^2$ and $Y^3$ may combine each other together with the carbon atoms to which they bond, and form a substituted or unsubstituted pyridine ring; and L is an alkyl group, a substituted alkyl group, an alkenyl group, a substituted alkenyl group, a cycloalkyl group, a substituted cycloalkyl group, an aromatic group, or a substituted aromatic group, which comprises reacting a compound of the formula (5):

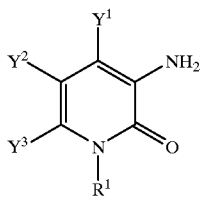

(5)

wherein $R^1$, $Y^1$, $Y^2$ and $Y^3$ are as defined above, with a compound of the formula (6):

XCO$_2$R$^2$ (6)

wherein $R^2$ is a substituted or unsubstituted lower alkyl group, or a substituted or unsubstituted phenyl group; and X is a chorine atom or a bromine atom, to give a compound of the formula (7):

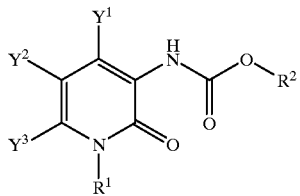

(7)

wherein $R^1$, $R^2$, $Y^1$, $Y^2$ and $Y^3$ are as defined above, followed by reacting the compound (7) with a compound of the formula (3):

L—NH$_2$ (3)

wherein L is as defined above.

[9] The process for preparing the pyridone derivative according to the above [8], wherein $Y^2$ and $Y^3$ combine each other together with the carbon atoms to which they bond, and form a substituted or unsubstituted pyridine ring, and said pyridine ring is a group of the following formula (a), (b) or (c):

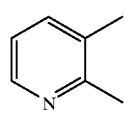

(a)

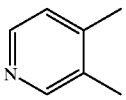

(b)

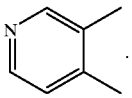

(c)

[10] The process for preparing the pyridone derivative according to the above [8], wherein $Y^2$ and $Y^3$ combine each other together with the carbon atoms to which they bond, and form a substituted or unsubstituted pyridine ring, and said pyridine ring is a group of the following formula (a):

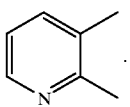

(a)

[11] The process for preparing the pyridone derivative according to the above [9] or [10], wherein $Y^1$ and L are a substituted aromatic group, and $R^1$ is a substituted or unsubstituted alkyl group.

[12] The process for preparing the pyridone derivative according to the above [11], wherein $Y^1$ is a 3-methoxyphenyl group, L is a 2,6-diisopropylphenyl group, and $R^1$ is a butyl group.

[13] A process for preparing an aminopyridone derivative of the formula (5):

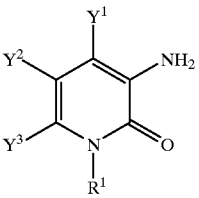

(5)

wherein $R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; $Y^1$ is a hydrogen atom, an alkyl group, a substituted alkyl group, a cycloalkyl group, a substituted cycloalkyl group, an aromatic group, or a substituted aromatic group; and $Y^2$ and $Y^3$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, a substituted aromatic group, or $Y^2$ and $Y^1$ may combine each other together with the carbon atoms to which they bond, and form a substituted or unsubstituted pyridine ring, which comprises reacting a compound of the formula (1):

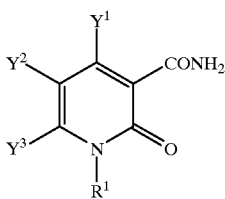
(1)

wherein $R^1$, $Y^1$, $Y^2$ and $Y^3$ are as defined above, with a hypochlorite or a hypobromite or with lead tetraacetate to give a compound of the formula (2):

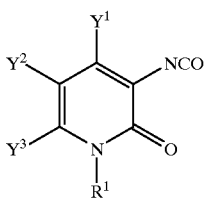
(2)

wherein $R^1$, $Y^1$, $Y^2$ and $Y^3$ are as defined above, followed by subjecting the compound (2) to hydrolysis.

[14] The process for preparing the aminopyridone derivative according to the above [13], wherein $Y^2$ and $Y^3$ combine each other together with the carbon atoms to which they bond, and form a substituted or unsubstituted pyridine ring, and said pyridine ring is a group of the following formula (a), (b) or (c):

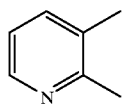
(a)

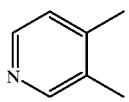
(b)

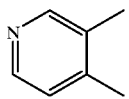
(c)

[15] The process for preparing the aminopyridone derivative according to the above [13], wherein $Y^2$ and $Y^3$ combine each other together with the carbon atoms to which they bond, and form a substituted or unsubstituted pyridine ring, and said pyridine ring is a group of the following formula (a):

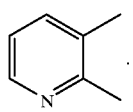
(a)

[16] The process for preparing the aminopyridone derivative according to the above [14] or [15], wherein $Y^1$ is a substituted aromatic group, and $R^1$ is a substituted or unsubstituted alkyl group.

[17] The process for preparing the aminopyridone derivative according to the above [16], wherein $Y^1$ is a 3-methoxyphenyl group, and $R^1$ is a butyl group.

[18] A process for preparing an aminopyridone derivative of the formula (5):

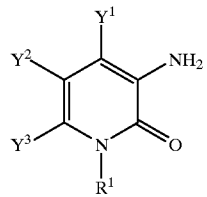
(5)

wherein $R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; $Y^1$ is a hydrogen atom, an alkyl group, a substituted alkyl group, a cycloalkyl group, a substituted cycloalkyl group, an aromatic group, or a substituted aromatic group; and $Y^2$ and $Y^3$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, a substituted aromatic group, or $Y^2$ and $Y^1$ may combine each other together with the carbon atoms to which they bond, and form a substituted or unsubstituted pyridine ring, which comprises heating a compound of the formula (8):

(8)

wherein $R^1$, $Y^1$, $Y^2$ and $Y^3$ are as defined above, and Ring B is a substituted or unsubstituted benzene ring, in the presence of a base, to give a compound of the formula (9):

(9)

wherein $R^1$, $Y^1$, $Y^2$, $Y^3$ and Ring B are as defined above, followed by removing the protecting phthaloyl group thereof.

[19] The process for preparing the aminopyridone derivative according to the above [18], wherein $Y^2$ and $Y^3$ combine each other together with the carbon atoms to which they bond, and form a substituted or unsubstituted pyridine ring, and said pyridine ring is a group of the following formula (a), (b) or (c):

(a)
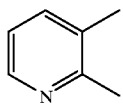

(b)
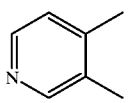

(c)
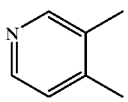

[20] The process for preparing the aminopyridone derivative according to the above [18], wherein $Y^2$ and $Y^3$ combine each other together with the carbon atoms to which they bond, and form a substituted or unsubstituted pyridine ring, and said pyridine ring is a group of the following formula (a):

(a)
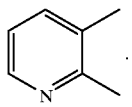

[21] The process for preparing the aminopyridone derivative according to the above [19] or [20], wherein $Y^1$ is a substituted aromatic group, and $R^1$ is a substituted or unsubstituted alkyl group.
[22] The process for preparing the aminopyridone derivative according to the above [21], wherein $Y^1$ is a 3-methoxyphenyl group, and $R^1$ is a butyl group.
[23] A process for preparing an aminopyridone derivative of the formula (5):

(5)
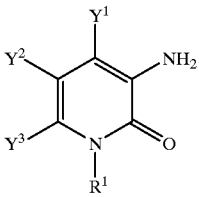

wherein $R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; $Y^1$ is a hydrogen atom, an alkyl group, a substituted alkyl group, a cycloalkyl group, a substituted cycloalkyl group, an aromatic group, or a substituted aromatic group; and $Y^2$ and $Y^3$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, a substituted aromatic group, or $Y^2$ and $Y^3$ may combine each other together with the carbon atoms to which they bond, and form a substituted or unsubstituted pyridine ring, which comprises reacting a compound of the formula (1):

(1)
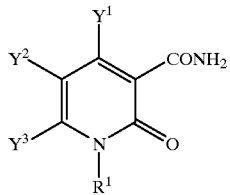

wherein $R^1$, $Y^1$, $Y^2$ and $Y^3$ are as defined above, with a hypochlorite or a hypobromite.

[24] The process for preparing the aminopyridone derivative according to the above [23], wherein $Y^2$ and $Y^3$ combine each other together with the carbon atoms to which they bond, and form a substituted or unsubstituted pyridine ring, and said pyridine ring is a group of the following formula (a), (b) or (c):

(a)
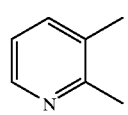

(b)
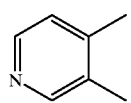

(c)
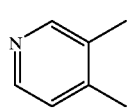

[25] The process for preparing the aminopyridone derivative according to the above [23], wherein $Y^2$ and $Y^3$ combine each other together with the carbon atoms to which they bond, and form a substituted or unsubstituted pyridine ring, and said pyridine ring is a group of the following formula (a):

(a)
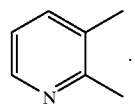

[26] The process for preparing the aminopyridone derivative according to the above [24] or [25], wherein $Y^1$ is a substituted aromatic group, and $R^1$ is a substituted or unsubstituted alkyl group.
[27] The process for preparing the aminopyridone derivative according to the above [26], wherein $Y^1$ is a 3-methoxyphenyl group, and $R^1$ is a butyl group.

[28] A process for preparing a pyridone derivative of the formula (4):

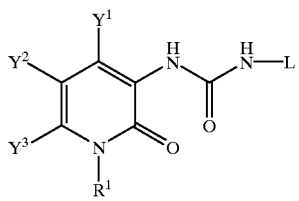
(4)

wherein R¹ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; Y¹ is a hydrogen atom, an alkyl group, a substituted alkyl group, a cycloalkyl group, a substituted cycloalkyl group, an aromatic group, or a substituted aromatic group; Y² and Y³ are independently a hydrogen atom, a halogen atom, a hydroxy group, a cyano group, a trifluoromethyl group, a nitro group, an amino group, a mono-lower alkamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, a substituted aromatic group, or Y² and Y³ may combine each other together with the carbon atoms to which they bond, and form a substituted or unsubstituted pyridine ring; and L is an alkyl group, a substituted alkyl group, an alkenyl group, a substituted alkenyl group, a cycloalkyl group, a substituted cycloalkyl group, an aromatic group, or a substituted aromatic group, which comprises reacting a compound of the formula (3):

(3)

wherein L is as defined above, with a compound of the formula (6):

(6)

wherein R² is a substituted or unsubstituted lower alkyl group, or a substituted or unsubstituted phenyl group; and X is a chlorine atom or a bromine atom, to give a compound of the formula (32)

(32)

wherein R² and L are as defined above, following by reacting the compound (32) with a compound of the formula (5):

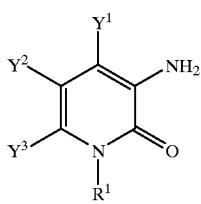
(5)

wherein R¹, Y¹, Y² and Y³ are as defined above.

[29] The process for preparing the pyridone derivative according to the above [28], wherein Y² and Y³ combine each other together with the carbon atoms to which they bond, and form a substituted or unsubstituted pyridine ring, and said pyridine ring is a group of the following formula (a), (b) or (c):

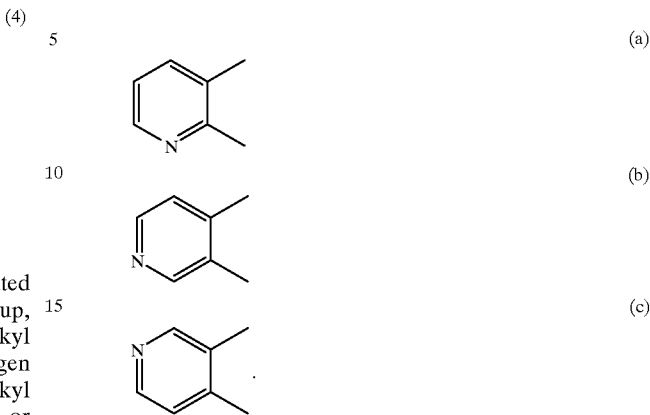

(a)

(b)

(c)

[30] The process for preparing the pyridone derivative according to the above [28], wherein Y² and Y³ combine each other together with the carbon atoms to which they bond, and form a substituted or unsubstituted pyridine ring, and said pyridine ring is a group of the following formula (a):

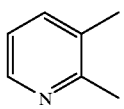
(a)

[31] The process for preparing the pyridone derivative according to the above [29] or [30], wherein Y¹ and L are a substituted aromatic group, and R¹ is a substituted or unsubstituted alkyl group.

[32] The process for preparing the pyridone derivative according to the above [31], wherein Y¹ is a 3-methoxyphenyl group, L is a 2,6-diisopropylphenyl group, and R¹ is a butyl group.

[33] A process for preparing a pyridone derivative of the formula (4):

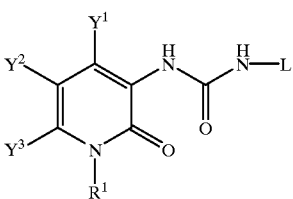
(4)

wherein R¹ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; Y¹ is a hydrogen atom, an alkyl group, a substituted alkyl group, a cycloalkyl group, a substituted cycloalkyl group, an aromatic group, or a substituted aromatic group; Y² and Y³ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, a substituted aromatic group, or $Y^2$ and $Y^3$ may combine each other together with the carbon atoms to which they bond, and form a substituted or unsubstituted pyridine ring; and L is an alkyl group, a substituted alkyl group, an alkenyl group, a substituted alkenyl group, a cycloalkyl group, a substituted cycloalkyl group, an aromatic group, or a substituted aromatic group, which comprises reacting a compound of the formula (5):

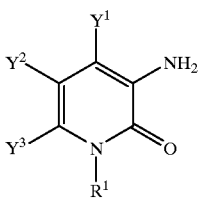

(5)

wherein $R^1$, $Y^1$, $Y^2$ and $Y^3$ are as defined above, with a compound of the formula (6):

L—NCO (31)

wherein L is as defined above.

[34] The process for preparing the pyridone derivative according to the above [33], wherein $Y^2$ and $Y^3$ combine each other together with the carbon atoms to which they bond, and form a substituted or unsubstituted pyridine ring, and said pyridine ring is a group of the following formula (a), (b) or (c):

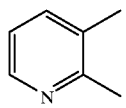

(a)

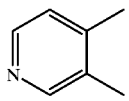

(b)

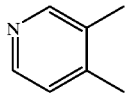

(c)

[35] A process for preparing the pyridone derivative according to the above [33], wherein $Y^2$ and $Y^3$ combine each other together with the carbon atoms to which they bond, and form a substituted or unsubstituted pyridine ring, and said pyridine ring is a group of the following formula (a):

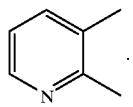

(a)

[36] The process for preparing the pyridone derivative according to the above [34] or [35], wherein $Y^1$ and L are a substituted aromatic group, and $R^1$ is a substituted or unsubstituted alkyl group.

[37] The process for preparing the pyridone derivative according to the above [36], wherein $Y^1$ is a 3-methoxyphenyl group, L is a 2,6-diisopropylphenyl group, and $R^1$ is a butyl group.

[38] A pyridone derivative of the formula (10):

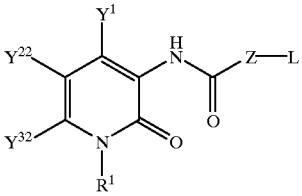

(10)

wherein L is an alkyl group, a substituted alkyl group, an alkenyl group, a substituted alkenyl group, a cycloalkyl group, a substituted cycloalkyl group, an aromatic group, or a substituted aromatic group;

Z is a direct bond or —NH—;

$R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group, provided that when Z is a direct bond, then $R^1$ is not a hydrogen atom;

$Y^1$ is a hydrogen atom, an alkyl group, a substituted alkyl group, a cycloalkyl group, a substituted cycloalkyl group, an aromatic group, or a substituted aromatic group;

$Y^{22}$ and $Y^{32}$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted alkyl group, a cycloalkyl group, a substituted cycloalkyl group, an aromatic group, or a substituted aromatic group, or a salt thereof.

[39] The pyridone derivative according to the above [38], or a salt thereof, wherein Z is —NH—.

[40] The pyridone derivative according to the above [39], or a salt thereof, wherein $Y^1$ is an alkyl group, a substituted alkyl group, a cycloalkyl group, a substituted cycloalkyl group, an aromatic group, or a substituted aromatic group.

[41] The pyridone derivative according to the above [39] or [40], or a salt thereof, wherein one of $Y^1$, $Y^2$ and $Y^3$ is an aromatic group or a substituted aromatic group.

[42] The pyridone derivative according to the above [39], [40] or [41], or a salt thereof, wherein L is an aromatic group or a substituted aromatic group.

[43] The pyridone derivative according to the above [42], or a salt thereof, wherein one of $Y^1$, $Y^2$ and $Y^3$ is a substituted phenyl group, and one of the substituents thereof is a group of the formula: —$M^1$—E—Q ($M^1$ is a direct bond, an oxygen atom, a sulfur atom or a group of the formula: —$NR^3$— ($R^3$ is a hydrogen atom or a lower alkyl group), E is a divalent aliphatic hydrocarbon group having 1 to 15 carbon atoms and optionally containing an unsaturated bond, or a phenylene group, Q is a hydrogen atom, a hydroxy group, a carboxyl group, a lower alkoxycarbonyl group, a benzyloxycarbonyl group, a halogen atom, a cyano group, a benzyloxy group, a lower alkoxy group, a lower alkanoyloxy group, a lower alkylthio group, a lower alkylsulfinyl group, a lower alkylsulfonyl group, a benzenesulfonyloxy group being optionally substituted by an alkyl group, a lower alkanoylamino group, a lower alkoxycarbonylamino group, a lower alkylsulfonamido group, a phthalimido group, a cycloalkyl group, an aryl group, a substituted aryl group, a heteroaryl group, a substituted heteroaryl group, a group of the formula: —NR$^4$R$^5$ (R$^4$ and R$^5$ are independently a hydrogen atom, a lower alkyl group, a di-lower alkylamino-substituted lower alkyl group, a lower alkoxy-substituted lower alkyl group, a cycloalkyl group, a lower alkoxycarbonyl group, a heteroarylmethyl group, or an aralkyl group, or R$^4$ and R$^5$ may combine each other together with the nitrogen atom to which they bond, and form a saturated cyclic amino group having 4 to 8 carbon atoms as ones forming the said ring, and optionally having one —NR$^{20}$— (R$^{20}$ is a hydrogen atom, a lower alkyl group, a phenyl group, a lower alkoxycarbonyl group, or a benzyl group) or one oxygen atom in the cycle thereof), or a group of the formula: —C(=O)NR$^4$R$^5$ (R$^4$ and R$^5$ are as defined above)).

[44] The pyridone derivative according to the above [43], or a salt thereof, wherein Y$^1$ is a substituted phenyl group.

[45] The pyridone derivative according to the above [44], or a salt thereof, wherein M$^1$ is an oxygen atom.

[46] The pyridone derivative according to the above [43], [44] or [45], or a salt thereof, wherein Q is a hydrogen atom, a hydroxy group, a carboxyl group, a lower alkoxycarbonyl group, a benzyloxycarbonyl group, a benzyloxy group, a lower alkoxy group, a lower alkanoyloxy group, a lower alkanoylamino group, a heteroaryl group, a substituted heteroaryl group, or a group of the formula: —NR$^4$R$^5$.

[47] The pyridone derivative according to the above [46], or a salt thereof, wherein E is an alkylene group having 1 to 4 carbon atoms, and Q is a substituted or unsubstituted pyridyl group, a 1,2,4-triazol-1-yl group, or a group of the formula: —NR$^4$R$^5$.

[48] The pyridone derivative according to the above [43] or [44], or a salt thereof, wherein M$^1$ is a direct bond.

[49] The pyridone derivative according to the above [48], or a salt thereof, wherein Q is a hydrogen atom, a hydroxy group, a carboxyl group, a lower alkoxycarbonyl group, a benzyloxycarbonyl group, a benzyloxy group, a lower alkoxy group, a lower alkanoyloxy group, a lower alkanoylamino group, a heteroaryl group, a substituted heteroaryl group, or a group of the formula: —NR$^4$R$^5$.

[50] The pyridone derivative according to the above [48] or [49], or a salt thereof, wherein —E— is a group of the formula:

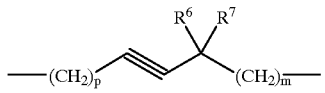

(wherein R$^6$ and R$^7$ are independently a hydrogen atom, a methyl group, an ethyl group, or a propyl group, or R$^6$ and R$^7$ may combine each other to form a 3- to 7-membered cycloalkane ring, m is an integer of 0 to 6, and p is an integer of 0 to 6).

[51] The pyridone derivative according to the above [50], or a salt thereof, wherein p is 0.

[52] The pyridone derivative according to the above [51], or a salt thereof, wherein R$^6$ and R$^7$ are both hydrogen atoms, and m is 0 or 1.

[53] The pyridone derivative according to the above [47] or [52], or a salt thereof, wherein R$^1$ is an alkyl group, a substituted alkyl group, or a hydrogen atom.

[54] The pyridone derivative according to the above [53], or a salt thereof, wherein Y$^{22}$ and Y$^{32}$ are both hydrogen atoms.

[55] A pharmaceutical composition containing a pyridone derivative as set forth in any one of the above [38] to [54], or a salt thereof.

[56] An acyl-CoA: cholesterol acyl transferase (ACAT) inhibitor, which contains as an active ingredient a pyridone derivative as set forth in any one of the above [38] to [54], or a salt thereof.

[57] An agent for treatment of hyperlipidemia or atherosclerosis, which contains as an active ingredient a pyridone derivative as set forth in any one of the above [38] to [54], or a salt thereof.

[58] A method for inhibiting acyl-CoA: cholesterol acyl transferase (ACAT), which comprises administering an effective amount of a pyridone derivative as set forth in any one of the above [38] to [54], or a salt thereof, to a patient in need thereof.

[59] A method for treatment of hyperlipidemia or atherosclerosis, which comprises administering an effective amount of a pyridone derivative as set forth in any one of the above [38] to [54], or a salt thereof, to a patient in need thereof.

[60] Use of a pyridone derivative as set forth in any one of the above [38] to [54], or a salt thereof, in preparation of a pharmaceutical composition for inhibiting acyl-CoA: cholesterol acyl transferase (ACAT).

[61] Use of a pyridone derivative as set forth in any one of the above [38] to [54], or a salt thereof, in preparation of an agent for treatment of hyperlipidemia or atherosclerosis.

Each group in the present invention is explained below.

Incidentally, throughout the description, when the present compounds have substituents such as hydroxy group, amino group, alkylamino group, carboxyl group, etc., then these groups may optionally be protected when the present methods are carried out. The protecting groups for hydroxy group, amino group, alkylamino group, carboxyl group, etc., may be conventional protecting groups which are used in the field of the organic chemistry, for example, as described in PROTECTIVE GROUPS IN ORGANIC SYNTHESIS, 2nd ed., John Wiley & Sons, Inc.; New York. For example, the protected hydroxy group may be benzyloxy group and 2-methoxyethoxymethoxy group, and the protected amino group may be benzylamino group and acetylamino group, and the protected alkylamino group may be N-benzyl-N-alkylamino group and N-acetyl-N-alkylamino group, and the protected carboxyl group may be tert-butoxycarbonyl group and methoxymethoxycarbonyl group.

Ring B is a substituted or unsubstituted benzene ring, and the substituted benzene ring has one or more substituents which are the same or different.

The substituent of the benzene ring may be, for example, a lower alkyl group, a halogen atom, a cyano group, a trifluoromethyl group, a nitro group, a protected amino group, a protected lower alkylamino group, a di-lower alkylamino group, a lower alkoxy group, a lower alkylthio group, a lower alkylsulfinyl group, a lower alkylsulfonyl group, etc.

The pyridine ring formed by combining Y$^2$ and Y$^3$ together with the carbon atoms to which they bond is a substituted or unsubstituted pyridine ring, and the nitrogen atom thereof may be located at any position except for the fused positions of the fused ring, and the substituted pyridine ring has one or more substituents which are the same or different.

Besides, the substituent of the pyridine ring formed by combining Y$^2$ and Y$^3$ together with the carbon atoms to which they bond may be, for example, a lower alkyl group, a halogen atom, a cyano group, a trifluoromethyl group, a nitro group, a protected amino group, a protected lower alkylamino group, a di-lower alkylamino group, a lower alkoxy group, a lower alkylthio group, a lower aikylsulfinyl group, a lower alkylsulfonyl group, etc.

The alkyl group or the alkyl moiety of the substituted alkyl group for $Y^1$, $Y^2$, $Y^3$ and $R^1$ includes, for example, a straight chain or branched chain alkyl group having 1 to 15 carbon atoms, such as methyl, ethyl, propyl, 2-propyl, butyl, 2-butyl, 2-methylpropyl, 1,1-dimethylethyl, pentyl, 3-pentyl, 3-methylbutyl, hexyl, 3-hexyl, 4-methylpentyl, 4-heptyl, octyl, 4-octyl, decyl, etc.

The alkenyl group or the alkenyl moiety of the substituted alkenyl group for $R^1$ includes, for example, a straight chain or branched chain alkenyl group having 2 to 15 carbon atoms, such as vinyl, allyl, 2-propenyl, 2-methyl-2-propenyl, 2-butenyl, 3-butenyl, 3-methyl-2-butenyl, 4-pentenyl, 3-hexenyl, 3-ethyl-2-pentenyl, 4-ethyl-3-hexenyl, etc.

The alkynyl group or the alkynyl moiety of the substituted alkynyl group for $R^1$ includes, for example, a straight chain or branched chain alkynyl group having 3 to 15 carbon atoms, such as 2-propynyl, 3-butynyl, 4-pentynyl, 3-hexynyl, 5-methyl-2-hexynyl, 6-methyl-4-heptynyl, etc.

The alkyl group or the alkyl moiety of the substituted alkyl group for L includes, for example, a straight chain or branched chain alkyl group having 1 to 20 carbon atoms, such as methyl, ethyl, propyl, 2-propyl, butyl, 2-butyl, 2-methylpropyl, 1,1-dimethylethyl, pentyl, 3-pentyl, hexyl, heptyl, octyl, undecyl, dodecyl, hexadecyl, 2,2-dimethyldodecyl, 2-tetradecyl, n-octadecyl, etc.

The alkenyl group or the alkenyl moiety of the substituted alkenyl group for L includes, for example, a straight chain or branched chain alkenyl group having 3 to 20 carbon atoms and having 1 to 2 double bonds, such as 2-propenyl, 2-butenyl, 3-methyl-2-butenyl, 3-pentenyl, 2-octenyl, 5-nonenyl, 4-undecenyl, 5-heptadecenyl, 3-octadecenyl, 9-octadecenyl, 2,2-dimethyl-9-octadecenyl, 9,12-octadecadienyl, etc.

The cycloalkyl group or the cycloalkyl moiety of the substituted cycloalkyl group includes, for example, a cycloalkyl group having 3 to 8 carbon atoms, such as cyclopropyl, cyclobutyl, cyclopentyl, cyclohexyl, cycloheptyl, cyclooctyl, etc.

The aromatic group includes, for example, an aryl group and a heteroaryl group.

The aryl group includes, for example, an aryl group having carbon atoms of not more than 10, such as phenyl group, naphthyl group, etc.

The heteroaryl group includes, for example, a 5- to 6-membered heteromonocyclic group having 1 to 2 nitrogen atoms, a 5- to 6-membered heteromonocyclic group having 1 to 2 nitrogen atoms and one oxygen atom or one sulfur atom, a 5-membered heteromonocyclic group having one oxygen atom or one sulfur atom, a heterobicyclic group formed by fusing a 6-membered ring and a 5- or 6-membered ring and having 1 to 4 nitrogen atoms, such as 2-pyridyl, 3-pyridyl, 4-pyridyl, 2-thienyl, 3-thienyl, 3-oxadiazolyl, 1-imidazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, 8-purinyl, etc.

The substituted aromatic group has one or more substituents which are the same or different, and the substituents are, for example, a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, a lower alkylsulfonamido group, or a group of the formula: —$M^1$—E—Q ($M^1$ is a direct bond, an oxygen atom, a sulfur atom, or a group of the formula: —$NR^3$— ($R^3$ is a hydrogen atom or a lower alkyl group), E is a divalent aliphatic hydrocarbon group having 1 to 15 carbon atoms and optionally containing an unsaturated bond, or a phenylene group, Q is a hydrogen atom, a hydroxy group, a carboxyl group, a lower alkoxycarbonyl group, a benzyloxycarbonyl group, a halogen atom, a cyano group, a benzyloxy group, a lower alkoxy group, a lower alkanoyloxy group, a lower alkylthio group, a lower alkylsulfinyl group, a lower alkylsulfonyl group, a benzenesulfonyloxy group being optionally substituted by an alkyl group, a lower alkanoylamino group, a lower alkoxycarbonylamino group, a lower alkylsulfonamido group, a phthalimido group, a cycloalkyl group, an aryl group, a substituted aryl group, a heteroaryl group, a substituted heteroaryl group, a group of the formula: —$NR^4R^5$ ($R^4$ and $R^5$ are independently a hydrogen atom, a lower alkyl group, a di-lower alkylamino-substituted lower alkyl group, a lower alkoxy-substituted lower alkyl group, a cycloalkyl group, a lower alkoxycarbonyl group, a heteroarylmethyl group, or an aralkyl group, or $R^4$ and $R^5$ may combine each other together with the nitrogen atom to which they bond, and form a saturated cyclic amino group having 4 to 8 carbon atoms as ones forming the said ring, and optionally having one —$NR^{20}$— ($R^{20}$ is a hydrogen atom, a lower alkyl group, a phenyl group, a lower alkoxycarbonyl group, or a benzyl group) or one oxygen atom in the cycle thereof), or a group of the formula: —C(=O)$NR^4R^5$ ($R^4$ and $R^5$ are as defined above)).

The divalent aliphatic hydrocarbon group having 1 to 15 carbon atoms and optionally having an unsaturated bond includes, for example, an alkylene chain having 1 to 6 carbon atoms, preferably having 1 to 4 carbon atoms, such as methylene, ethylene, trimethylene, tetramethylene, pentamethylene, hexamethylene, etc., an alkenylene chain such as propenylene, butenylene, etc., an alkynylene chain such as ethynylene, propynylene, butynylene, or as the group —E— an alkynylene chain such as an alkynylene of the following formula:

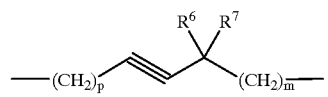

($R^6$ and $R^7$ are independently a hydrogen atom, a methyl group, an ethyl group or a propyl group, or $R^6$ and $R^7$ may combine each other to form a 3- to 7-membered cycloalkane ring, m is an integer of 0 to 6, preferably 0 or 1, and p is an integer of 0 to 6, preferably 0 or 1).

The 3- to 7-membered cycloalkane ring formed by combining $R^6$ and $R^7$ includes, for example, cyclopropane, cyclobutane, cyclopentane, cyclohexane, cycloheptane, etc.

The substituted aryl group for Q has one or more substituents which are the same or different, and the substituents are, for example, a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, or a lower alkylsulfonamido group.

The heteroaryl group or the heteroaryl moiety of the heteroarylmethyl group include, for example, a 5- to 6-membered cyclic group having 1 to 3 nitrogen atoms, a 5-membered cyclic group having one oxygen atom or one sulfur atom, or a bicyclic group formed by fusing a 6-membered ring and a 5- or 6-membered ring, and having 1 to 4 nitrogen atoms, such as 2-pyridyl, 3-pyridyl, 4-pyridyl, 1-pyrrolyl, 1-imidazolyl, 1,2,4-triazol-1-yl, 2-thienyl, 3-thienyl, 2-furyl, 3-furyl, 2-quinolyl, etc.

The substituted heteroaryl group for Q has one or more substituents which are the same or different, and the substituents are, for example, a lower alkyl group, a lower alkoxy group, a halogen atom, etc.

The saturated cyclic amino group formed by $NR^4R^5$ includes, for example, a group represented by the formula:

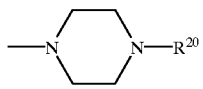

(wherein $R^{20}$ is a hydrogen atom, a lower alkyl group, a phenyl group, a lower alkoxycarbonyl group, or a benzyl group) such as a 4-lower alkyl-1-piperazinyl, 4-phenyl-1-piperazinyl, 4-benzyl-1-piperazinyl, etc., or a monocyclic group such as 1-pyrrolidinyl, 1-piperidinyl, 1-homopiperidinyl, 4-morpholinyl, etc., or a bicyclic group such as 3-azabicyclo[3.2.2]nonane, etc.

The substituted alkyl group, the substituted cycloalkyl group, the substituted alkenyl group, and the substituted alkynyl group have one or more substituents which are the same or different, and the substituents are, for example, a halogen atom, a cyano group, a phenoxy group, a benzyloxy group, a trifluoromethyl group, a hydroxy group, a lower alkoxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a lower alkoxycarbonylamino group, a carboxyl group, a lower alkoxycarbonyl group, a lower alkylthio group, a lower alkylsulfinyl group, a lower alkylsulfonyl group, a lower alkanoylamino group, a lower alkylsulfonamido group, a tri-lower alkylsilyl group, a phthalimido group, a heteroaryl group, a saturated heterocyclic group, or a group of the formula: —$M^2$—E—Q ($M^2$ is an oxygen atom, a sulfur atom, or a group of the formula: —$NR^{21}$ ($R^{21}$ is a hydrogen atom or a lower alkyl group), E and Q are as defined above).

The saturated heterocyclic group includes, for example, a 5- to 8-membered cyclic group having one nitrogen atom, a 6- to 8-membered cyclic group having two nitrogen atoms, and a 6- to 8-membered cyclic group having one nitrogen atom and one oxygen atom, such as 1-piperidinyl, 1-pyrrolidinyl, etc.

The substituted alkyl group includes an alkyl group having 1 to 6 carbon atoms which is substituted by a cycloalkyl group or a substituted cycloalkyl group, or an aralkyl group or a substituted aralkyl group.

The aralkyl group or the substituted aralkyl group includes an alkyl group having 1 to 6 carbon atoms which is substituted by the above-mentioned aryl group or substituted aryl group, for example, benzyl, 1-phenylethyl, 2-phenylethyl, 2-naphthylmethyl, etc.

The phenylene group may be o-phenylene group, m-phenylene group, and p-phenylene group.

The term "lower" in the present invention means that alkyl moiety described with "lower" is a lower alkyl group, and including the cases when the lower alkyl group is a moiety of other substituents, the lower alkyl group may be an alkyl group having 1 to 6 carbon atoms such as methyl, ethyl, propyl, 2-propyl, butyl, pentyl, hexyl, etc.

The halogen atom is fluorine atom, chlorine atom, bromine atom, and iodine atom.

The substituent of the substituted or unsubstituted alkyl group for $R^2$ may be, for example, lower alkoxy group.

The substituent of the substituted or unsubstituted phenyl group for $R^2$ may be, for example, a lower alkyl group, a lower alkoxy group, and a halogen atom.

The compounds of the formula (10) in the above [38] are novel compounds which were found by the present inventors for the first time. In the compounds (10) in the above [38], preferable groups for exhibiting biological activities are exemplified below.

The preferable groups for $Y^1$ are, for example, a phenyl group or pyridyl group which may optionally be substituted. The substituted phenyl group and the substituted pyridyl group have one or more substituents which are the same or different, and the preferable substituents are, for example, a halogen atom (e.g., fluorine atom, chlorine atom, etc.), a cyano group, a trifluoromethyl group, a nitro group, a hydroxy group, methylenedioxy group, a lower alkyl group, a lower alkoxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, a lower alkylsulfonamido group, or a group of the formula: —$M^1$—E—Q ($M^1$, E and Q are as defined above).

The preferable groups for E are, for example, a straight alkylene, alkenylene or alkynylene chain having 1 to 6 carbon atoms, and the more preferable ones are a straight alkylene or alkynylene chain having 1 to 3 carbon atoms. The preferable groups for Q are, for example, a hydroxy group, a halogen atom, a cyano group, a lower alkoxy group, a lower alkanoyloxy group, a lower alkylthio group, a lower alkylsulfinyl group, a lower alkylsulfonyl group, a lower alkanoylamino group, a lower alkylsulfonamido group, a heteroaryl group, or a group of the formula: —$NR^4R^5$ ($R^4$ and $R^5$ are as defined above), and the more preferable ones are a substituted or unsubstituted heteroaryl group (e.g., 2-pyridyl, 3-pyridyl, 2-methylpyridin-3-yl, 4-pyridyl, 1-imidazolyl, 1,2,4-triazol-1-yl, etc.), or a group of the formula: —$NR^4R^5$ ($R^4$ and $R^5$ are as defined above). The preferable group of the formula: —$NR^4R^5$ ($R^4$ and $R^5$ are as defined above) includes, for example, dimethylamino, diethylamino, diisopropylamino, pyrrolidinyl, piperidinyl, morpholinyl, 4-methylpiperazinyl, etc.

The preferable group of the formula: —$M^1$—E—Q includes, for example, 2-pyridylmethoxy, 3-pyridylmethoxy, 4-pyridylmethoxy, (2-methylpyridin-3-yl)methoxy, (2,4-dimethylpyridin-3-yl)methoxy, 2-hydroxyethoxy, 2-acetoxyethoxy, 2-(2-pyridyl)ethoxy, 2-(3-pyridyl)ethoxy, 2-(4-pyridyl)ethoxy, 2-(diethylamino)ethoxy, 2-(dimethylamino)ethoxy, 2-(piperidino)ethoxy, 2-(1-pyrrolidinyl)ethoxy, 2-(morpholino)ethoxy, 2-(1,2,4-triazol-1-yl)ethoxy, 3-hydroxypropoxy, 3-acetoxypropoxy, 3-(2-pyridyl)propoxy, 3-(3-pyridyl)propoxy, 3-(4-pyridyl) propoxy, 3-(diethylamino)propoxy, 3-(dimethylamino) propoxy, 3-(piperidino)propoxy, 3-(1-pyrrolidinyl)propoxy, 3-(morpholino)propoxy, 2-(1,2,4-triazol-1-yl)-propoxy, 3-dimethylamino-1-propynyl, 3-diethylamino-1-pyropynyl, 3-(1-pyrrolidinyl)-1-propynyl, 3-(N-methyl-N-(3-pyridylmethyl)amino)-1-propynyl, 2-(diethylamino) ethylthio, N-methyl-N-(3-pyridylmethyl)amino, 3-(diethylamino)propyl, etc.

The preferable groups for L are a phenyl or heteroaryl group which may optionally be substituted, and the more preferable groups for L are a phenyl or pyridyl group which is substituted by 1 to 3 groups selected from a group consisting of a halogen atom (e.g., a fluorine atom, chlorine atom, etc.), a lower alkyl group, a lower alkoxy group and a lower alkylthio group, or a phenyl group substituted by a lower alkyl group and a group of the formula: —$M^1$—E—Q ($M^1$, E and Q are as defined above). The preferable groups for E are, for example, a straight alkylene, alkenylene or alkynylene chain having 1 to 6 carbon atoms, and the more preferable ones are a straight alkylene or alkynylene chain having 1 to 3 carbon atoms.

The preferable groups for Q are, for example, a hydroxy group, a heteroaryl group, or a group of the formula: —$NR^4R^1$ ($R^1$ and $R^4$ are as defined above), and the more preferable ones are a substituted or unsubstituted heteroaryl group (e.g., 2-pyridyl, 3-pyridyl, 2-methylpyridin-3-yl, 4-pyridyl, 1-imidazolyl, 2-isopropyl-1-imidazolyl, 1-pyrazolyl, 1,2,4-triazol-1-yl, etc.), or a group of the formula: —$NR^4R^5$ ($R^4$ and $R^5$ are as defined above).

The preferable group of the formula: —$NR^4R^5$ ($R^4$ and $R^1$ are as defined above) includes, for example, dimethylamino, diethylamino, diisopropylamino, pyrrolidinyl, piperidinyl, morpholinyl, 4-methylpiperazinyl, etc.

The preferable groups for L are, for example, 2,6-diisopropylphenyl, 2,4,6-trimethylphenyl, 2,4,6-trimethoxyphenyl, 2,4-difluorophenyl, 2,4,6-trifluorophenyl, 2-tert-butyl-5-(morpholinomethyl)phenyl, 2-tert-butyl-5-(2-isopropyl-1-imidazolyl)phenyl, 2-tert-butyl-5-(1-pyrazolyl)phenyl, 2-tert-butyl-5-{N-methyl-N-(2-pyridylmethyl)aminomethyl}phenyl, 2-tert-butyl-5-{N-methyl-N-(3-pyridylmethyl)aminomethyl}phenyl, 2-tert-butyl-5-{N-methyl-N-(4-pyridylmethyl)aminomethyl}phenyl, 2,4-bis(methylthio)pyridin-3-yl, 2-tert-butyl-5-{N-ethyl-N-(3-pyridylmethyl)aminomethyl}phenyl, 2,4-bis(methylthio)-6-methylpyridin-3-yl, etc.

The acid for forming an acid addition salt includes, for example, inorganic acids such as hydrochloric acid, hydrobromic acid, hydroiodic acid, nitric acid, sulfuric acid, etc., or organic acids such as acetic acid, oxalic acid, citric acid, malic acid, tartaric acid, fumaric acid, maleic acid, methanesulfonic acid, etc.

When the compounds of the present invention have an acidic group such as carboxyl group, then the present compounds may be in the form of a salt with an organic base (e.g., diethanolamine salt, ethylenediamine salt, N-methylglucamine salt), a salt with an alkaline earth metal (e.g., calcium salt, magnesium salt), or a salt with an alkali metal (e.g., lithium salt, potassium salt, sodium salt).

The compounds of the present invention may have a stereoisomer due to an asymmetric carbon atom thereof. In such cases, the present compounds also include each isomer or a mixture thereof.

The present compounds and a salt thereof may be in the form of an anhydrous product thereof, or in the form of a solvate thereof such as hydrate.

The compounds of the above-mentioned formula (10) or a salt thereof can be administered either parenterally or orally when used as the above-mentioned drug. The present compounds can be formulated into liquid preparations such as solutions, emulsions, suspensions, etc., and can be administered in the form of an injection, and if necessary, buffering agents, solubilizers and isotonic agents may be added thereto. The present compounds can also be administered rectally in the form of a suppository. The present compounds can also be administered orally in the form of a conventional administration form such as tablets, capsules, syrups, and suspension. These pharmaceutical preparations can be formulated by mixing an active ingredient with conventional carriers or diluents, binding agents or stabilizers by a conventional manner.

The dosage and the frequency of administration of the present compounds may vary according to the conditions, ages, weights of the patients and the administration form, etc., but when the present compound is administered orally, the daily dosage thereof is in the range of 1 to 500 mg for an adult, once a day, or divided into 2–4 dosage units.

Processes [1] to [37] and the processes for preparing the compounds [38] to [54] will be described in detail. In the description of the present processes, the compounds used therein have an reactive group such as amino group, alkylamino group, lower alkylamino group, hydroxy group, carboxyl group as a substituent, then these groups may optionally be protected or deprotected to give the desired compounds.

The protecting groups for amino group, alkylamino group, lower alkylamino group, hydroxy group, carboxyl group, etc., may be conventional protecting groups which are used in the field of the organic chemistry (e.g., the protecting group for hydroxy group may be benzyl group or acetyl group: the protecting group for amino group may be benzyl group, etc.), and these protecting groups may be introduced or removed by a conventional method, as described in PROTECTIVE GROUPS IN ORGANIC SYNTHESIS, 2nd ed., John Wiley & Sons, Inc.; New York.

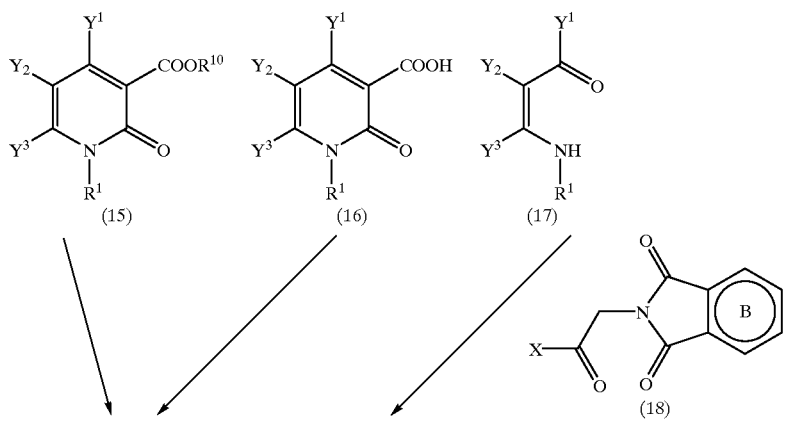

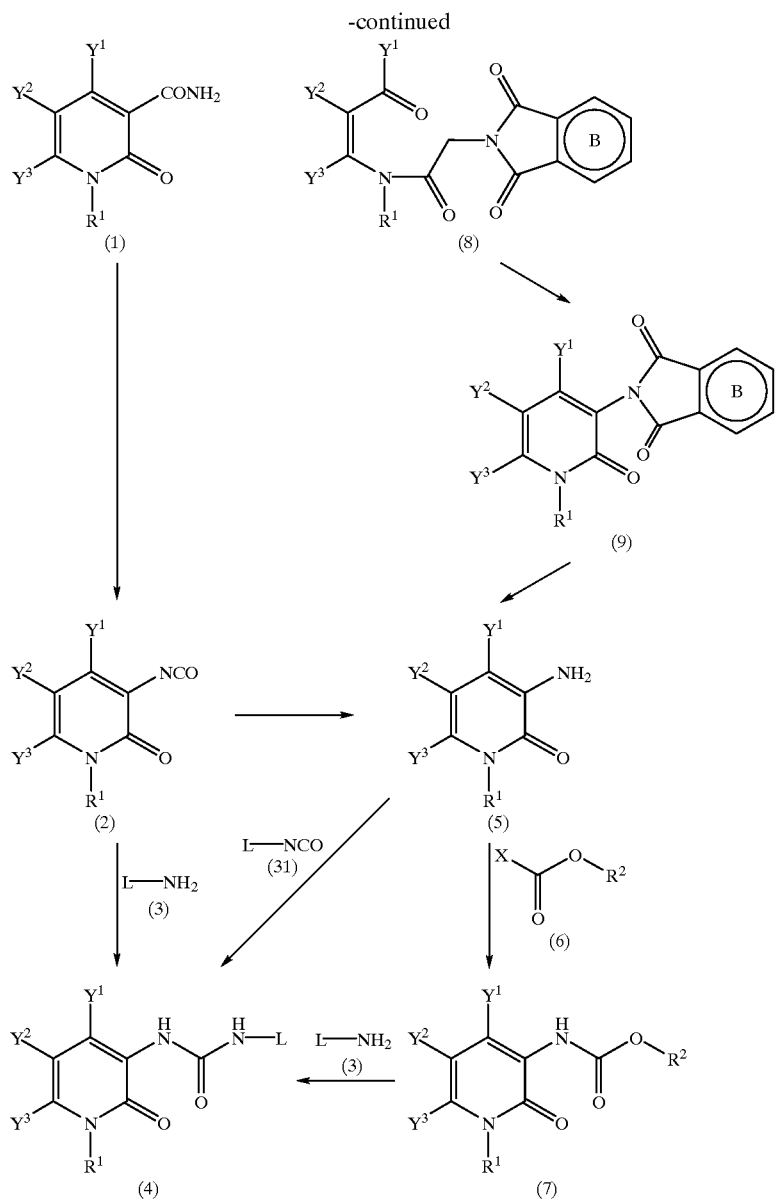

wherein L is an alkyl group, a substituted alkyl group, an alkenyl group, a substituted alkenyl group, a cycloalkyl group, a substituted cycloalkyl group, an aromatic group, or a substituted aromatic group; Ring B is a substituted or unsubstituted benzene ring; $R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; $R^2$ is a substituted or unsubstituted lower alkyl group, or a substituted or unsubstituted phenyl group; $R^{10}$ is a lower alkyl group; X is a chlorine atom or a bromine atom; $Y^1$ is a hydrogen atom, an alkyl group, a substituted alkyl group, a cycloalkyl group, a substituted cycloalkyl group, an aromatic group, or a substituted aromatic group; and $Y^2$ and $Y^3$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower alkylsulfonyl group, an alkyl group, a substituted allyl group, a cycloalkyl group, a substituted cycloalkyl group, an aromatic group, a substituted aromatic group, or $Y^2$ and $Y^3$ may combine each other together with the carbon atoms to which they bond, and form a substituted or unsubstituted pyridine ring.

a) Step from the compound (15) to the compound (1):

The carbamoylpyridone derivative of the formula (1) can preferably be obtained by reacting the ester derivative of the formula (15) with formaldehyde in an amount of 1 to 10 mole equivalents, preferably in an amount of 2 to 7 mole equivalents, in the presence of a base (e.g., an alkali metal salt of alcohol such as sodium methoxide, sodium ethoxide, or an alkali metal ammonia such as sodium amide) in an amount of 1 to 10 mole equivalents, preferably in an amount of 2 to 7 equivalents, in a solvent at a temperature of from room temperature to 100° C., preferably at a temperature of from 50° C. to 80° C. The solvent may be any solvent which does not disturb the reaction, for example, ethers (e.g., dimethoxyethane, tetrahydrofuran, dioxane, etc), aromatic hydrocarbons (e.g., benzene, toluene, xylene, etc.), halogenated hydrocarbons (e.g., chloroform, dichloroethane, chlorobenzene, dichlorobenzene, etc.), and amides (e.g., N,N-dimethylformamide, N,N-dimethylacetamide, etc.). The preferable solvent is N,N-dimethylformamide. The amide derivative (1) can be also obtained by treating the ester derivative (15) with an excess amount of liquid ammonia in a solvent or without solvent at a temperature of from 0° C. to 120° C., preferably at a temperature of from room temperature to 60° C., and if necessary, under pressure using an autoclave. The solvent is usually methanol.

b) Step from the compound (16) to the compound (1):

The carbamoylpyridone derivative of the formula (1) can be also prepared by converting the carboxylic acid derivative (16) to an acid halide (e.g., an acid chloride or acid bromide) thereof, and reacting with ammonia. The solvent may be any solvent which does not disturb the reaction, for example, ethers (e.g., diethyl ether, dimethoxyethane, tetrahydrofuran, dioxane, etc), aromatic hydrocarbons (e.g., benzene, toluene, xylene, etc.), halogenated hydrocarbons (e.g., dichloromethane, chloroform, dichloroethane, chlorobenzene, dichlorobenzene, etc.), and amides (e.g., N,N-dimethylformamide, N,N-dimethylacetamide, etc.). The conversion to an acid halide may be carried out by a conventional method, for example, an acid chloride can preferably be obtained by reacting with thionyl chloride in an amount of 1 to 3 mole equivalents at a temperature of from 50° C. to 80° C. in an aromatic hydrocarbons (e.g., benzene, toluene, etc.). The reaction with ammonia is carried out by a conventional method, for example, by reacting with conc. aqueous ammonia in a solvent at a temperature of from −10° C. to 60° C., preferably at a temperature of from 0° C. to 30° C. The solvent may be any solvent which does not disturb the reaction, for example, ethers (e.g., diethyl ether, dimethoxyethane, tetrahydrofuran, dioxane, etc), aromatic hydrocarbons (e.g., benzene, toluene, xylene, etc.), halogenated hydrocarbons (e.g., dichloromethane, chloroform, dichloroethane, chlorobenzene, dichlorobenzene, etc.), and amides (e.g., N,N-dimethylformamide, N,N-dimethylacetamide, etc.).

c) Steps from the compound (1) to the compound (4), and from the compound (5) to the compound (4):

The 2-carbamoylpyridone derivative (1) is reacted with lead tetraacetate in an amount of 1 to 3 mole equivalents, preferably in an amount of 1 to 1.5 mole equivalent in a solvent at a temperature of from 0° C. to 80° C., preferably at a temperature of from room temperature to 60° C., to give the isocyanate derivative (2). The solvent may be any solvent which does not disturb the reaction, for example, aromatic hydrocarbons (e.g., benzene, toluene, xylene, etc.), halogenated hydrocarbons (e.g., dichloromethane, dichloroethane, etc.), and amides (e.g., N,N-dimethylformamide, N,N-dimethylacetamide, etc.). The preferable solvent is N,N-dimethylformamide. The isocyanate derivative (2) thus obtained may be isolated and subjected to the subseqent reaction into a new solvent, or alternatively the reaction mixture may be used in the subsequent reaction without isolation of the isocyanate derivative (2), the reaction is carried out with the amine derivative (3) in an amount of 1 to 3 mole equivalents, preferably in an amount of 1 to 1.5 mole equivalents at a temperature of from 0° C. to 120° C., preferably at a temperature of from room temperature to 60° C., up to a boiling point of the solvent, to give the 2-pyridone derivative (4). The solvent may be any solvent which does not disturb the reaction, for example, ethers (e.g., diethyl ether, dimethoxyethane, tetrahydrofuran, dioxane, etc), aromatic hydrocarbons (e.g., benzene, toluene, xylene, etc.), esters (e.g., ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitriles (e.g., acetonitrile, isobutyronitrile, etc.), and amides (e.g., N,N-dimethylformamide, N,N-dimethylacetamide, etc.). The preferable solvent is aromatic hydrocarbons (e.g., benzene, toluene, etc.), halogenated hydrocarbons (e.g., dichloromethane, dichloroethane, etc.), and amides (e.g., N,N-dimethylformamide, N,N-dimethylacetamide, etc.). Especially preferable solvent is N,N-dimethylformamide.

When the amine derivative (3) is used in the form of an acid addition salt thereof, the reaction may smoothly proceed by converting the compound (3) into a free form, if necessary. In this case, an agent for converting the compound (3) into a free form is preferably a tertiary amine such as triethylamine, etc., or pyridine, etc.

On the other hand, the carbamoylpyridone derivative (1) is converted into the isocyanate derivative (2) by reacting it with a hypochlorite or a hypobromite in an amount of 1 to 10 mole equivalents, preferably in an amount of 1 to 5 mole equivalent in a mixed solvent of water and an organic solvent at a temperature of from 0° C. to 80° C., preferably at a temperature of from room temperature to 50° C., and then further reacted with the amine derivative (3) in an amount of 1 to 3 mole equivalents, preferably in an amount of 1 to 1.5 mole equivalent, to give the pyridone derivative (4). When the isocyanate derivative (2) is prepared, the reaction may proceed quickly by addition of a phase transfer catalyst in an amount of 0.05 to 0.2 mole equivalent. The phase transfer catalyst is preferably tetrabutylammonium hydrogen sulfate. The preferable hypochlorite or hypobromite is sodium hypobromite. The sodium hypobromite is usually prepared from aqueous sodium hydroxide solution and bromine at 0° C. to 10° C. in the reaction system. The organic solvent may be any solvent which does not disturb the reaction, for example, ethers (e.g., dimethoxyethane, tetrahydrofuran, dioxane, etc), aromatic hydrocarbons (e.g., benzene, toluene, xylene, etc.), halogenated hydrocarbons (e.g., dichloromethane, chloroform, dichloroethane, chlorobenzene, dichlorobenzene, etc.), and amides (e.g., N,N-dimethylformamide, N,N-dimethylacetamide, etc.). When the isocyanate derivative (2) is reacted with the amine derivative (3), the yield of the reaction may be improved by addition of acetic acid in a volume of 10 to 30% of the volume of the reaction solvent.

The compound (5) and the compound (31) are reacted in the same manner as in the above reaction of the compound (2) and the compound (3) to give the compound (4). The compound (31) is disclosed in literatures or may be prepared by a conventional method for preparation of an isocyanate as disclosed in literatures. Besides, in the same manner as in the preparation of the compound (2) from the compound (1), the compound (31) can be prepared from a compound of the formula (33):

L—CONH$_2$                 (33)

which is disclosed in literatures or may be prepared by a conventional method for preparation of an amide compound.

d) Step from the compound (1) to the compound (5):

The carbamoylpyridone derivative (1) is reacted with a hypochlorite or hypobromite in an amount of 1 to 10 mole equivalents, preferably in an amount of 1 to 5 mole equivalents in a mixed solvent of water and an organic solvent at a temperature of from 0° C. to 80° C., preferably at a temperature of from room temperature to 50° C., and the resulting isocyanate derivative (2) is subjected to hydrolysis to give the aminopyridone derivative (5). By addition of a phase transfer catalyst in an amount of 0.05 to 0.2 mole equivalent in the step of production of the isocyanote derivative, the reaction may quickly proceed. The phase transfer catalyst is preferably tetrabutylammonium hydrogen sulfate. The hydrolysis is usually carried out by subsequently stirring the reaction mixture containing the compound (2) at 30° C. to 50° C. The preferable hypochlorite or hypobromite is, for example, sodium hypobromite. The sodium hypobromite is usually prepared from an aqueous sodium hydroxide solution and bromine at 0° C. to 10° C. The solvent may be any solvent which does not disturb the reaction, for example, ethers (e.g., diethyl ether, dimethoxyethane, tetrahydrofuran, dioxane, etc.), aromatic hydrocarbons (e.g., benzene, toluene, xylene, etc.), halogenated hydrocarbons (e.g., dichloromethane, chloroform, dichloroethane, chlorobenzene, dichlorobenzene, etc.), and amides (e.g., N,N-dimethylformamide, N,N-dimethylacetamide, etc.). The preferable solvent is, for example, tetrahydrofuran and toluene.

The carbamoylpyridone derivative (1) can be converted into the aminopyridone derivative (5) by Hofmann reaction. The Hofmann reaction is carried out by reacting with a hypochlorite or a hypobromite in an amount of 1 to 3 mole equivalents, preferably in an amount of 1 to 1.5 mole equivalent in a solvent at a temperature of from 0° C. to 80° C., preferably at a temperature of from room temperature to 50° C. The hypochlorite or hypobromite is usually sodium hypobromite. The solvent may be any solvent which does not disturb the reaction, for example, ethers (e.g., diethyl ether, dimethoxyethane, tetrahydrofuran, dioxane, etc.), aromatic hydrocarbons (e.g., benzene, toluene, xylene, etc.), halogenated hydrocarbons (e.g., dichloromethane, chloroform, dichloroethane, chlorobenzene, dichlorobenzene, etc.), and amides (e.g., N,N-dimethylformamide, N,N-dimethylacetamide, etc.).

e) Step from the compound (5) to the compound (4):

The aminopyridone derivative (5) is reacted with a halocarbonate (6) in an amount of 1 to 10 mole equivalents, preferably in an amount of 1 to 3 mole equivalents, at a temperature of from room temperature to a boiling point of the solvent, preferably at a temperature of from room temperature to 80° C., and the resulting carbamic acid ester derivative (7) is reacted with the amine derivative (3) in an amount of 1 to 5 mole equivalents, preferably 1 to 2 mole equivalents at a temperature of from room temperature to a boiling point of the solvent, preferably at a temperature of from room temperature to 100° C., in the presence of 4-dimethylaminopyridine in an amount of 1 to 3 mole equivalents, preferably in an amount of 1 to 1.5 mole equivalent, to give the pyridone derivative (4). The preferable halocarbonate is phenyl chlorocarbonate. The reaction is usually carried out in a solvent, and the solvent may be any solvent which does not disturb the reaction, for example, ethers (e.g., isopropyl ether, tetrahydrofuran, dioxane, etc.), aromatic hydrocarbons (e.g., benzene, toluene, etc.), esters (e.g., methyl acetate, ethyl acetate, etc.), halogenated solvents (e.g., dichloromethane, chloroform, etc.), and N,N-dimethylformamide, dimethylsulfoxide, etc. The reaction may be promoted by addition of a base. The base includes, for example, sodium carbonate, potassium carbonate, triethylamine, pyridine, N,N-dimethylaniline, etc.

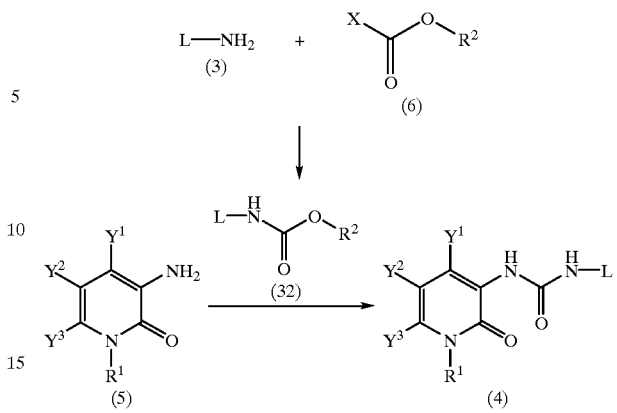

wherein $R^1$, $R^2$, $Y^1$, $Y^2$, $Y^3$ and L are as defined above.

Alternatively, in the same manner as in the preparation of the carbamic acid ester derivative (7) from the amine derivative (5) as mentioned above, the carbamic acid ester derivative (32) is obtained from the amine derivative (3) and the halocarbonate (6) in an amount of 1 to 10 mole equivalents, preferably in an amount of 1 to 3 mole equivalents, and said compound (32) is reacted with the amine derivative (5) in the same manner as in the preparation of the pyridone derivative (4) from the amine derivative (7) as mentioned above, to give the pyridone derivative (4).

f) Step from the compound (17) to the compound (8):

The aminoketone derivative (17) is reacted with an acid halide of N-phthaloylglycine of the formula (18) in an amount of 1 to 5 mole equivalents, preferably in an amount of 1 to 2.5 mole equivalents, in a solvent, at a temperature of from room temperature to 100° C., preferably at a temperature of from room temperature to 80° C., to give the amide derivative (8). The reaction is preferably carried out by addition of a base in an amount of 1 mole equivalent or more. The base includes, for example, a tertiary amine such as triethylamine, or pyridine. The solvent may be any solvent which does not disturb the reaction, for example, ethers (e.g., dimethoxyethane, tetrahydrofuran, dioxane, etc), aromatic hydrocarbons (e.g., benzene, toluene, xylene, etc.), esters (e.g., ethyl acetate, propyl acetate, etc.), halogenated hydrocarbons (e.g., dichloromethane, chloroform, dichloroethane, chlorobenzene, dichlorobenzene, etc.), nitrites (e.g., acetonitrile, isobutyronitrile, etc.), and amides (e.g., N,N-dimethylformamide, N,N-dimethylacetamide, etc.). The preferable solvent may be aromatic hydrocarbons such as benzene, toluene, etc. The amide derivative (8) can usually be used in the subsequent reaction without further purification. Moreover, the reaction mixture containing the amide derivative (8) can also be used in the subsequent reaction.

g) Step from the compound (8) to the compound (9):

Subsequently, the amide derivative (8) is subjected to cyclization reaction by heating it in a solvent in the presence of a base in an amount of 1 to 20 mole equivalents, preferably in an amount of 1 to 7 mole equivalents, at 50-120° C., preferably at 70–110° C., to give the 1,2-dihydro-2-pyridone derivative (9). The compound (9) is usually used in the subsequent reaction without further purification. The base is preferably an alkali metal carbonate such as sodium carbonate, potassium carbonate, etc. The solvent may be aromatic hydrocarbons (e.g., benzene, toluene, xylene, etc.), and amides (e.g., N,N-dimethylformamide, N,N-dimethylacetamide, etc.). The preferable solvent is N,N-dimethylacetamide.

h) Step from the compound (9) to the compound (5):

The 3-aminopyridone derivative (5) is prepared by removing the protecting phthaloyl group of the 1,2-dihydro-2-pyridone derivative (9). The removal of the protecting phthaloyl group may be carried out by a conventional method which is usually used in the field of the organic chemistry, for example, as described in PROTECTIVE GROUPS IN ORGANIC SYNTHESIS, 2nd ed., John Wiley & Sons, Inc.; New York. The preferable method of deprotection is a method of adding an excess amount of an alcohol solution or aqueous solution of a lower alkylamine (e.g., methylamine) at 0–50° C., preferably at room temperature, to the reaction system wherein the compound (9) is produced.

i) Step of preparing the compound (17):

The aminoketone derivative (17) wherein $R^1$ is a hydrogen atom, i.e., the derivative (19) may be prepared by the method disclosed in the literature (e.g., J. Heterocyclic Chem., 2, 105–112, 1989; J. Heterocyclic Chem., 13, 1283–1288, 1976) or a modified method thereof. In addition, the aminoketone derivative (17) wherein $R^1$ is a group other than a hydrogen atom may be prepared by the following Reaction Scheme.

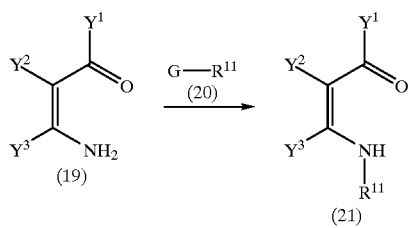

wherein $Y^1$, $Y^2$ and $Y^3$ are as defined above, $R^{11}$ is an alkyl group, a substituted alkyl group, an alkenyl group, a substituted alkenyl group, an alkynyl group, a substituted alkynyl group, a cycloalkyl group, or a substituted cycloalkyl group, and G is a leaving group.

The aminoketone derivative (19) is reacted with an alkylating agent (20) in the presence of a base at a temperature of from 0° C. to 150° C., preferably at a temperature of from room temperature to 80° C. in a solvent to give the compound (21). The solvent may be alcohols (e.g., methanol, ethanol, etc.), ethers (e.g., tetrahydrofuran, dioxane, etc.), ketones (e.g., acetone, 2-butanone, etc.), dimethylformamide, etc. The base may be an alkali metal hydroxide (e.g., sodium hydroxide, potassium hydroxide, etc.), an alkali metal alcoholate (e.g., sodium methoxide, sodium ethoxide, potassium t-butoxide, etc.), an alkali metal hydride (e.g., sodium hydride, etc.), an alkali metal carbonate (e.g., potassium carbonate, sodium carbonate, etc.), and an organic base (e.g., triethylamine). The leaving group for G is usually a halogen atom such as chlorine, bromine, iodine, etc., or aromatic sulfonyloxy group such as p-toluenesulfonyloxy group.

The ester derivative (15) and the carboxylic acid derivative (16) may be prepared by the method disclosed in the literature (e.g., JP-A-9-48780; Australian J. Chem., 1983, 36, 1431; J. Chem. Soc., 1908, 1022; J. Chem. Soc., 1904, 1726; J. Chem. Soc., 1915, 792; J. Am. Chem. Soc., 1956, 78, 4683), or a modified method thereof.

The present compound (10) wherein Z is a direct bond may be prepared by the following method.

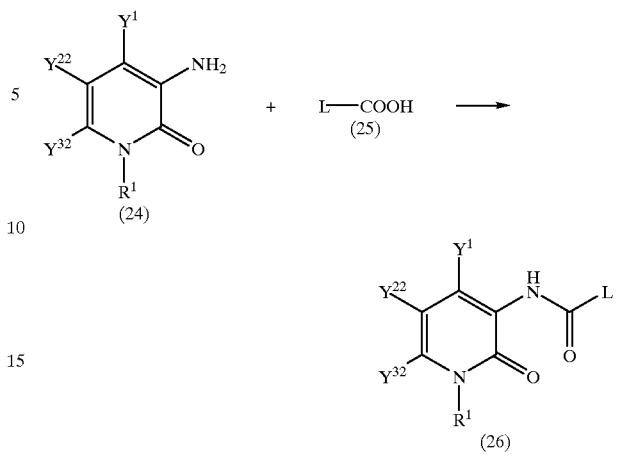

wherein L, $R^1$, $Y^1$, $Y^{22}$ and $Y^{32}$ are as defined above.

The amine derivative (24) or an acid addition salt thereof is condensed with the carboxylic acid derivative (25) using a condensing agent in a solvent at a temperature of from 0° C. to 100° C., preferably at a temperature of from 0° C. to 60° C., and if necessary, the resultant is further subjected to deprotection reaction to give the amide derivative (11). The condensing agent may be dicyclohexylcarbodiimide (DCC), N,N'-carbodiimidazole, diethyl cyanophosphate (DEPC), 1-ethyl-3-(3'-dimethylaminopropyl)carbodiimide hydrochloride (WSC), etc. The reaction may preferably proceed by addition of a base in an amount of 1 to 5 mole equivalents, preferably in an amount of 1 to 3 mole equivalents, to the amount of the amine derivative (24) or an acid addition salt thereof. The base may be a tertiary amine such as triethylamine, diisopropylethylamine, or pyridine, etc. The solvent may be any solvent which does not disturb the reaction, for example, ethers (e.g., diethyl ether, dimethoxyethane, tetrahydrofuran, dioxane, etc.), aromatic hydrocarbons (e.g., benzene, toluene, xylene, etc.), esters (e.g., ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitrites (e.g., acetonitrile, isobutyronitrile, etc.), and amides (e.g., N,N-dimethylformamide, N, N-dimethylacetamide, etc.).

Alternatively, the carboxylic acid derivative (25) is converted into a reactive derivative thereof, which is further reacted with the amine derivative (24) in a solvent at a temperature of from −10° C. to 120° C., preferably at a temperature of from 0° C. to 60° C. to give the amide derivative (26). The reactive derivative of the carboxylic acid derivative (25) may be, for example, an acid chloride, an acid bromide, an acid anhydride, or a mixed acid anhydride with methyl carbonate, ethyl carbonate, or the like, and the reaction may preferably proceed by addition of a base in an amount of 1 to 5 mole equivalents, preferably in an amount of 1 to 3 mole equivalents. The base may be a tertiary amine (e.g., triethylamine), pyridine, an alkali metal carbonate (e.g., sodium carbonate, potassium carbonate), and an alkali metal hydrogen carbonate (e.g., sodium hydrogen carbonate). The solvent may be any solvent which does not disturb the reaction, for example, ethers (e.g., diethyl ether, dimethoxyethane, tetrahydrofuran, dioxane, etc.), aromatic hydrocarbons (e.g., benzene, toluene, xylene, etc.), esters (e.g., ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitriles (e.g., acetonitrile, isobutyronitrile, etc.), and amides (e.g., N,N-dimethylformamide, N,N-dimethylacetamide, etc.).

Some of the present compounds (10) wherein Z is —NH— can also be prepared by the following method.

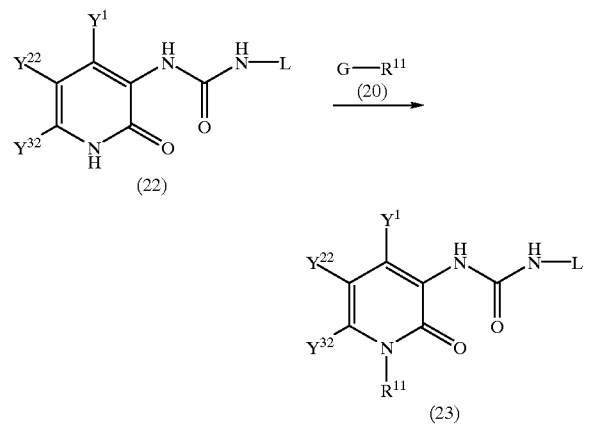

wherein L, $R^{11}$, $Y^1$, $Y^{22}$, $Y^{32}$ and G are as defined above.

The urea derivative (22) is converted into the urea derivative (23) by reacting with an alkylating agent (20). The alkylation reaction is carried out in a solvent at a temperature of from 0° C. to 100° C., preferably at a temperature of from room temperature to 70° C. in the presence of a base. The solvent may be, for example, ethers (e.g., tetrahydrofuran, dioxane, etc.), ketones (e.g., acetone, 2-butanone, etc.), aromatic hydrocarbons (e.g., benzene, toluene, etc.), and dimethylformamide. The base may be sodium hydride, potassium carbonate, sodium carbonate, triethylamine, etc. The leaving group for G is usually a halogen atom (e.g., chlorine, bromine, iodine, etc.) or an aromatic sulfonyloxy group (e.g., p-toluenesulfonyloxy group).

The substituents for L, $R^1$, $Y^1$, $Y^{22}$ and $Y^{32}$ of the pyridone derivative (10) can be converted each other, if necessary. For example, a lower alkylthio group can be converted into a lower alkylsulfonyl group by oxidation, a nitro group can be converted into an amino group by reduction reaction, an amino group can be converted into a mono- or di-alkyl group by alkylation, or an amino group can be acylated. Further, a 3-chloropropoxy group is converted into a 3-(1-imidazolyl)-propoxy group. In addition, a halogen atom such as bromine, iodine can be converted into a 1-propargyl group having a hydroxy group or an amino group at the 3-position by using a palladium catalyst. Said propargyl group can be further converted into a propyl group by hydrogenation reaction. Such conversion reactions of the substituents can be carried out by a conventional technique which is usually used in the field of the organic chemistry.

The alkylation reaction as shown in the following scheme may be carried out as one of these conversion reactions of substituents.

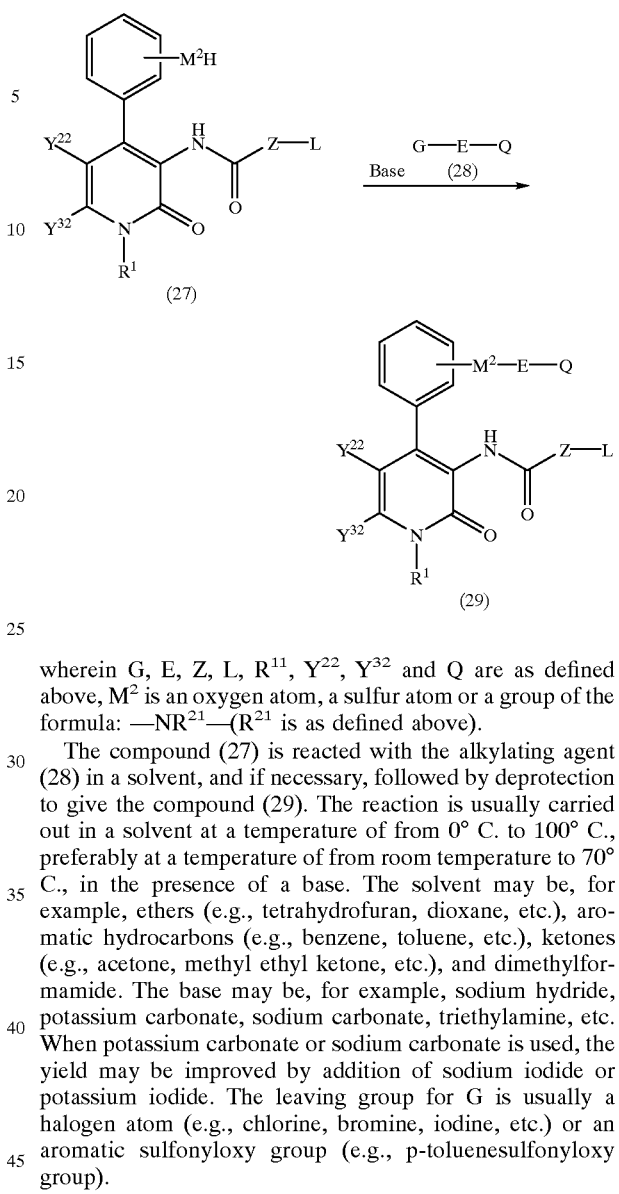

wherein G, E, Z, L, $R^{11}$, $Y^{22}$, $Y^{32}$ and Q are as defined above, $M^2$ is an oxygen atom, a sulfur atom or a group of the formula: —$NR^{21}$— ($R^{21}$ is as defined above).

The compound (27) is reacted with the alkylating agent (28) in a solvent, and if necessary, followed by deprotection to give the compound (29). The reaction is usually carried out in a solvent at a temperature of from 0° C. to 100° C., preferably at a temperature of from room temperature to 70° C., in the presence of a base. The solvent may be, for example, ethers (e.g., tetrahydrofuran, dioxane, etc.), aromatic hydrocarbons (e.g., benzene, toluene, etc.), ketones (e.g., acetone, methyl ethyl ketone, etc.), and dimethylformamide. The base may be, for example, sodium hydride, potassium carbonate, sodium carbonate, triethylamine, etc. When potassium carbonate or sodium carbonate is used, the yield may be improved by addition of sodium iodide or potassium iodide. The leaving group for G is usually a halogen atom (e.g., chlorine, bromine, iodine, etc.) or an aromatic sulfonyloxy group (e.g., p-toluenesulfonyloxy group).

The intermediate (2) or (5) of the present invention may be prepared, for example, by the method as disclosed below or a modified method thereof.

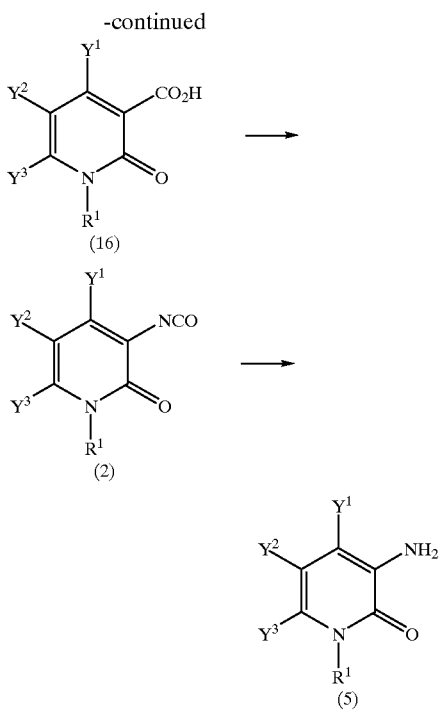

wherein $R^1$, $R^{11}$, $Y^1$, $Y^2$, $Y^3$ and G are as defined above, and $R^{10}$ is a lower alkyl group.

The starting compound (30) may be prepared by the method disclosed in the literature (e.g., JP-A-9-48780; Australian J. Chem., 1983, 36, 1431; J. Chem. Soc., 1908, 1022; J. Chem. Soc., 1904, 1726; J. Chem. Soc., 1915, 792; J. Am. Chem. Soc., 1956, 78, 4683) or a modified method thereof. The lower alkyl group for $R^{10}$ is preferably an alkyl group having 1 to 4 carbon atoms such as methyl, ethyl, propyl, isopropyl, butyl, etc.

The ester derivative (30) is converted into the compound (15) by alkylation reaction, if necessary. The alkylation reaction is carried out by reacting with the alkylating agent (20) in a solvent at a temperature of from 0° C. to 150° C., preferably at a temperature of from room temperature to 80° C., in the presence of a base. The solvent may be alcohols (e.g. methanol, ethanol, etc.), ethers (e.g., tetrahydrofuran, dioxane, etc.), ketones (e.g., acetone, 2-butanone, etc.), and dimethylformamide. The base may be sodium hydroxide, potassium hydroxide, sodium methoxide, sodium ethoxide, potassium t-butoxide, sodium hydride, potassium carbonate, sodium carbonate, triethylamine, etc. The leaving group for G is usually a halogen atom (e.g. chlorine, bromine, iodine, etc.) or an aromatic sulfonyloxy group (e.g., p-toluenesulfonyloxy group, etc.).

Subsequently, the compound (15) is subjected to hydrolysis to give the carboxylic acid derivative (16). The hydrolysis is carried out by a conventional method, for example, by using a hydroxide of an alkali metal or alkaline earth metal (e.g., sodium hydroxide, potassium hydroxide, barium hydroxide, etc.), in a solvent (e.g., methanol, ethanol, isopropanol, tetrahydrofuran, dioxane, dimethoxyethane, etc.) at a temperature of from 0° C. to 150° C., preferably at a temperature of from 0° C. to 100° C. The carboxylic acid derivative (16) is converted into an acid azide thereof by using an azidating agent (e.g., diphenylphosphorylazide (DPPA), etc.) in an amount of 1 to 3 mole equivalents, in a solvent in the presence of a base (e.g., triethylamine, N-methylmorpholine, etc.) at a temperature of from 0° to 120° C., preferably at a temperature of from room temperature to 80° C., and the resulting acid azide compound is usually heated at a temperature of from 20° C. to 150° C., preferably at a temperature of from 30° C. to 100° C. without isolation from the reaction system, to give the compound (2). Moreover, in the same manner as in the hydrolysis of the compound (15), the compound (2) is subjected to hydrolysis to give the compound (5).

The compounds of the present invention prepared by the present methods and the intermediates thereof may be purified by a conventional method, for example, column chromatography, recrystallization, etc. The solvent for recrystallization may properly be selected from alcohols (e.g., methanol, ethanol, 2-propanol, etc.), ethers (e.g., diethyl ether, etc.), esters (e.g., ethyl acetate, etc.), aromatic solvents (e.g., toluene, etc.), ketones (e.g., acetone, etc.), hydrocarbons (e.g., hexane, etc.) or a mixture of these solvent.

The compounds of the present invention prepared by the above Processes are listed below. The abbreviation used in Tables 1 to 12 is shown. That is, Imd denotes 1-imidazolyl group, 2-Me-Imd denotes 2-methyl-1-imidazolyl group, Pyrz denotes 1-pyrazolyl group, Triaz denotes 1,2,4-triazol-1-yl group, Morp denotes morpholino group, Quin denotes quinolyl group, Py denotes pyridyl group, Pipe denotes piperidino group, Pyrro denotes 1-pyrrolidinyl group, Pipera denotes 1-piperazinyl group, Phe denotes phenyl group, Me denotes methyl group, Et denotes ethyl group, Pr denotes propyl group, iPr denotes isopropyl group, Bu denotes butyl group, tBu denotes tert-butyl group, Hex denotes hexyl group, cHex denotes cyclohexyl group, and Bn denotes benzyl group, respectively.

TABLE 1

| $Y^1$ | $Y^2$ | $Y^3$ | $R^1$ | L |
|---|---|---|---|---|
| Me | H | H | Bu | 2,6-di-iPr-Phe |
| Et | H | H | Bu | 2,6-di-iPr-Phe |
| Pr | H | H | Bu | 2,6-di-iPr-Phe |
| iPr | H | H | Bu | 2,6-di-iPr-Phe |
| Bu | H | H | Bu | 2,6-di-iPr-Phe |
| $(CH_2)_9CH_3$ | H | H | Bu | 2,6-di-iPr-Phe |
| $(CH_2)_{10}CH_3$ | H | H | Bu | 2,6-di-iPr-Phe |
| $(CH_2)_{14}CH_3$ | H | H | Bu | 2,6-di-iPr-Phe |
| Ph | H | H | Bu | 2,6-di-iPr-Phe |
| 2-Py | H | H | Bu | 2,6-di-iPr-Phe |
| 3-Py | H | H | Bu | 2,6-di-iPr-Phe |
| 4-Py | H | H | Bu | 2,6-di-iPr-Phe |
| H | Ph | H | Bu | 2,6-di-iPr-Phe |
| H | H | Ph | H | 2,6-di-iPr-Phe |
| H | H | Ph | Me | 2,6-di-iPr-Phe |
| H | H | Ph | Et | 2,6-di-iPr-Phe |
| H | H | Ph | Pr | 2,6-di-iPr-Phe |
| H | H | Ph | iPr | 2,6-di-iPr-Phe |

TABLE 2

| A¹ | A² | A³ | A⁴ | Y² | Y³ | R¹ | L |
|---|---|---|---|---|---|---|---|
| MeO | H | H | H | H | H | H | 2,6-di-iPr-Phe |
| MeO | H | H | H | H | H | Me | 2,6-di-iPr-Phe |
| MeO | H | H | H | H | H | Et | 2,6-di-iPr-Phe |
| MeO | H | H | H | H | H | Pr | 2,6-di-iPr-Phe |
| MeO | H | H | H | H | H | iPr | 2,6-di-iPr-Phe |
| MeO | H | H | H | H | H | Bu | 2,6-di-iPr-Phe |
| MeO | H | H | MeO | H | H | H | 2,6-di-iPr-Phe |
| MeO | H | H | MeO | H | H | Me | 2,6-di-iPr-Phe |
| MeO | H | H | MeO | H | H | Et | 2,6-di-iPr-Phe |
| MeO | H | H | MeO | H | H | Pr | 2,6-di-iPr-Phe |
| MeO | H | H | MeO | H | H | iPr | 2,6-di-iPr-Phe |
| MeO | H | H | MeO | H | H | Bu | 2,6-di-iPr-Phe |
| EtO | H | H | MeO | H | H | Bu | 2,6-di-iPr-Phe |
| PrO | H | H | MeO | H | H | Bu | 2,6-di-iPr-Phe |
| iPrO | H | H | MeO | H | H | Bu | 2,6-di-iPr-Phe |
| MeO | H | H | MeO | Me | H | Bu | 2,6-di-iPr-Phe |
| MeO | H | MeO | H | H | H | Bu | 2,6-di-iPr-Phe |
| MeO | MeO | H | H | H | H | Bu | 2,6-di-iPr-Phe |
| MeO | H | H | Me | H | H | Bu | 2,6-di-iPr-Phe |
| MeO | H | H | F | H | H | Bu | 2,6-di-iPr-Phe |
| MeO | H | H | Cl | H | H | Bu | 2,6-di-iPr-Phe |
| MeO | H | H | Br | Me | H | Bu | 2,6-di-iPr-Phe |
| MeO | H | H | Br | H | H | Bu | 2,6-di-iPr-Phe |

TABLE 3

| A¹ | A⁵ | Y² | Y³ | R¹ | L |
|---|---|---|---|---|---|
| MeO | CH₂-3-Py | H | H | Bu | 2-iPr-Phe |
| MeO | CH₂-3-Py | H | H | Bu | 2,6-di-iPr-Phe |
| MeO | CH₂-3-Py | H | H | Bu | 2-Me-Phe |
| MeO | CH₂-3-Py | H | H | Bu | 2,6-di-Me-Phe |
| MeO | CH₂-3-Py | H | H | Bu | 2,4,6-tri-Me-Phe |
| MeO | CH₂-3-Py | H | H | Bu | 2-F-Phe |
| MeO | CH₂-3-Py | H | H | Bu | 2,6-di-F-Phe |
| MeO | CH₂-3-Py | H | H | Bu | 2,4,6-tri-F-Phe |
| MeO | CH₂-3-Py | H | H | Bu | 2-iPr-Phe |
| MeO | CH₂-3-Py | H | H | Bu | 2-iPr-6-Me-Phe |
| MeO | CH₂-3-Py | H | H | Bu | 2-Et-Phe |
| MeO | CH₂-3-Py | H | H | Bu | 2,6-di-Et-Phe |
| MeO | CH₂-3-Py | H | H | Bu | 2-iPr-6-Me-Phe |
| MeO | CH₂-3-Py | H | H | Bu | 2-Et-6-iPr-Phe |
| MeO | CH₂-3-Py | H | H | Bu | 2-Me-6-tBu-Phe |

TABLE 3-continued

| A¹ | A⁵ | Y² | Y³ | R¹ | L |
|---|---|---|---|---|---|
| MeO | CH₂-3-Py | H | H | Bu | 2,4,6-tri-MeO-Phe |
| MeO | CH₂-3-Py | H | H | Bu | 2-EtO-Phe |
| MeO | CH₂-3-Py | H | H | Bu | 2-MeS-Phe |
| MeO | CH₂-3-Py | H | H | Bu | 2-CF₃-Phe |
| MeO | CH₂-3-Py | H | H | Bu | 2-Br-Phe |
| MeO | CH₂-3-Py | H | H | Bu | 2,6-di-Br-Phe |
| MeO | CH₂-3-Py | H | H | Bu | 2-Cl-Phe |
| MeO | CH₂-3-Py | H | H | Bu | 2,6-di-Cl-Phe |
| MeO | CH₂-3-Py | H | H | Bu | 2-Cl-6-Me-Phe |
| MeO | CH₂-3-Py | H | H | Bu | 2,4-di-Cl-Phe |
| MeO | CH₂-3-Py | H | H | Bu | 2-Cl-3-Py |
| MeO | CH₂-3-Py | H | H | Bu | 3-Quin |
| MeO | CH₂-3-Py | H | H | Bu | 5-Quin |
| MeO | CH₂-3-Py | H | H | Bu | 6-Quin |
| MeO | CH₂-3-Py | H | H | Bu | 8-Quin |

TABLE 4

| A¹ | A⁵ | Y² | Y³ | R¹ | L |
|---|---|---|---|---|---|
| MeO | Bn | H | H | Bu | 2,6-di-iPr-Phe |
| MeO | CH₂-2-Py | H | H | Bu | 2,6-di-iPr-Phe |
| MeO | CH₂-4-Py | H | H | Bu | 2,6-di-iPr-Phe |
| MeO | (CH₂)₂—NMe₂ | H | H | Bu | 2,6-di-iPr-Phe |
| MeO | (CH₂)₂—NiPr₂ | H | H | Bu | 2,6-di-iPr-Phe |
| MeO | (CH₂)₂-Morp | H | H | Bu | 2,6-di-iPr-Phe |
| MeO | (CH₂)₂-Pipe | H | H | Bu | 2,6-di-iPr-Phe |
| MeO | (CH₂)₂-Pyrro | H | H | Bu | 2,6-di-iPr-Phe |
| MeO | (CH₂)₂-Pipera | H | H | Bu | 2,6-di-iPr-Phe |
| MeO | (CH₂)₂-Triaz | H | H | Bu | 2,6-di-iPr-Phe |
| MeO | (CH₂)₂—OH | H | H | Bu | 2,6-di-iPr-Phe |
| MeO | (CH₂)₂—OAc | H | H | Bu | 2,6-di-iPr-Phe |
| MeO | (CH₂)₂—Cl | H | H | Bu | 2,6-di-iPr-Phe |
| MeO | (CH₂)₂-2-Py | H | H | Bu | 2,6-di-iPr-Phe |
| MeO | (CH₂)₃-3-Py | H | H | Bu | 2,6-di-iPr-Phe |
| MeO | (CH₂)₃-4-Py | H | H | Bu | 2,6-di-iPr-Phe |
| MeO | (CH₂)₃—NMe₂ | H | H | Bu | 2,6-di-iPr-Phe |
| MeO | (CH₂)₃—NiPr₂ | H | H | Bu | 2,6-di-iPr-Phe |
| MeO | (CH₂)₃-Morp | H | H | Bu | 2,6-di-iPr-Phe |
| MeO | (CH₂)₃-Pipe | H | H | Bu | 2,6-di-iPr-Phe |
| MeO | (CH₂)₃-Pipera | H | H | Bu | 2,6-di-iPr-Phe |
| MeO | (CH₂)₃-Pyrro | H | H | Bu | 2,6-di-iPr-Phe |
| MeO | (CH₂)₃—OH | H | H | Bu | 2,6-di-iPr-Phe |
| MeO | (CH₂)₃—OAc | H | H | Bu | 2,6-di-iPr-Phe |
| MeO | (CH₂)₃—Cl | H | H | Bu | 2,6-di-iPr-Phe |

TABLE 4-continued

| A¹ | A⁵ | Y² | Y³ | R¹ | L |
|---|---|---|---|---|---|
| MeO | (CH₂)₃-Triaz | H | H | Bu | 2,6-di-iPr-Phe |
| MeO | CH₂-3-Py | H | H | H | 2,6-di-iPr-Phe |
| MeO | CH₂-3-Py | H | H | Me | 2,6-di-iPr-Phe |
| MeO | CH₂-3-Py | H | H | Et | 2,6-di-iPr-Phe |
| MeO | CH₂-3-Py | H | H | Pr | 2,6-di-iPr-Phe |
| MeO | CH₂-3-Py | H | H | iPr | 2,6-di-iPr-Phe |
| MeO | CH₂-3-Py | H | H | 3-Butenyl | 2,6-di-iPr-Phe |
| MeO | CH₂-3-Py | H | H | 3-Butynyl | 2,6-di-iPr-Phe |
| MeO | CH₂-3-Py | H | H | 4-Pentenyl | 2,6-di-iPr-Phe |

TABLE 5

| A¹ | A³ | Y² | Y³ | R¹ | L |
|---|---|---|---|---|---|
| MeO | CH₂-3-Py | H | H | CH₂-Ph | 2,6-di-iPr-Phe |
| MeO | CH₂-3-Py | H | H | CH₂-2-Py | 2,6-di-iPr-Phe |
| MeO | CH₂-3-Py | H | H | CH₂-3-Py | 2,6-di-iPr-Phe |
| MeO | CH₂-3-Py | H | H | CH₂-4-Py | 2,6-di-iPr-Phe |
| MeO | CH₂-3-Py | H | H | CH₂CO₂H | 2,6-di-iPr-Phe |
| MeO | CH₂-3-Py | H | H | CH₂CN | 2,6-di-iPr-Phe |
| MeO | CH₂-3-Py | H | H | CH₂OH | 2,6-di-iPr-Phe |
| MeO | CH₂-3-Py | H | H | CH₂OMe | 2,6-di-iPr-Phe |
| MeO | CH₂-3-Py | H | H | Bn | 2,6-di-iPr-Phe |
| MeO | CH₂-3-Py | H | H | (CH₂)₂OH | 2,6-di-iPr-Phe |
| MeO | CH₂-3-Py | H | H | (CH₂)₂CN | 2,6-di-iPr-Phe |
| MeO | CH₂-3-Py | H | H | (CH₂)₂NH₂ | 2,6-di-iPr-Phe |
| MeO | CH₂-3-Py | H | H | (CH₂)₂NMe₂ | 2,6-di-iPr-Phe |
| MeO | CH₂-3-Py | H | H | (CH₂)₂NHAc | 2,6-di-iPr-Phe |
| MeO | CH₂-3-Py | H | H | (CH₂)₃OH | 2,6-di-iPr-Phe |
| MeO | CH₂-3-Py | H | H | (CH₂)₃CN | 2,6-di-iPr-Phe |
| MeO | CH₂-3-Py | H | H | (CH₂)₃NH₂ | 2,6-di-iPr-Phe |
| MeO | CH₂-3-Py | H | H | (CH₂)₃NMe₂ | 2,6-di-iPr-Phe |
| MeO | CH₂-3-Py | H | H | (CH₂)₃NHAc | 2,6-di-iPr-Phe |
| Me | CH₂-3-Py | H | H | Bu | 2,6-di-iPr-Phe |
| Br | CH₂-3-Py | H | H | Bu | 2,6-di-iPr-Phe |
| Cl | CH₂-3-Py | H | H | Bu | 2,6-di-iPr-Phe |
| F | CH₂-3-Py | H | H | Bu | 2,6-di-iPr-Phe |
| CF₃ | CH₂-3-Py | H | H | Bu | 2,6-di-iPr-Phe |
| EtO | CH₂-3-Py | H | H | Bu | 2,6-di-iPr-Phe |
| BnO | CH₂-3-Py | H | H | Bu | 2,6-di-iPr-Phe |
| HO | CH₂-3-Py | H | H | Bu | 2,6-di-iPr-Phe |
| AcNH | CH₂-3-Py | H | H | Bu | 2,6-di-iPr-Phe |
| MeO | CH₂-3-Py | Me | H | Bu | 2,6-di-iPr-Phe |
| MeO | CH₂-3-Py | Me | H | Bu | 2,6-di-F-Phe |
| MeO | CH₂-3-Py | Me | H | Bu | 2,4,6-tri-F-Phe |

TABLE 5-continued

| A¹ | A³ | Y² | Y³ | R¹ | L |
|---|---|---|---|---|---|
| MeO | CH₂-3-Py | Me | H | Bu | 2,4,6-tri-MeO-Phe |
| MeO | CH₂-2-Py | Me | H | Bu | 2,6-di-iPr-Phe |

TABLE 6

| A¹ | A⁵ | Y² | Y³ | R¹ | L |
|---|---|---|---|---|---|
| MeO | CH₂-3-Py | Me | H | Bu | 2,6-di-iPr-Phe |
| MeO | (CH₂)₂-Morp | Me | H | Bu | 2,6-di-iPr-Phe |
| MeO | (CH₂)₂-Pipe | Me | H | Bu | 2,6-di-iPr-Phe |
| MeO | (CH₂)₂-Pyrro | Me | H | Bu | 2,6-di-iPr-Phe |
| MeO | (CH₂)₂-Triaz | Me | H | Bu | 2,6-di-iPr-Phe |
| MeO | (CH₂)₃-Morp | Me | H | Bu | 2,6-di-iPr-Phe |
| MeO | (CH₂)₃-Triaz | Me | H | Bu | 2,6-di-iPr-Phe |
| MeO | CH₂-2-Py | Me | H | (CH₂)₂OMe | 2,6-di-iPr-Phe |
| MeO | CH₂-2-Py | Me | H | (CH₂)₃CN | 2,6-di-iPr-Phe |

TABLE 7

| A¹ | A⁵ | Y² | R¹ | L |
|---|---|---|---|---|
| MeO | Me | H | Bu | 2,6-bis-MeS-4-Me-Phe |
| MeO | Me | H | Bu | 2,4-bis-MeS-6-Me-3-Py |
| MeO | Me | H | Bu | 2-tBu-5-(CH₂-Morp)-Phe |
| MeO | Me | H | Bu | 2-tBu-5-(CH₂-Pipe)-Phe |
| MeO | Me | H | Bu | 2-tBu-5-(CH₂-Pyrro)-Phe |
| MeO | Me | H | Bu | 2-tBu-5-(CH₂-Pipera)-Phe |
| MeO | Me | H | Bu | 2-tBu-5-(CH₂-Imd)-Phe |

TABLE 7-continued

| A¹ | A⁵ | Y² | R¹ | L |
|---|---|---|---|---|
| MeO | Me | H | Bu | 2-tBu-5-(CH₂-Pyrz)-Phe |
| MeO | Me | H | Bu | 2-tBu-5-.CH₂-(4-Me-Pyrz)-Phe |
| MeO | Me | H | Bu | 2-tBu-5-(CH₂—NMe₂)-Phe |
| MeO | Me | H | Bu | 2-tBu-5-(CH₂—NEt₂)-Phe |
| MeO | Me | H | Bu | 2-tBu-5-(CH₂—NPr₂)-Phe |
| MeO | Me | H | Bu | 2-tBu-5-(CH₂—NiPr₂)-Phe |
| MeO | Me | H | Bu | 2-tBu-5-{CH₂—NMe(—CH₂-2-Py)}-Phe |
| MeO | Me | H | Bu | 2-tBu-5-{CH₂—NMe(—CH₂-3-Py)}-Phe |
| MeO | Me | H | Bu | 2-tBu-5-{CH₂—NMe(—CH₂-4-Py)}-Phe |
| MeO | Me | H | Bu | 2-tBu-5-{CH₂—NEt(—CH₂-2-Py)}-Phe |
| MeO | Me | H | Bu | 2-tBu-5-{CH₂—NH(—CH₂-2-Py)}-Phe |
| MeO | Me | H | Bu | 2-iPr-5-(CH₂-Imd)-Phe |
| H | Me | H | Bu | 2,6-bis-MeS-4-Me-3-Py |
| H | Me | H | Bu | 2-tBu-5-(CH₂-Morp)-Phe |
| H | Me | H | Bu | 2-tBu-5-(CH₂-Pipe)-Phe |
| H | Me | H | Bu | 2-tBu-5-(CH₂-Pyrro)-Phe |
| H | Me | H | Bu | 2-tBu-5-(CH₂-Imd)-Phe |
| H | Me | H | Bu | 2-tBu-5-(CH₂-Pyrz)-Phe |
| H | Me | H | Bu | 2-tBu-5-CH₂-(4-Me-Pyrz)-Phe |
| H | Me | H | Bu | 2-tBu-5-(CH₂—NMe₂)-Phe |
| H | Me | H | Bu | 2-tBu-5-(CH₂—NEt₂)-Phe |
| H | Me | H | Bu | 2-tBu-5-(CH₂—NPr₂)-Phe |
| H | Me | H | Bu | 2-Bu-5-(CH₂—NiPr₂)-Phe |

TABLE 8

| A¹ | A⁵ | Y² | R¹ | L |
|---|---|---|---|---|
| H | Me | H | Bu | 2-tBu-5-{CH₂—NMe(—CH₂-2-Py)}-Phe |
| H | Me | H | Bu | 2-tBu-5-{CH₂—NMe(—CH₂-3-Py)}-Phe |
| H | Me | H | Bu | 2-tBu-5-{CH₂—NMe(—CH₂-4-Py)}-Phe |
| H | Me | H | Bu | 2-tBu-5-{CH₂—NEt(—CH₂-2-Py)}-Phe |
| H | Me | H | Bu | 2-tBu-5-{CH₂—NH(—CH₂-2-Py)}-Phe |
| H | Me | H | Bu | 2-iPr-5-(CH₂-Imd)-Phe |
| MeO | CH₂-3-Py | H | Bu | 2,6-di-MeS-4-Me-Phe |
| MeO | CH₂-3-Py | H | Bu | 2,6-di-MeS-6-Me-3-Py |
| MeO | CH₂-3-Py | H | Bu | 2-tBu-5-(CH₂-Morp)-Phe |
| MeO | CH₂-3-Py | H | Bu | 2-tBu-5-(CH₂-Pipe)-Phe |
| MeO | CH₂-3-Py | H | Bu | 2-tBu-5-(CH₂-Pyrro)-Phe |
| MeO | CH₂-3-Py | H | Bu | 2-tBu-5-(CH₂-Pipera)-Phe |
| MeO | CH₂-3-Py | H | Bu | 2-tBu-5-(CH₂-Imd)-Phe |
| MeO | CH₂-3-Py | H | Bu | 2-tBu-5-(CH₂-Pyrz)-Phe |
| MeO | CH₂-3-Py | H | Bu | 2-tBu-5-CH₂-(4-Me-Pyrz)-Phe |
| MeO | CH₂-3-Py | H | Bu | 2-iPr-5-CH₂-Imd-Phe |
| MeO | Me | Me | Bu | 2,6-di-MeS-4-Me-Phe |

TABLE 8-continued

| A¹ | A⁵ | Y² | R¹ | L |
|---|---|---|---|---|
| MeO | Me | Me | Bu | 2,4-di-MeS-6-Me-3-Py |
| MeO | Me | Me | Bu | 2-tBu-5-(CH₂-Morp)-Phe |
| MeO | Me | Me | Bu | 2-tBu-5-(CH₂-Pipe)-Phe |
| MeO | Me | Me | Bu | 2-tBu-5-(CH₂-Pyrro)-Phe |
| MeO | Me | Me | Bu | 2-tBu-5-(CH₂-Pipera)-Phe |
| MeO | Me | Me | Bu | 2-tBu-5-(CH₂-Imd)-Phe |
| MeO | Me | Me | Bu | 2-tBu-5-(CH₂-Pyrz)-Phe |
| MeO | Me | Me | Bu | 2-tBu-5-CH₂-(4-Me-Pyrz)-Phe |
| MeO | Me | Me | Bu | 2-iPr-5-CH₂-Imd-Phe |
| MeO | Me | Me | H | 2-tBu-5-(CH₂-Morp)-Phe |
| MeO | Me | Me | Me | 2-tBu-5-(CH₂-Morp)-Phe |
| MeO | Me | Me | Et | 2-tBu-5-(CH₂-Morp)-Phe |
| MeO | Me | Me | Pr | 2-tBu-5-(CH₂-Morp)-Phe |
| MeO | Me | Me | iPr | 2-tBu-5-(CH₂-Morp)-Phe |

TABLE 9

| A¹ | R⁵ | R⁷ | R⁶ | R¹⁷ | R¹ | Y² | L |
|---|---|---|---|---|---|---|---|
| MeO | H | H | H | H | Bu | H | 2,6-di-iPr-Phe |
| MeO | H | H | H | Me | Bu | H | 2,6-di-iPr-Phe |
| MeO | H | H | H | Et | Bu | H | 2,6-di-iPr-Phe |
| MeO | H | H | H | iPr | Bu | H | 2,6-di-iPr-Phe |
| MeO | H | H | H | Hex | Bu | H | 2,6-di-iPr-Phe |
| MeO | H | H | H | cHex | Bu | H | 2,6-di-iPr-Phe |
| MeO | H | H | H | CH₂NEt₂ | Bu | H | 2,6-di-iPr-Phe |
| MeO | H | H | H | (CH₂)₂NEt₂ | Bu | H | 2,6-di-iPr-Phe |
| MeO | H | H | Me | Me | Bu | H | 2,6-di-iPr-Phe |
| MeO | H | H | Et | Et | Bu | H | 2,6-di-iPr-Phe |
| MeO | H | H | Et | Et | Bu | Me | 2,6-di-iPr-Phe |
| MeO | H | H | iPr | iPr | Bu | H | 2,6-di-iPr-Phe |
| MeO | H | H | Hex | Hex | Bu | H | 2,6-di-iPr-Phe |
| MeO | H | H | Me | Bn | Bu | H | 2,6-di-iPr-Phe |
| MeO | H | H | Et | Bn | Bu | H | 2,6-di-iPr-Phe |
| MeO | H | H | H | CH₂-2-Py | Bu | H | 2,6-di-iPr-Phe |
| MeO | H | H | H | CH₂-3-Py | Bu | H | 2,6-di-iPr-Phe |
| MeO | H | H | H | CH₂-4-Py | Bu | H | 2,6-di-iPr-Phe |
| MeO | H | H | Me | CH₂-2-Py | Bu | H | 2,6-di-iPr-Phe |
| MeO | H | H | Me | CH₂-3-Py | Bu | H | 2,6-di-iPr-Phe |
| MeO | H | H | Me | CH₂-4-Py | Bu | H | 2,6-di-iPr-Phe |
| MeO | H | H | Me | CH₂-4-Py | Bu | Me | 2,6-di-iPr-Phe |

TABLE 9-continued

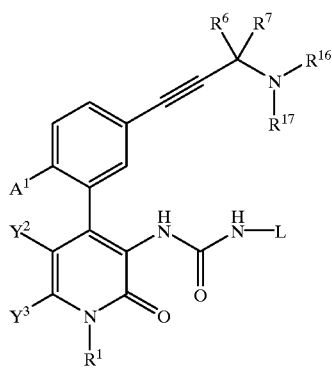

| A¹ | R⁵ | R⁷ | R⁶ | R¹⁷ | R¹ | Y² | L |
|---|---|---|---|---|---|---|---|
| MeO | H | H |  | (CH₂)₄ | Bu | H | 2,6-di-iPr-Phe |
| MeO | H | H |  | (CH₂)₅ | Bu | H | 2,6-di-iPr-Phe |
| MeO | H | H |  | (CH₂)₆ | Bu | H | 2,6-di-iPr-Phe |
| MeO | H | H |  | (CH₂)₄—O—(CH₂)₂ | Bu | H | 2,6-di-iPr-Phe |

TABLE 10

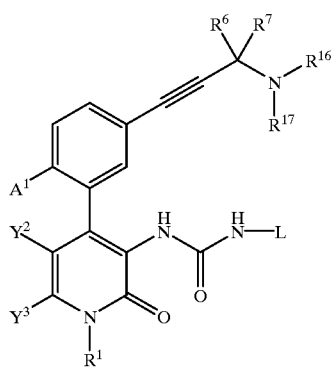

| A¹ | R⁶ | R⁷ | R¹⁶ | R¹⁷ | R¹ | Y² | L |
|---|---|---|---|---|---|---|---|
| MeO | H | H | Et | Et | Bu | H | 2-iPr-Phe |
| MeO | H | H | Et | Et | Bu | H | 2,4,6-tri-Me-Phe |
| MeO | H | H | Et | Et | Bu | H | 2,6-di-F-Phe |
| MeO | H | H | Et | Et | Bu | H | 2,4,6-tri-F-Phe |
| MeO | H | H | Et | Et | Bu | H | 2-Me-6-tBu-Phe |
| MeO | H | H | Et | Et | Bu | H | 2,4,6-tri-MeO-Phe |
| MeO | H | H | Et | Et | Bu | H | 2,6-bis-MeS-4-Me-Phe |
| MeO | H | H | Et | Et | Bu | H | 2-tBu-5-(CH₂-Imd)-Phe |
| MeO | H | H | Et | Et | Bu | H | 2-tBu-5-(CH₂-Pyrz)-Phe |
| MeO | H | H | Et | Et | Bu | H | 2-iPr-5-(CH₂-Imd)-Phe |
| EtO | H | H | Et | Et | Bu | H | 2-iPr-Phe |
| EtO | H | H | Et | Et | Bu | H | 2,6-di-iPr-Phe |
| EtO | H | H | Et | Et | Bu | H | 2,4,6-tri-Me-Phe |
| EtO | H | H | Et | Et | Bu | H | 2,6-di-F-Phe |
| EtO | H | H | Et | Et | Bu | H | 2,4,6-tri-F-Phe |
| EtO | H | H | Et | Et | Bu | H | 2-Me-6-tBu-Phe |
| EtO | H | H | Et | Et | Bu | H | 2,4,6-tri-MeO-Phe |
| EtO | H | H | Et | Et | Bu | H | 2,6-bis-MeS-4-Me-Phe |
| EtO | H | H | Et | Et | Bu | H | 2-tBu-5-(CH₂-Imd)-Phe |
| HO | H | H | Et | Et | Bu | H | 2-iPr-Phe |
| HO | H | H | Et | Et | Bu | H | 2,6-di-iPr-Phe |
| HO | H | H | Et | Et | Bu | H | 2,4,6-tri-Me-Phe |
| HO | H | H | Et | Et | Bu | H | 2,6-di-F-Phe |
| HO | H | H | Et | Et | Bu | H | 2,4,6-tri-F-Phe |
| HO | H | H | Et | Et | Bu | H | 2-Me-6-tBu-Phe |
| HO | H | H | Et | Et | Bu | H | 2,4,6-tri-MeO-Phe |
| HO | H | H | Et | Et | Bu | H | 2,6-bis-MeS-4-Me-Phe |
| HO | H | H | Et | Et | Bu | H | 2-tBu-5-(CH₂-Imd)-Phe |
| F | H | H | Et | Et | Bu | H | 2-iPr-Phe |

TABLE 10-continued

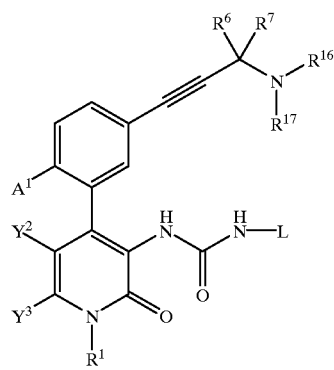

| A¹ | R⁶ | R⁷ | R¹⁶ | R¹⁷ | R¹ | Y² | L |
|---|---|---|---|---|---|---|---|
| F | H | H | Et | Et | Bu | H | 2,6-di-iPr-Phe |
| F | H | H | Et | Et | Bu | H | 2,4,6-tri-Me-Phe |

TABLE 11

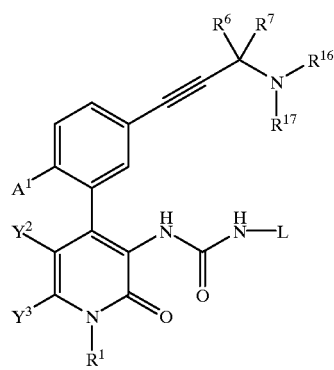

| A¹ | R⁶ | R⁷ | R¹⁶ | R¹⁷ | R¹ | Y² | L |
|---|---|---|---|---|---|---|---|
| F | H | H | Et | Et | Bu | H | 2,6-di-F-Phe |
| F | H | H | Et | Et | Bu | H | 2,4,6-tri-F-Phe |
| F | H | H | Et | Et | Bu | H | 2-Me-6-tBu-Phe |
| F | H | H | Et | Et | Bu | H | 2,4,6-tri-MeO-Phe |
| F | H | H | Et | Et | Bu | H | 2,6-bis-MeS-4-Me-Phe |
| F | H | H | Et | Et | Bu | H | 2-tBu-5-(CH₂-Imd)-Phe |
| MeO | Me | Me | Et | Et | Bu | H | 2,6-di-iPr-Phe |
| MeO | Et | Et | Et | Et | Bu | H | 2,6-di-iPr-Phe |
| MeO | H | H | Et | Et | Me | H | 2,6-di-iPr-Phe |
| MeO | H | H | Et | Et | Et | H | 2,6-di-iPr-Phe |
| MeO | H | H | Et | Et | Pr | H | 2,6-di-iPr-Phe |
| MeO | H | H | Et | Et | iPr | H | 2,6-di-iPr-Phe |

TABLE 12

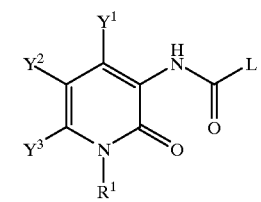

| Y¹ | Y² | Y³ | R¹ | L |
|---|---|---|---|---|
| Me | H | H | Bu | C(CH₃)₂(CH₂)₉CH₃ |
| Et | H | H | Bu | C(CH₃)₂(CH₂)₉CH₃ |

TABLE 12-continued

| Y¹ | Y² | Y³ | R¹ | L |
|---|---|---|---|---|
| Pr | H | H | Bu | C(CH₃)₂(CH₂)₉CH₃ |
| iPr | H | H | Bu | C(CH₃)₂(CH₂)₉CH₃ |
| Bu | H | H | Bu | C(CH₃)₂(CH₂)₉CH₃ |
| (CH₂)₉CH₃ | H | H | Bu | C(CH₃)₂(CH₂)₉CH₃ |
| (CH₂)₁₀CH₃ | H | H | Bu | C(CH₃)₂(CH₂)₉CH₃ |
| (CH₂)₁₄CH₃ | H | H | Bu | C(OH₃)₂(CH₂)₉CH₃ |
| Ph | H | H | Bu | C(CH₃)₂(CH₂)₉CH₃ |
| 2-Py | H | H | Bu | C(CH₃)₂(CH₂)₉CH₃ |
| 3-Py | H | H | Bu | C(CH₃)₂(CH₂)₉CH₃ |
| 4-Py | H | H | Bu | C(CH₃)₂(CH₂)₉CH₃ |
| H | Ph | H | Bu | C(CH₃)₂(CH₂)₉CH₃ |
| H | H | Ph | Bu | C(CH₃)₂(CH₂)₉CH₃ |
| H | H | Ph | H | C(CH₃)₂(CH₂)₉CH₃ |
| H | H | Ph | Me | C(CH₃)₂(CH₂)₉CH₃ |
| H | H | Ph | Et | C(CH₃)₂(CH₂)₉CH₃ |
| H | H | Ph | Pr | C(CH₃)₂(CH₂)₉CH₃ |
| H | H | Ph | iPr | C(CH₃)₂(CH₂)₉CH₃ |
| 3-MeO-Ph | H | H | H | C(CH₃)₂(CH₂)₉CH₃ |
| 3-MeO-Ph | H | H | Me | C(CH₃)₂(CH₂)₉CH₃ |
| 3-MeO-Ph | H | H | Et | C(CH₃)₂(CH₂)₉CH₃ |
| 3-MeO-Ph | H | H | Pr | C(CH₃)₂(CH₂)₉CH₃ |
| 3-MeO-Ph | H | H | iPr | C(CH₃)₂(CH₂)₉CH₃ |
| 3-MeO-Ph | H | H | Bu | C(CH₃)₂(CH₂)₉CH₃ |
| 3-MeO-Ph | H | H | Bu | (CH₂)₃CH₃ |
| 3-MeO-Ph | H | H | Bu | (CH₂)₉CH₃ |
| 3-MeO-Ph | H | H | Bu | (CH₂)₁₉CH₃ |
| 3-MeO-Ph | H | H | Bu | Ph |

EXAMPLES

The present invention is illustrated by Examples, but should not be construed to be limited thereto.

Example 1

Preparation of N-[1-butyl-4-(3-methoxyphenyl)-1,2-dihydro-2-oxo-1,8-naphthyridin-3-yl]-N'-(2,6-diisopropylphenyl)urea:

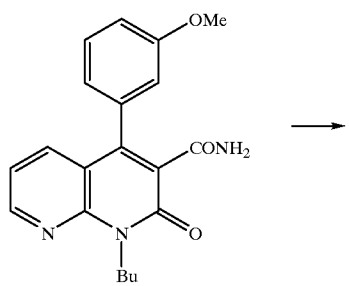

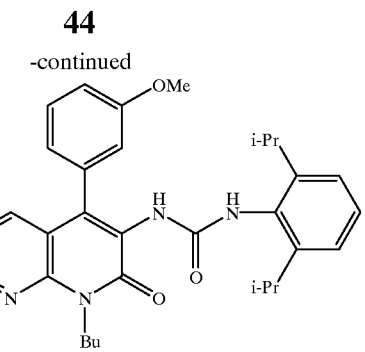

To a suspension of 1-butyl-3-carbamoyl-4-(3-methoxyphenyl)-1,2-dihydro-2-oxo-1,8-naphthyridine (10.0 g, 27.2 mmol) in N,N-dimethylformamide (100 ml) was added lead tetracetate (14.5 g, 32.6 mmol), and the mixture was stirred at room temperature for 0.5 hour. Subsequently, to the mixture was added 2,6-diisopropylaniline (5.3 g, 30 mmol) at the same temperature, and the mixture was stirred at 40° C.–50° C. for 1.5 hour. After allowed to cool, ethyl acetate (500 ml) was added to the mixture, and the mixture was filtered through a celite pad. The filtrate was washed successively with water, 4N aqueous hydrochloric acid solution, water and a saturated aqueous sodium chloride solution, dried over magnesium sulfate, and concentrated under reduced pressure to the volume of about 100 ml. The resultant was stirred for 2 hours under cooling with ice-water, and the precipitated crystals were collected by filtration to give the title compound (9.81 g, 18.6 mmol, 68%) as colorless crystals.

M.p. 179–182° C.;

Example 2

Preparation of N-[1-butyl-4-(3-methoxyphenyl)-1,2-dihydro-2-oxo-1,8-naphthyridin-3-yl]-N'-(2,6-diisopropylphenyl)urea:

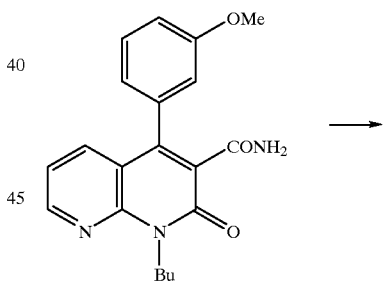

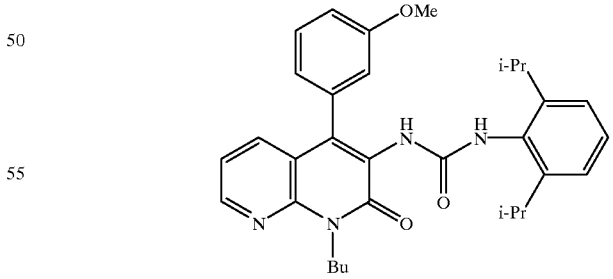

To a 1N aqueuos sodium hydroxide solution (48 ml, 48 mmol) was added dropwise bromine (1.2 ml, 24 mmol) under ice-cooling, and the mixture was stirred for 30 minutes. The pale yellow solution thus obtained was added dropwise to a suspension of 1-butyl-3-carbamoyl-4-(3-methoxyphenyl)-1,2-dihydro-2-oxo-1,8-naphthyridine (2.1 g, 6 mmol) and tetrabutylammonium hydrogen sulfate (102 mg, 0.3 mmol) in toluene (210 ml) at room temperature, and the mixture was stirred at the same temperature for 4 hours. To the mixture was added a solution of acetic acid (35 ml) and 2,6-diisopropylaniline (1.6 g, 9.0 mmol) in toluene (35 ml) at room temperature, and the mixture was stirred at the same temperature for 1.5 hour. Water was added to the reaction solution, and the mixture was extracted with ethyl acetate, washed with water, washed with a saturated aqueous sodium chloride solution, and dried over anhydrous magnesium sulfate. The residue was concentrated under reduced pressure, and purified by silica gel column chromatography (ethyl acetate/hexane=1/10 to ½) to give the title compound (2.34 g, 4.44 mmol, 74%) as a colorless solid.

M.p. 178–181° C.;

Example 3

Preparation of 1-butyl-3-amino-4-(3-methoxyphenyl)-1,2-dihydro-2-oxo-1,8-naphthyridine:

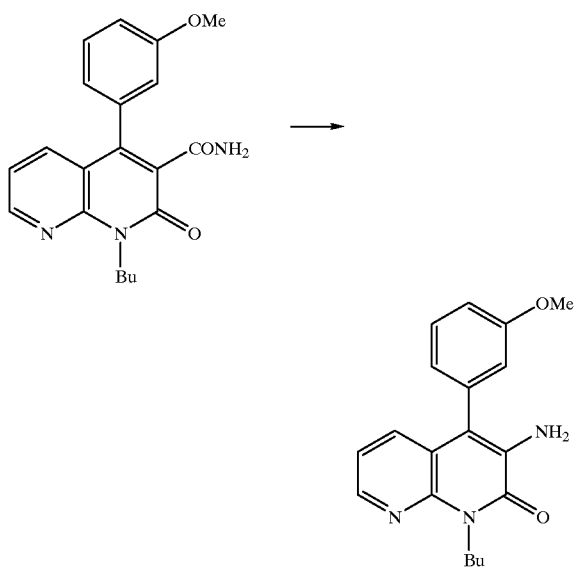

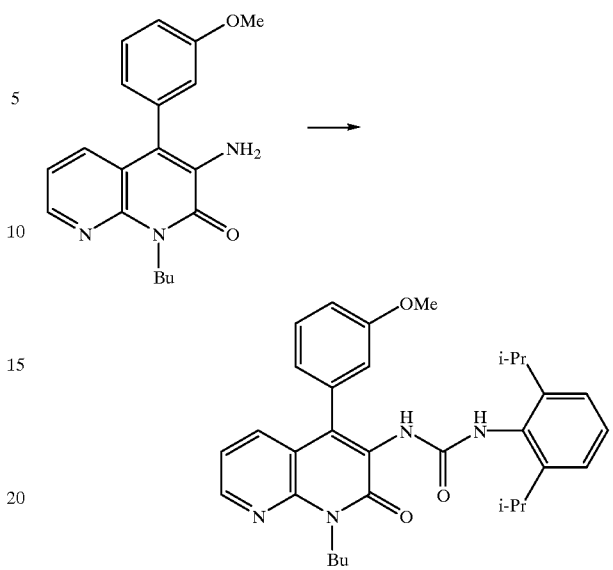

To a 1N aqueous sodium hydroxide solution (88 ml, 88 mmol) was added dropwise bromine (1.0 ml, 19.4 mmol) under ice-cooling, and the mixture was stirred for 30 minutes. The pale yellow solution thus obtained was added dropwise to a suspension of 1-butyl-3-carbamoyl-4-(3-methoxyphenyl)-1,2-dihydro-2-oxo-1,8-naphthyridine (5.0 g, 14.2 ml) and tetrabutylammonium hydrogen sulfate (250 mg. 0.71 mmol) in tetrahydrofuran (500 ml) at room temperature, and the mixture was stirred at the same temperature for 6.5 hours. Water was added to the reaction solution, and the mixture was extracted with ethyl acetate, washed with water, washed with a saturated aqueous sodium chloride solution, dried over anhydrous magnesium sulfate, and concentrated under reduced pressure. To the concentrated residue was added 2-propanol (40 ml), and the mixture was stirred for 3 hours under ice-cooling. The precipitated solid was collected by filtration to give the title compound (3.49 g, 10.8 mmol, 76%) as pale yellow powder.

M.p. 138–141° C.;

Example 4

Preparation of N-[1-butyl-4-(3-methoxyphenyl)-1,2-dihydro-2-oxo-1,8-naphthyridin-3-yl]-N'-(2,6-diisopropylphenyl)urea:

To a solution of 3-amino-1-butyl-4-(3-methoxyphenyl)-1,2-dihydro-2-oxo-1,8-naphthyridine (1.70 g, 5.26 mmol) in tetrahydrofuran (14 ml) was added phenyl chlorocarbonate (1.32 ml, 10.5 ml), and the mixture was stirred at 40–50° C. for 3 hours. The mixture was allowed to cool, and thereto was added water, and the mixture was extracted with water. The extract was washed with a 5% aqueous sodium chloride solution, dried over anhydrous magnesium sulfate, and concentrated under reduced pressure. The resulting residue was dissolved in dimethylformamide (10 ml), and thereto was added a solution of 2,6-diisopropylaniline (1.24 g, 6.31 mmol) and dimethylformamide (5 ml) and 4-dimethylaminopyridine (0.62 g, 5.26 mmol), and the mixture was stirred at room temperature for one hour. To the reaction solution was added water, and the mixture was extracted with ethyl acetate. The extract was washed successively with a 5% aqueous sodium hydrogen carbonate solution and a 5% aqueous sodium chloride solution, dried over anhydrous magnesium sulfate, and concentrated under reduced pressure. The residue was crystallized from ethyl acetate to give the title compound (1.75 g, 3.32 mmol) as colorless crystals.

M.p. 179–182° C.;

Example 5

Preparation of 1-butyl-3-phthalimide-4-(3-methoxyphenyl)-1,2-dihydro-2-oxo-1,8-naphthyridine:

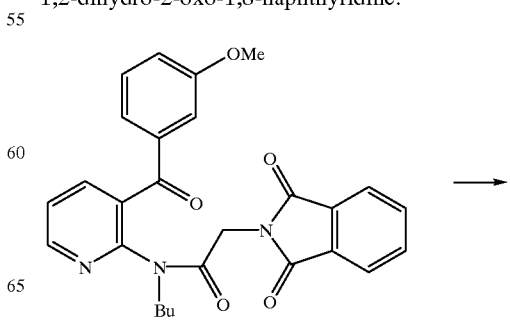

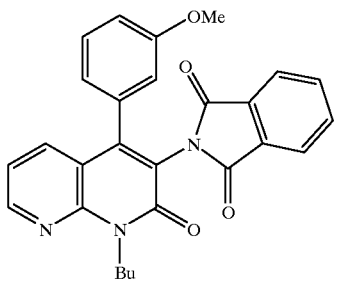

To a solution of 1-{(N-butyl-N-phthalimidacetyl)amino}-3-(3-methoxybenzoyl)pyridine (3.44 g, 7.30 mmol) in N,N-dimethylformamide (18 ml) was added potassium carbonate (6.05 g, 43.8 mmol), and the mixture was stirred at 90–100° C. for 3 hours. The mixture was cooled to room temperature, and water was added thereto, and the mixture was extracted with ethyl acetate. The extract was washed successively with a 5% aqueous sodium hydrogen carbonate solution and a 5% aqueous sodium chloride solution, dried over anhydrous magnesium sulfate, and concentrated under reduced pressure to give the title compound (2.15 g, 4.74 mmol, 65%) as brown crystals, which were used in the subsequent reaction without further purification.

$^1$H NMR δ (CDCl$_3$) 0.91 (3H, t, J=7.3 Hz), 1.38–1.45 (2H, m), 1.68–1.79 (2H, m), 3.66 (3H, s), 4.52 (2H, t, J=7.3 Hz), 6.81–6.88 (3H, m), 7.07 (1H, dd, J=8.1 Hz, 4.8 Hz), 7.22 (1H, ddd, J=7.5 Hz, 7.5 Hz, 3.3 Hz), 7.58–7.63 (3H, m), 7.70–7.76 (2H, m), 8.60 (1H, dd, J=4.8 Hz, 1.7 Hz)

Example 6

Preparation of 1-butyl-3-amino-4-(3-methoxyphenyl)-1,2-dihydro-2-oxo-1,8-naphthyridine:

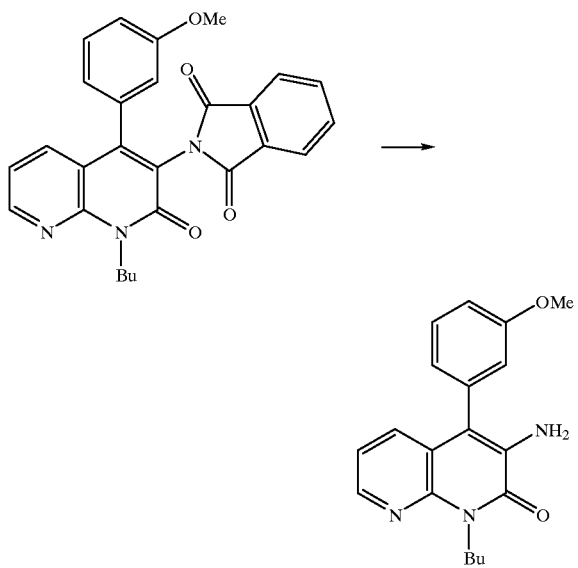

To a solution of 1-butyl-3-phthalimide-4-(3-methoxyphenyl)-1,2-dihydro-2-oxo-1,8-naphthyridine (2.15 g, 4.74 mmol) in ethanol (16 ml) was added a 30% solution of methylamine in ethanol (4 ml), and the mixture was stirred at room temperature for 5 hours. The mixture was concentrated under reduced pressure, and the residue was dissolved in ethyl acetate. The mixture was washed successively with a 5% aqueous sodium hydrogen carbonate solution and a 5% aqueous sodium chloride solution, dried over anhydrous magnesium sulfate, and concentrated under reduced pressure. The residue was purified by silica gel column chromatography (ethyl acetate/hexane=1/10 to 1/4) to give the title compound (0.78 g, 2.43 mmol, 51%) as colorless crystals.

$^1$H NMR δ (CDCl$_3$) 1.01 (3H, t, J=7.3 Hz), 1.44–1.54 (2H, m), 1.76–1.86 (2H, m), 3.84 (3H, s), 4.49 (2H, brs), 4.66 (2H, t, J=7.5 Hz), 6.87–7.04 (4H, m), 7.42–7.50 (2H, m), 8.35 (1H, dd, J=4.6 Hz, 1.8 Hz)

Example 7

Preparation of 1-butyl-3-amino-4-(3-methoxyphenyl)-1,2-dihydro-2-oxo-1,8-naphthyridine:

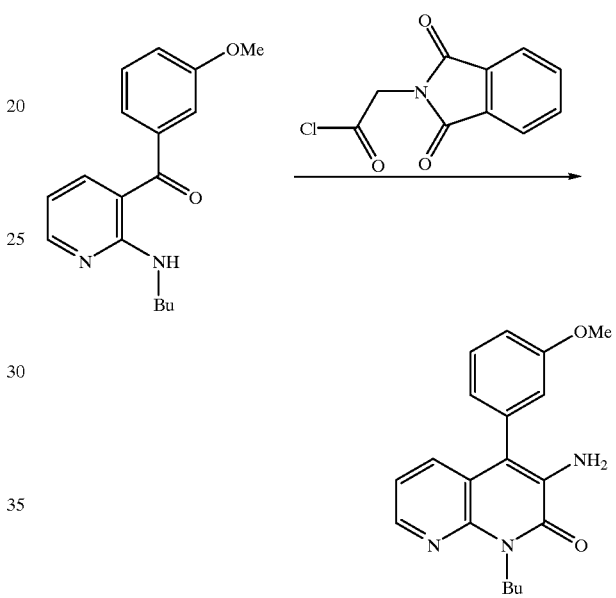

To a suspension of N-phthaloylglycine (4.76 g, 23.2 mmol) in toluene (24 ml) were added thionyl chloride (5.08 ml, 69.6 mmol) and dimethylformamide (0.4 ml), and the mixture was stirred at 50–60° C. for 30 minutes, cooled, and concentrated under reduced pressure to remove the solvent. To the resulting solid was added toluene (12 ml), and further thereto were added a solution of 2-(butylamino)-3-(3-methoxybenzoyl)pyridine (3.30 g, 11.6 mmol) in toluene (15 ml) and pyridine (27 ml), and the mixture was stirred at 80–90° C. for 2 hours. After allowed to cool, to the mixture were added potassium carbonate (9.62 g, 69.6 mmol) and N,N-dimethylformamide (54 ml), and the mixture was further stirred at 90–100° C. for 8 hours. After allowed to cool, a 40% aqueous methylamine solution (4.99 ml, 58.0 mmol) was added, and the mixture was stirred at room temperature for one hour. Water was added to the reaction solution, and the mixture was extracted with toluene. The extract was washed successively with 1N hydrochloric acid, water, a 5% aqueous sodium hydrogen carbonate solution and a 5% aqueous sodium chloride solution, dried over anhydrous magnesium sulfate, and concentrated under reduced pressure. The resulting solid was recrytallized from 2-propanol to give the title compound (2.30 g, 7.11 mmol, 61%) as colorless prisms.

M.p. 140–142° C.;

Example 8

Preparation of N-{1-butyl-2-oxo-4-(3-methoxy)phenyl-1,2-dihydro-pyridin-3-yl}-N'-(2,6-diisopropylphenyl)urea:

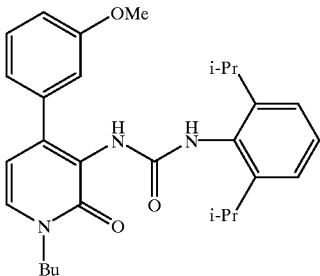

To a solution of 1-butyl-2-oxo-4-(3-methoxy)phenyl-1,2-dihydropyridine-3-carboxylic acid (4.61 g, 15.3 mmol) in DMF (dimethyformamide; 50 ml) were added DPPA (diphenylphosphoryl azide; 5.06 g, 18.4 mmol) and triethylamine (2.7 ml), and the mixture was stirred at about 50° C. for one hour. To the mixture was added 2,6-diisopropylaniline (3.26 g, 18.4 mmol), and the mixture was stirred at about 70° C. for 4.5 hours. To the reaction solution was added water, and the mixture was extracted with ethyl acetate, washed with a saturated aqueous sodium chloride solution, and dried over anhydrous magnesium sulfate. The solvent was distilled off, and the resulting residue was purified by silica gel column chromatography (ethyl acetate:hexane=1:1) to give the title compound (6.51 g, yield; 90%) as white crystals.

M.p. 176–178° C.; IR (KBr) 3324, 3068, 1703, 1643, 1565 cm$^{-1}$.

Example 9

Preparation of N-{1-butyl-2-oxo-4-(3-hydroxy)phenyl-1,2-dihydropyridin-3-yl}-N'-(2,6-diisopropylphenyl)urea:

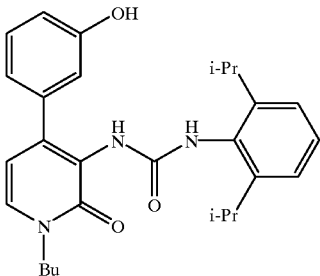

To a solution of N-{1-butyl-2-oxo-4-(3-methoxy)phenyl-1,2-dihydropyridin-3-y}-N'-(2,6-dihydropropylphenyl)urea (3.84 g, 8.07 mmol) in methylene chloride (100 ml) was added BBr$_3$ (boron tribromide; 3.1 ml, 32.3 mmol), and the mixture was stirred at room temperature for 2 hours. Water was added to the reaction solution, and basified with a saturated aqueous sodium hydrogen carbonate solution. The mixture was extracted with ethyl acetate, washed with a saturated aqueous sodium chloride solution, and dried over magnesium sulfate. The solvent was evaporated under reduced pressure, and the resulting crystals were collected by filtration to give the title compound (3.61 g, yield; 97%) as white crystals.

M.p. 188–191° C.

Example 10

Preparation of N-[1-butyl-2-oxo-4-[3-{3-(1,2,4-triazol-1-yl)propoxy}-phenyl]-1,2-dihydropyridin-3-yl]-N'-(2,6-diisopropylphenyl)urea:

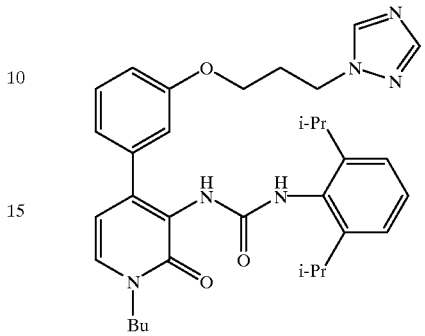

To a solution of N-{1-butyl-2-oxo-4-(3-hydroxy)phenyl-1,2-dihydropyridin-3-yl}-N'-(2,6-diisopropylphenyl)urea (500 mg, 1.08 mmol) in DMF (5 ml) were added potassium carbonate (4.48 g, 32.4 mmol), 1-(3-bromopropyl)-1,2,4-triazole (247 mg, 1.30 mmol), and sodium iodide (81 mg, 0.54 mmol), and the mixture was stirred at about 50° C. for 9 hours. Potassium carbonate was removed by filtration, and water was added to the filtrate, and extracted with ethyl acetate. The extract was washed with a saturated aqueous sodium chloride solution, and dried over magnesium sulfate. The solvent was evaporated under reduced pressure, and the resulting residue was purified by silica gel column chromatography (ethyl acetate) to give the title compound (420 mg, yield; 68%) as pale yellow amorphous.

$^1$H NMR δ (DMSO-d$_6$) 0.94 (t, J=7.2 Hz, 3H), 1.00 (bs, 12H), 1.28–1.41 (m, 2H), 1.63–1.71 (m, 2H), 2.15–2.26 (m, 2H), 2.88–2.91 (m, 2H), 3.94–3.99 (m, 4H), 4.35 (t, J=7.0 Hz, 2H), 6.23 (d, J=7.2 Hz, 1H), 6.86 (d J=7.9H, 1H), 6.99–7.07 (m, 4H), 7.13 (dd, J=7.9, 7.9 Hz, 1H), 7.26 (dd, J=7.9, 7.9 Hz, 1H), 7.54 (d, J=7.2 Hz, 1H), 7.77 (s, 1H), 7.81 (s, 1H), 7.96 (s, 1H), 8.52 (s, 1H); IR (KBr) 3321, 1706, 1645, 1584 cm$^{-1}$.

Preparation of the hydrochloride thereof:

To a solution of N-[1-butyl-2-oxo-4-[3-{3-(1,2,4-triazol-1-yl)-propoxy}phenyl]-1,2-dihydropyridin-3-yl]-N'-(2,6-diisopropylphenyl)urea (330 mg, 0.578 mmol) in THF (tetrahydrofuran; 5 ml) was added 1 N slution of hydrochoric acid in ether (1.7 ml), and the mixture was stirred. The solvent was evaporated under reduced pressure, and to the residue was added ether. The precipitated crystals were collected by filtration, and dried to give the hydrochloride of the title compound (305 mg, 87%) as pale yellow crystals.

M.p. 90–95° C.; IR (KBr) 3262, 1645, 1600 cm$^{-1}$.

Example 11

Preparation of N-[1-butyl-2-oxo-4-{3-(3-pyridylmethoxy)phenyl}-1,2-dihydropyridin-3-yl]-N'-(2,6-diisopropylphenyl)urea

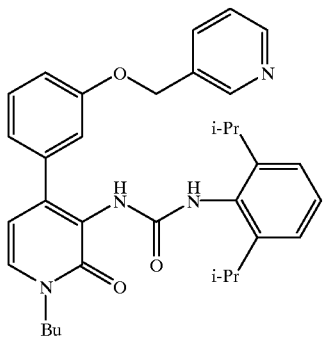

The title compound was obtained in the same manner as in Example 10 from N-{1-butyl-2-oxo-4-(3-hydroxy)phenyl)-1,2-dihydropyridin-3-yl}-N'-(2,6-diisopropylphenyl)urea and 3-chloromethylpyridine hydrochloride.

$^1$H NMR δ (CD$_3$OD) 0.99 (t, J=7.3 Hz, 3H), 1.05 (bs, 12H), 1.39–1.44 (m, 2H), 1.75–1.78 (m, 2H), 2.99 (m, 2H), 4.05 (t, J=7.50 Hz, 2H), 5.18 (s, 2H), 6.37 (d, J=7.0 Hz, 1H), 7.04–7.06 (m, 3H), 7.14–7.21 (m, 3H), 7.36 (dd, J=7.9, 7.9 Hz, 1H), 7.44–7.52 (m, 2H), 7.76 (d, J=7.0 Hz, 1H), 8.50 (d, J=4.8 Hz, 1H), 8.64 (s, 1H).

The hydrochloride of the title compound was obtained in the same manner as in Example 10.

M.p. 98–100° C.; IR (KBr) 3152, 1646, 1583 cm$^{-1}$.

Example 12

Preparation of N-[1-butyl-2-oxo-4-[3-(2-diethylaminoethoxy)phenyl}-1,2-dihydropyridin-3-yl]-N'-(2,6-diisopropylphenyl)urea

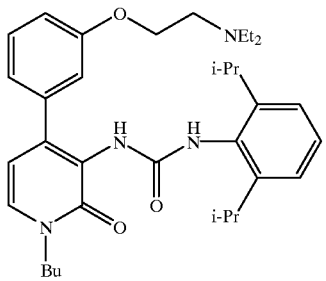

The title compound was obtained in the same manner as in Example 10 from N-{1-butyl-2-oxo-4-(3-hydroxy)phenyl-1,2-dihydropyridin-3-yl}-N'-(2,6-diisopropylphenyl) urea and N,N-diethylamino ethyl chloride hydrochloride.

$^1$H NMR δ (DMSO-d$_6$) 0.91–1.06 (m, 21H), 1.29–1.38 (m, 2H), 1.63–1.71 (m, 2H), 2.57 (bs, 2H), 2.81 (bs, 2H), 2.88–2.97 (m, 2H), 2.88–2.91 (m, 2H), 3.94–4.03 (m, 6H), 6.23 (d, J=7.2 Hz, 1H), 6.87 (d, J=8.1 Hz, 1H), 7.00–7.03 (m, 4H), 7.13 (dd, J=7.7, 7.7 Hz, 1H), 7.26 (dd, J=8.1, 8.1H, 1H), 7.53 (d, J=7.2 Hz, 1H), 7.77 (s, 1H), 7.82 (s, 1H).

The hydrochloride of the title compound was obtained in the same manner as in Example 10.

M.p. 125–130° C.; IR (KBr) 3272, 1692, 1646, 1601 cm$^{-1}$.

Example 13

Preparation of N-{1-butyl-2-oxo-4-(3-bromo)phenyl-1,2-dihydropyridin-3-yl}-N'-(2,6-diisopropylphenyl)urea

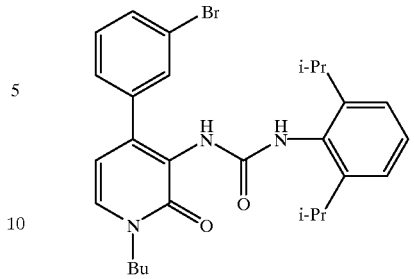

The title compound was obtained in the same manner as in Example 8 from 1-butyl-2-oxo-4-(3-bromo)phenyl-1,2-dihydropyridin-3-carboxylic acid and 2,6-diisopropylaniline.

M.p. 169–172° C.; IR (KBr) 3314, 1710, 1645, 1586 cm$^{-1}$.

Example 14.

Preparation of N-[1-butyl-2-oxo-4-[3-{3-(diethylamino)-1-propynyl}-phenyl]-1,2-dihydropyridin-3-yl]-N'-(2,6-diisopropylphenyl)urea:

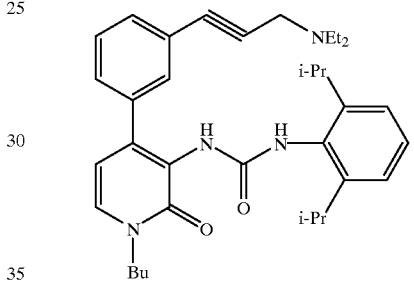

To a solution of N-{1-butyl-2-oxo-4-(3-bromo)phenyl-1,2-dihydropyridin-3-yl}-N'-(2,6-diisopropylphenyl)urea (1.23 g, 2.35 mmol) in DMF (6 ml) were added N,N-diethylpropargylamine (784 mg), triphenylphosphine (100 mg, 0.376 mmol), copper iodide (36 mg, 0.188 mmol), triethylamine (2.0 ml), and 10% palladium on active carbon (100 mg, 0.094 mmol), and the mixture was stirred at about 80° C. for 13 hours. The mixture was filtered through a cerite pad, and the filtrate was diluted with ethyl acetate, washed with a saturated aqueous sodium chloride solution and dried over magnesium sulfate. The solvent was evaporated under reduced pressure, and the residue was purified by silica gel column chromatography (chloroform:methanol=30:1) to give the title compound (813 mg, yield; 62%).

M.p. 76–82° C.; IR (KBr) 3323, 1709, 1645, 1584 cm$^{-1}$.
Preparation of the hydrochloride thereof:

To a solution of N-[1-butyl-2-oxo-4-[3-{3-(diethylamino)-1-propynyl}phenyl]-1,2-dihydropyridin-3-yl]-N'-(2,6-diisopropylphenyl)urea (393 mg, 0.707 mmol) in THF (5 ml) was added 1N solution of hydrochoric acid in ether (2.1 ml), and the mixture was stirred. The solvent was evaporated under reduced pressure, and to the residue was added hexane. The precipitated crystals were collected by filtration, and dried to give the hydrochloride of the title compound (414 mg, yield; 99%) as brown crystals.

$^1$H NMR δ (CD$_3$OD) 0.99 (t, J=7.5 Hz, 3H), 1.06 (bd, 12H), 1.38 (t, J=7.2 Hz, 6H), 1.38–1.46 (m, 2H), 1.73–1.83 (m, 2H), 2.84–2.93 (m, 2H), 3.37 (q, J=7.2 Hz, 4H), 4.06 (t, J=7.5 Hz, 2H), 4.36 (s, 2H), 6.34 (d, J=7.0 Hz, 1H), 7.05 (d, J=7.3 Hz, 2H), 7.16 (dd, J=6.8, 6.8 Hz, 1H), 7.45 (dd, J=7.5, 7.5 Hz, 1H), 7.52–7.65 (m, 4H).

Example 15

Preparation of N-{1-butyl-2-oxo-4-(3-bromo)phenyl-5-methyl-1,2-dihydropyridin-3-yl}-N'-(2,6-diisopropylphenyl)urea:

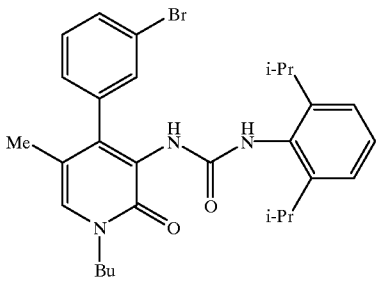

The title compound was obtained in the same manner as in Example 8 from 1-butyl-2-oxo-4-(3-bromo)phenyl-5-methyl-1,2-dihydropyridin-3-carboxylic acid and 2,6-diisopropylaniline.

M.p. 199–200° C.; IR (KBr) 3315, 3266, 3226, 1719, 1650, 1575 cm$^{-1}$.

Example 16

Preparation of N-[1-butyl-2-oxo-4-[3-{3-(diethylamino)-1-propynyl}-phenyl]-5-methyl-1,2-dihydropyridin-3-yl]-N'-(2,6-diisopropylphenyl)urea:

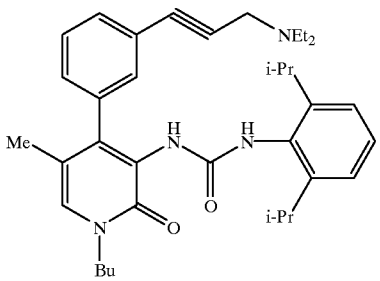

The title compound was obtained in the same manner as in Example 14 from N-{1-butyl-2-oxo-4-(3-bromo)phenyl-5-methyl-1,2-dihydropyridin-3-yl}-N'-(2,6-diisopropylphenyl)urea and N,N-diethylpropargylamine.

$^1$H NMR δ (CD$_3$OD) 0.99 (t, J=7.3 Hz, 6H), 1.07–1.15 (m, 15H), 1.35–1.47 (m, 2H), 1.73–1.80 (m, 2H), 1.84 (s, 3H), 2.67 (q, J=7.3 Hz, 4H), 2.83 (bs, 2H), 3.67 (s, 2H), 4.03 (t, J=7.3 Hz, 2H), 7.05 (d, J=7.3 Hz, 2H), 7.16 (dd, J=7.3, 7.3 Hz, 1H), 7.24–7.31 (m, 2H), 7.38–7.46 (m, 3H).

The hydrochloride of the title compound was obtained in the same manner as in Example 10.

M.p. 159–162° C.; IR (KBr) 3320, 2236, 1654, 1574 cm$^{-1}$.

Example 17

Preparation of N-{1-butyl-2-oxo-4-(5-bromo-2-methoxy)phenyl-1,2-dihydropyridin-3-yl}-N'-(2,6-diisopropylphenyl)urea:

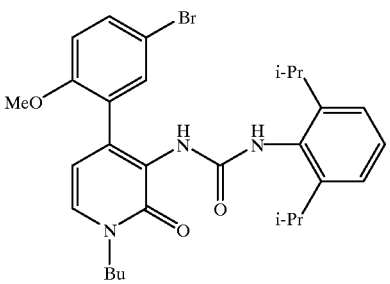

The title compound was obtained in the same manner as in Example 8 from 1-butyl-2-oxo-4-(5-bromo-2-methoxy)phenyl-1,2-dihydropyridin-3-carboxylic acid and 2,6-diisopropylaniline.

M.p. 179–181° C.; IR (KBr) 3322, 1671, 1645, 1584 cm$^{-1}$.

Example 18

Preparation of N-[1-butyl-2-oxo-4-[5-{3-(diethylamino)-1-propynyl}-2-methoxy]phenyl-5-methyl-1,2-dihydropyridin-3-yl]-N'-(2,6-diisopropylphenyl)urea:

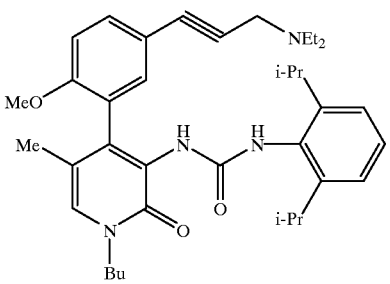

The title compound was obtained in the same manner as in Example 14 from N-{1-butyl-2-oxo-4-(5-bromo-2-methoxy)phenyl-5-methyl-1,2-dihydropyridin-3-yl}-N'-(2,6-diisopropylphenyl)urea and N,N-diethylpropargylamine.

$^1$H NMR δ (CD$_3$OD) 0.96 (t, J=7.3 Hz, 3H), 0.98–1.13 (m, 18H), 1.33–1.46 (m, 2H), 1.69–1.79 (m, 2H), 2.66 (q, J=7.2 Hz, 4H), 2.81–2.90 (m, 2H), 2.81–2.90 (m, 2H), 3.64 (s, 2H), 3.82 (s, 3H), 4.01 (t, J=7.2 Hz, 2H), 6.27 (d, J=7.2 Hz, 1H), 7.02–7.05 (m, 3H), 7.14 (dd, J=7.0, 7.0 Hz, 1H), 7.33 (d, J=1.8 Hz, 1H), 7.42–7.45 (m, 2H).

The hydrochloride of the title compound was obtained in the same manner as in Example 10.

M.p. 208–210° C.; IR (KBr) 3437, 2232, 1646, 1599 cm$^{-1}$.

Example 19

Preparation of N-{1-butyl-2-oxo-4-(2,5-dimethoxy)phenyl-1,2-dihydropyridin-3-yl}-N'-(2,6-diisopropylphenyl)urea:

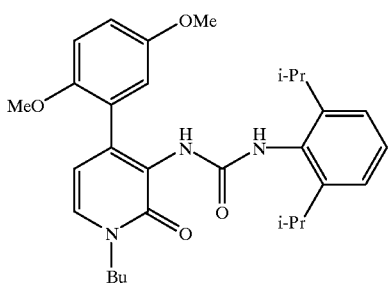

The title compound was obtained in the same manner as in Example 8 from 1-butyl-2-oxo-4-(2,5-dimethoxy)phenyl-1,2-dihydropyridin-3-carboxylic acid and 2,6-diisopropylaniline.

M.p. 165–167° C.

Example 20

Preparation of N-{1-butyl-2-oxo-4-(2,5-dimethoxy)phenyl-1,2-dihydropyridin-3-yl}-N'-{2,4-bis(methylthio)-6-methylpyridin-3-yl}urea:

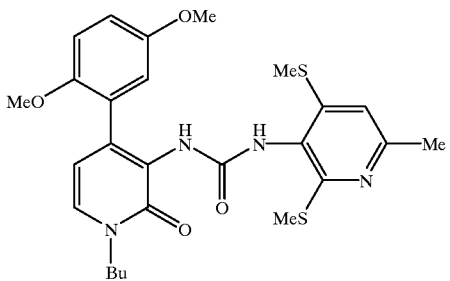

The title compound was obtained in the same manner as in Example 8 from 1-butyl-2-oxo-4-(2,5-dimethoxy)phenyl-1,2-dihydropyridin-3-carboxylic acid and 3-amino-2,4-bis(methylthio)-6-methylpyridine.

M.p. 193–197° C. (decomposed)

$^1$H NMR δ (DMSO-$d_6$) 0.94 (t, J=7.5 Hz, 3H), 1.34 (tq, J=7.5, 7.5 Hz, 2H), 1.67 (tt, J=7.5, 7.5 Hz, 2H), 2.30 (s, 3H), 2.39 (s, 3H), 3.68 (s, 6H), 3.93 (t, J=7.5 Hz, 2H), 6.13 (d, J=7.2 Hz, 1H), 6.76–6.83 (m, 3H), 6.92 (d, J=8.8 Hz, 1H), 7.45 (d, J=7.2 Hz, 1H), 7.70 (bs, 1H), 7.90 (bs, 1H).

Example 21

Preparation of N-{1-butyl-2-oxo-4-(2-methoxy-5-bromo)phenyl-1,2-dihydropyridin-3-yl}-N'-{2,4-bis(methylthio)-6-methylpyridin-3-yl}urea:

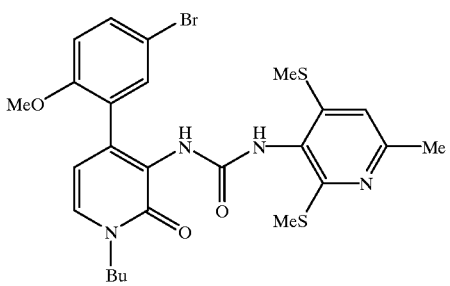

The title compound was obtained in the same manner as in Example 8 from 1-butyl-2-oxo-4-(2-methoxy-5-bromo)phenyl-1,2-dihydropyridin-3-carboxylic acid and 3-amino-2,4-bis(methylthio)-6-methylpyridine.

$^1$H NMR δ (DMSO-$d_6$) 0.94 (t, J=7.2 Hz, 3H), 1.33–1.35 (m, 2H), 1.67 (m, 2H), 2.32 (s, 6H), 2.39 (s, 3H), 3.72 (s, 3H), 3.94 (bs, 2H), 6.11 (d, J=6.8 Hz, 1H), 6.76 (s, 1H), 6.96 (d, J=6.8 Hz, 1H), 7.24 (s, 1H), 7.38 (d, J=8.8 Hz, 1H), 7.43 (d, J=8.8 Hz, 1H), 7.87 (s, 1H), 8.00 (s, 1H).

Example 22

Preparation of N-{1-butyl-2-oxo-4-(2,5-dimethoxy)phenyl-1,2-dihydropyridin-3-yl}-N'-(2-tert-butyl-5-morpholinomethylphenyl)urea:

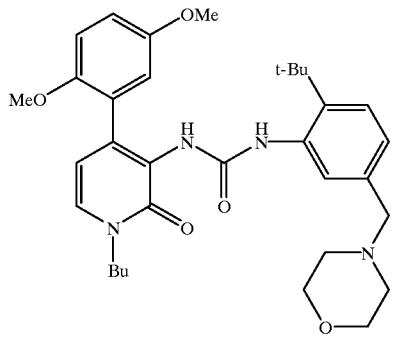

The title compound was obtained in the same manner as in Example 8 from 1-butyl-2-oxo-4-(2,5-dimethoxy)phenyl-1,2-dihydropyridin-3-carboxylic acid and 2-tert-butyl-5-morpholinomethylaniline.

$^1$H NMR δ (DMSO-$d_6$) 0.94 (t, J=7.2 Hz, 3H), 1.21 (s, 9H), 1.36 (tq, J=7.2, 7.2 Hz, 2H), 1.69 (tt, J=7.2, 7.2 Hz, 2H), 2.30 (bs, 4H), 3.30 (s, 2H), 3.54 (bs, 4H), 3.66 (s, 6H), 3.94 (t, J=7.2 Hz, 2H), 6.15 (d, J=7.2 Hz, 1H), 6.77 (d, J=3.1 Hz, 1H), 6.82 (dd, J=3.1, 8.3 Hz, 1H), 6.88 (s, 1H), 6.94 (d, J=9.0 Hz, 1H), 6.97 (d, J=9.0 Hz, 1H), 7.48 (d, J=7.2 Hz, 1H), 7.59 (s, 1H), 7.84 (s, 1H).

The hydrochloride of the title compound was obtained in the same manner as in Example 10.

M.p. 157–162° C. (decomposed).

Example 23

Preparation of N-{1-butyl-2-oxo-4-(2-methoxy-5-benzyloxy)phenyl-1,2-dihydropyridin-3-yl}-N'-(2,6-diisopropylphenyl) urea:

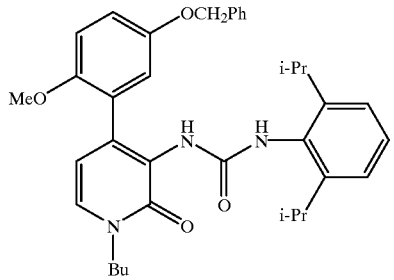

The title compound was obtained in the same manner as in Example 8 from 1-butyl-2-oxo-4-(2-methoxy-5-benzyloxy)phenyl-1,2-dihydropyridin-3-carboxylic acid and 2,6-diisopropylaniline.

$^1$H NMR δ (DMSO-$d_6$) 0.94 (t, J=7.3 Hz, 3H), 1.35 (tq, J=7.3, 7.3 Hz, 2H), 1.66–1.68 (m, 2H), 2.83–2.89 (m, 2H), 3.69 (s, 3H), 3.94 (t, J=7.3 Hz, 2H), 4.99 (s, 2H), 6.13 (d, J=7.2 Hz, 1H), 6.88 (s, 1H), 6.91–6.95 (m, 2H), 7.01 (d, J=7.7 Hz, 2H), 7.13 (dd, J=7.7, 7.7 Hz, 1H), 7.31–7.46 (m, 6H), 7.69 (s, 1H), 7.82 (s, 1H).

Example 24
Preparation of N-{1-butyl-2-oxo-4-(2-hydroxy-5-bromo)phenyl-1,2-dihydropyridin-3-yl}-N'-(2,6-diisopropylphenyl)urea:

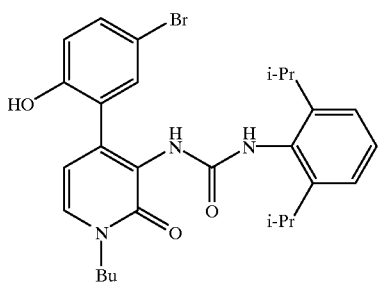

To a solution of N-{1-butyl-2-oxo-4-(2-methoxy-5-bromo)phenyl-1,2-dihydropyridin-3-yl}-N'-(2,6-diisopropylphenyl) urea (1.00 g, 1.80 mmol) in methylene chloride (10 ml) was added BBr$_3$ (0.51 ml, 5.40 mmol) under ice-cooling, and the mixture was stirred under reflux for 3 hours. The reaction solution was poured into ice-water, and the mixture was extracted with chloroform. The extract was washed with a saturated aqueous sodium chloride solution, and dried over magnesium sulfate. The solvent was evaporated under reduced pressure, and to the residue was added ethyl acetate. The precipitated crystals were collected by filtration, and dried to give the title compound (662 mg, 64%) as colorless crystals.

M.p. 163–165° C.; IR (KBr) 3302, 2963, 1691, 1645, 1577, 1548 cm$^{-1}$.

Example 25
Preparation of N-[1-butyl-2-oxo-4-[2-hydroxy-5-{3-(diethylamino)-1-propynyl}phenyl]-1,2-dihydropyridin-3-yl]-N'-(2,6-diisopropylphenyl)urea:

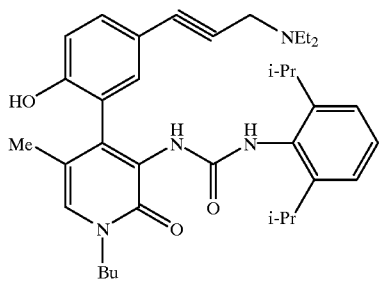

To a solution of propylene oxide (0.07 ml, 1.04 mmol) in methylene chloride (10 ml) was added BBr3 (0.29 ml, 3.11 mmol) under ice-cooling, and the mixture was stirred for 30 minutes. To the mixture was added N-[1-butyl-2-oxo-4-[2-methoxy-5-{3-(diethylamino)-1-propynyl}phenyl]-1,2-dihydropyridin-3-yl]-N'-(2,6-diisopropylphenyl)urea (303 mg, 0.518 mmol), and the mixture was stirred under reflux for 4 hours. To the reaction solution was added a 10% aqueous sodium hydroxide solution, and the mixture was acidified with 3N hydrochloric acid. The mixture was extracted with chloroform, and the extract was washed with a saturated aqueous sodium chloride solution, and dried over magnesium sulfate. The solvent was evaporated under reduced pressure, and the resulting residue was purified by silica gel column chromatography (ethyl acetate:hexane= 1:30) to give the title compound (77 mg, <26%) as colorless crystals.

The hydrochloride of the title compound was obtained in the same manner as in Example 10.

M.p. 184–185° C.; IR (KBr) 3240, 2963, 2231, 1698, 1645, 1571 cm$^{-1}$.

Example 26
Preparation of N-{1-butyl-2-oxo-4-(2-methoxy-5-hydroxy)phenyl-1,2-dihydropyridin-3-yl}-N'-(2,6-diisopropylphenyl)urea:

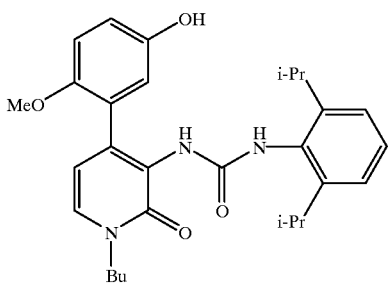

Pentamethylbenzene (815 mg, 5.50 mmol) was dissolved in TFA (11 ml), and thereto was added N-{1-butyl-2-oxo-4-(2-methoxy-5-benzyloxy)phenyl-1,2-dihydropyridin-3-yl}-N'-(2,6-diisopropylphenyl)urea (320 mg, 0.550 mmol) under ice-cooling, and the mixture was stirred at 50° C. for 3 hours. To the reaction solution were added ether and water, and the mixture was stirred under ice-cooling. The precipitated crystals were collected by filtration, and dried to give the title compound (270 mg, 100%) as colorless crystals.

M.p. 208–210° C.; IR (KBr) 3357, 3152, 2965, 1688, 1644, 1581 cm$^{-1}$.

Example 27
Preparation of N-[1-butyl-2-oxo-4-{2-methoxy-5-(3-pyridylmethoxy)}-phenyl-1,2-dihydropyridin-3-yl]-N'-(2,6-diisopropylphenyl)urea:

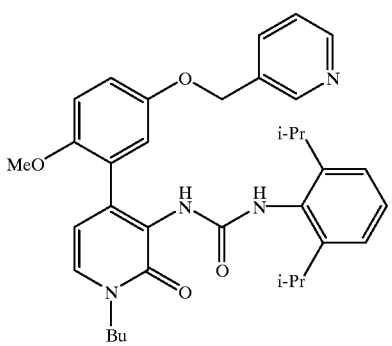

The title compound was obtained in the same manner as in Example 10 from N-[1-butyl-2-oxo-4-(2-methoxy-5-hydroxy)phenyl-1,2-dihydropyridin-3-yl]-N'-(2,6-diisopropylphenyl)urea and 3-chloromethylpyridine hydrochloride.

The hydrochloride of the title compound was obtained in the same manner as in Example 10.

$^1$H NMR δ (CD$_3$OD) 1.00 (t, J=7.3 Hz, 3H), 1.06 (d, J=4.4 Hz, 12H), 1.41–1.48 (m, 2H), 1.75–1.85 (m, 2H), 2.89 (bs, 2H), 3.82 (s, 3H), 4.07 (t, J=6.6 Hz, 2H), 5.32 (s, 2H), 6.32 (d, J=6.8 Hz, 1H), 7.03–7.07 (m, 5H), 7.18 (dd, J=8.1, 8.1 Hz, 1H), 7.54 (d, J=6.6 Hz, 1H), 8.00 (dd, J=6.8, 6.8 Hz, 1H), 8.68 (d, J=8.1 Hz, 1H), 8.76 (d, J=6.8 Hz, 1H), 8.94 (s, 1H).

Example 28

Preparation of N-[1-butyl-2-oxo-4-(2-isopropoxy-5-bromo)phenyl-1,2-dihydropyridin-3-yl]-N'-(2,6-diisopropylphenyl)urea:

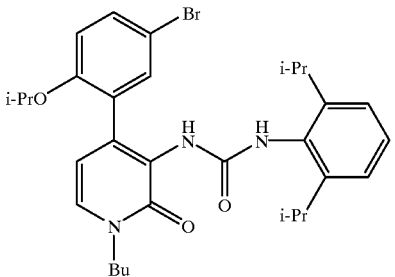

The title compound was obtained in the same manner as in Example 10 from N-[1-butyl-2-oxo-4-(2-hydroxy-5-bromo)phenyl-1,2-dihydropyridin-3-yl]-N'-(2,6-diisopropylphenyl)urea and isopropyl iodide.

$^1$H NMR δ (DMSO-d$_6$) 0.94 (t, J=7.3 Hz, 3H), 1.05 (bs, 12H), 1.19 (d, J=5.9 Hz, 6H), 1.31–1.38 (m, 2H), 1.65–1.72 (m, 2H), 2.81–2.91 (m, 2H), 3.96 (m, 2H), 4.55 (m, 1H), 6.16 (d, J=7.2 Hz, 1H), 6.98 (d. J=8.4 Hz, 1H), 7.02 (d, J=7.3 Hz, 2H), 7.14 (dd, J=7.3, 7.3 Hz, 1H), 7.33 (d, J=2.6 Hz, 1H), 7.38 (dd, J=2.6, 8.4 Hz, 1H), 7.44 (d, J=7.2 Hz, 1H), 7.86 (s, 2H).

Example 29

Preparation of N-[1-butyl-2-oxo-4-[2-isopropoxy-5-{3-(diethylamino)-1-propynyl}]phenyl-1,2-dihydropyridin-3-yl]-N'-(2,6-diisopropylphenyl)urea:

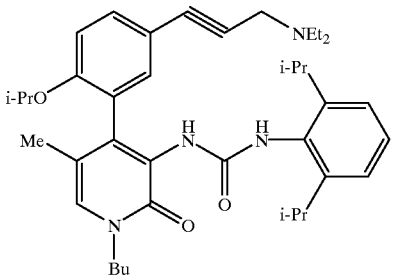

The title compound was obtained in the same manner as in Example 14 from N-[1-butyl-2-oxo-4-(2-isopropoxy-5-bromo)phenyl-1,2-dihydropyridin-3-yl]-N'-(2,6-diisopropylphenyl)urea.

The hydrochloride of the title compound was obtained in the same manner as in Example 10.

M.p. 133–142° C.; IR (KBr) 3324, 2964, 2231, 1691, 1647, 1597 cm$^{-1}$.

Example 30

Preparation of N-{1-butyl-2-oxo-4-(2-hydroxy-5-bromo)phenyl-1,2-dihydropyridin-3-yl}-N'-(2,4-bis(methylthio)-6-methylpyridin-3-yl]urea:

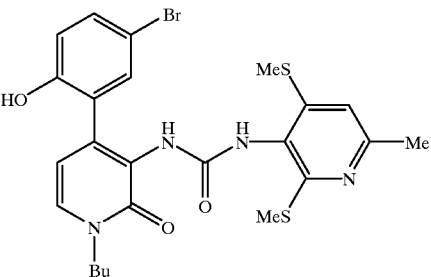

The title compound was obtained in the same manner as in Example 24 from N-{1-butyl-2-oxo-4-(2-methoxy-5-bromo)phenyl-1,2-dihydropyridin-3-yl}-N'-{2,4-bis(methylthio)-6-methylpyridin-3-yl}urea.

M.p. 138–142° C.

Example 31

Preparation of N-{1-butyl-2-oxo-4-(2-isopropoxy-5-bromo)phenyl-1,2-dihydropyridin-3-yl}-N'-{2,4-bis(methylthio)-6-methylpyridin-3-yl]urea:

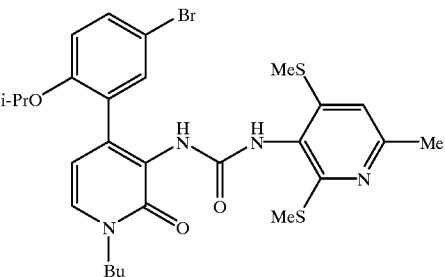

The title compound was obtained in the same manner as in Example 10 from N-{1-butyl-2-oxo-4-(2-hydroxy-5-bromo)phenyl-1,2-dihydropyridin-3-yl}-N'-(2,4-bis(methylthio)-6-methylpyridin-3-yl}urea and isopropyl iodide.

$^1$H NMR δ (CD$_3$OD) 0.86 (t, J=7.2 Hz, 3H), 1.14 (bs, 6H), 1.30 (tq, J=7.3, 7.3 Hz, 2H), 1.60–1.70 (m, 2H), 2.24 (s, 3H), 2.29 (s, 3H), 2.34 (s, 3H), 3.92 (t, J=7.2 Hz, 2H), 4.47 (bs, 1H), 6.19 (bs, 1H), 6.63 (bs, 1H), 6.85 (d, J=7.9 Hz, 1H), 7.31–7.33 (m, 2H), 7.37 (d, J=7.2 Hz, 1H).

Example 32

Preparation of N-[1-butyl-2-oxo-4-{2-(3-pyridylmethoxy)-5-bromo}-phenyl-1,2-dihydropyridin-3-yl]-N'-{2,4-bis(methylthio)-6-methylpyridin- 3-yl}urea:

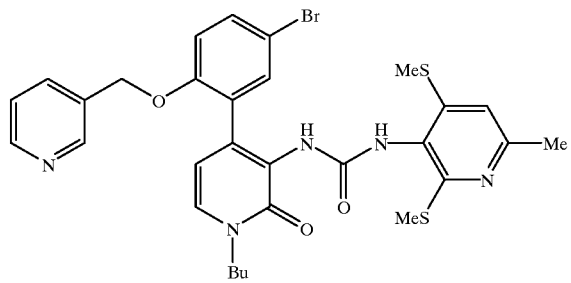

The title compound was obtained in the same manner as in Example 10 from N-{1-butyl-2-oxo-4-(2-hydroxy-5-bromo)phenyl-1,2-dihydropyridin-3-yl}-N'-{2,4-bis (methylthio)-6-methylpyridin-3-yl}urea and 3-chloromethylpyridine hydrochloride.

$^1$H NMR δ (DMSO-d$_6$) 0.94 (t, J=7.3 Hz, 3H), 1.04 (bs, 12H), 1.32–1.37 (m, 2H), 1.69–1.74 (m, 2H), 2.79 (br, 2H), 3.97 (br, 1H), 5.29 (s, 2H), 6.26 (d, J=7.0 Hz, 1H), 7.03 (d, J=7.7 Hz, 2H), 7.09 (d. J=8.8 Hz, 1H), 7.15 (dd, J=7.7, 7.7 Hz, 1H), 7.38 (d, J=2.4 Hz, 1H), 7.44–7.47 (m, 2H), 7.79 (dd, J=5.1, 8.3 Hz, 1H), 7.99 (s, 2H), 8.45 (d, J=8.3 Hz, 1H), 8.78 (d, J=5.1 Hz, 1H), 8.83 (s, 1H).

Example 33

Preparation of N-{1-butyl-2-oxo-4-(2-isopropoxy-4-benzyloxy)phenyl-1,2-dihydropyridin-3-yl}-N'-{2,4-bis(methylthio)-6-methylpyridin-3-yl}-urea:

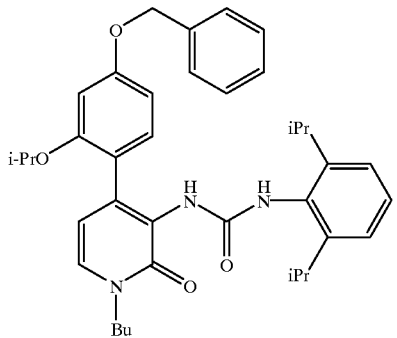

The title compound was obtained in the same manner as in Example 8 from 1-butyl-2-oxo-4-(2-isopropoxy-4-benzyloxy)phenyl-1,2-dihydropyridin-3-carboxylic acid and 2,6-diisopropylaniline.

M.p. 82–84° C.; IR (KBr) 3324, 2962, 1711, 1643, 1580 cm$^{-1}$.

Example 34

Preparation of N-{1-butyl-2-oxo-4-(2-isopropoxy-4-hydroxy)phenyl-1,2-dihydropyridin-3-yl}-N'-{2,6-diisopropylphenyl)urea:

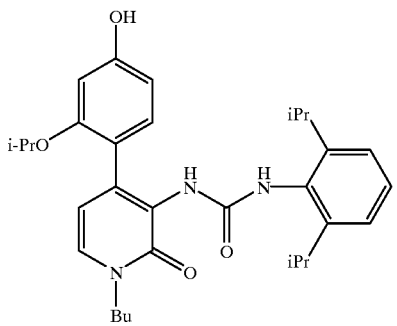

The title compound was obtained in the same manner as in Example 26 from N-{1-butyl-2-oxo-4-(2-isopropoxy-4-benzyloxy)phenyl-1,2-dihydropyridin-3-yl}-N'-(2,6-diisopropylphenyl)urea.

M.p. 174–177° C.; IR (KBr) 3295, 2963, 1688, 1645, 1578 cm$^{-1}$.

Example 35

Preparation of N-{1-butyl-2-oxo-4-(2-isopropoxy-4-methoxy)phenyl-1,2-dihydropyridin-3-yl}-N'-(2,6-diisopropylphenyl-3-yl)urea:

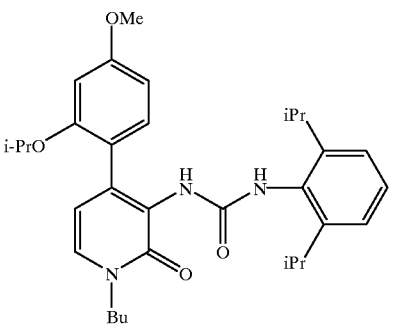

The title compound was obtained in the same manner as in Example 10 from N-{1-butyl-2-oxo-4-(2-isopropoxy-4-hydroxy)phenyl-1,2-dihydropyridin-3-yl}-N'-(2,6-diisopropylphenyl)urea and methyl iodide.

M.p. 170–172° C.; IR (KBr) 3326, 2959, 1706, 1647 cm$^{-1}$.

Example 36

Preparation of N-{1-butyl-2-oxo-4-(2-isopropoxy-4-benzyloxy)phenyl-1,2-dihydropyridin-3-yl}-N'-{2,4-bis(methylthio)-6-methylpyridin-3-yl}-urea:

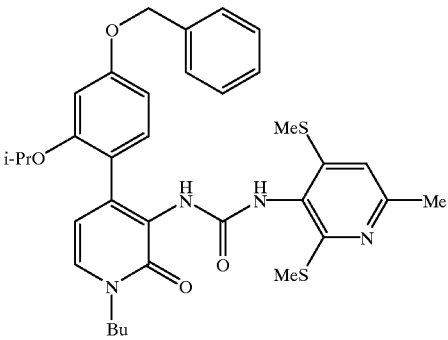

The title compound was obtanin the same manner as in Example 8 from 1-butyl-2-oxo-4-(2-isopropoxy-4-benzyloxy)phenyl-3-carboxylic acid and 3-amino-2,4-bis(methylthio)-6-methylpyridine.

M.p. 119–125° C.; IR (KBr) 3317, 2961, 1700, 1678, 16412, 1576 cm$^{-1}$.

Example 37

Preparation of N-{1-butyl-2-oxo-4-(2-isopropoxy-4-hydroxy)phenyl-1,2-dihydropyridin-3-yl}-N'-{2,4-bis(methylthio)-6-methylpyridin-3-yl}urea:

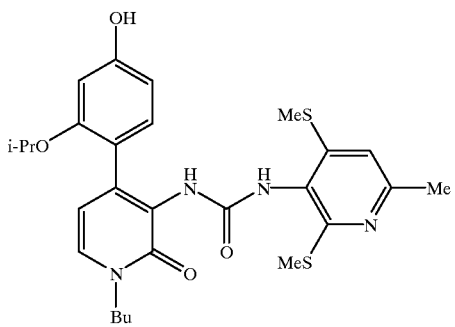

The title compound was obtained in the same manner as in Example 26 from N-(1-butyl-2-oxo-4-(2-isopropoxy-4-benzyloxy)phenyl-1,2-dihydropyridin-3-yl}-N'-{2,4-bis(methylthio)-6-methylpyridin-3-yl}urea.

M.p. 192–198° C.; IR (KBr) 3318, 2961, 1700, 1644 cm$^{-1}$.

Example 38

Preparation of N-{1-butyl-2-oxo-4-(2-isopropoxy-4-methoxy)phenyl-1,2-dihydropyridin-3-yl}-N'-{2,4-bis(methylthio)-6-methylpyridin-3-yl}urea:

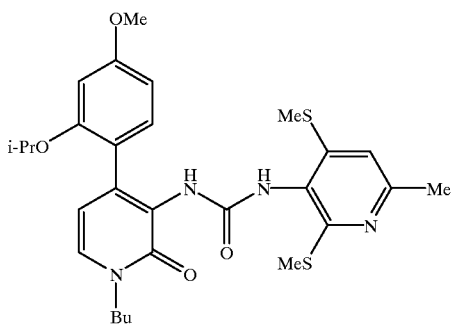

The title compound was obtained in the same manner as in Example 10 from N-{1-butyl-2-oxo-4-(2-isopropoxy-4-hydroxy)phenyl-1,2-dihydropyridin-3-yl}-N'-{2,4-bis(methylthio)-6-methylpyridin-3-yl}urea and methyl iodide.

M.p. 169–170° C.; IR (KBr) 3318, 2961, 1700, 1642, 1582 cm$^{-1}$.

Example 39

Preparation of N-{1-butyl-2-oxo-4-(2-isopropoxy-5-benzyloxy)phenyl-1,2-dihydropyridin-3-yl}-N'-{2,6-diisopropylphenyl)urea:

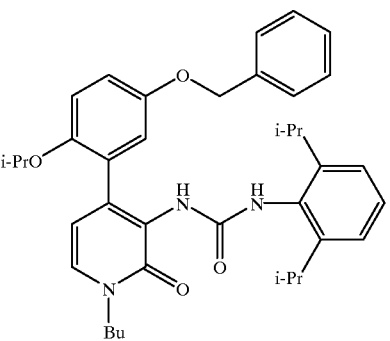

The title compound was obtained in the same manner as in Example 8 from 1-butyl-2-oxo-4-(2-isopropoxy-5-benzyloxy)phenyl- 1,2-dihydropyridin-3-carboxylic acid and 2,6-diisopropylaniline.

M.p. 86–87° C. (flocculated and decomposed); IR (KBr) 3318, 2963, 2868, 1643, 1581, 1499, 1466, 1382, 1207 cm$^{-1}$.

Example 40

Preparation of N-1-butyl-2-oxo-4-(2-isopropoxy-5-hydroxy)phenyl-1,2-dihydropyridin-3-yl}-N'-{2,6-diisopropylphenyl)urea:

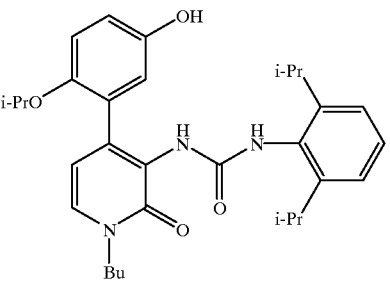

The title compound was obtained in the same manner as in Example 26 from N-{1-butyl-2-oxo-4-(2-isopropoxy-5-benzyloxy)phenyl-1,2-dihydropyridin-3-yl}-N'-(2,6-diisopropylphenyl)urea.

M.p. 196–197° C. (decomposed); IR (KBr) 3217, 2964, 1687, 1645, 1578, 1498, 1464, 1334, 1212 cm$^{-1}$.

Example 41

Preparation of N-[1-butyl-2-oxo-4-{2-isopropoxy-5-(2-pyridylmethoxy)phenyl}-1,2-dihydropyridin-3-yl]-N'-(2,6-diisopropylphenyl)urea:

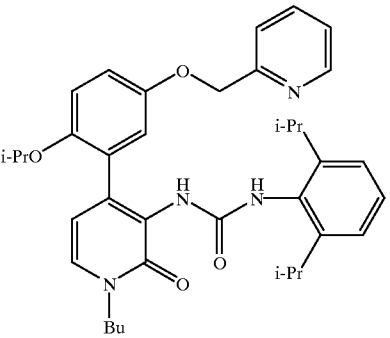

The hydrochloride of the title compound was obtained in the same manner as in Example 10 from N-{1-butyl-2-oxo- 4-(2-isopropoxy- 5-hydroxy)phenyl-1,2-dihydropyridin-3-yl}-N'-(2,6-diisopropylphenyl)urea and 2-chloromethylpyridine hydrochloride.

M.p. 184–185° C. (decomposed); IR (KBr) 3252, 2964, 2869, 1646, 1602, 1520, 1467, 1382, 1213 cm$^{-1}$.

Example 42

Preparation of N-[1-butyl-2-oxo-4-{2-isopropoxy-5-(3-pyridylmethoxy)phenyl)-1,2-dihydropyridin-3-yl]-N'-(2,6-diisopropylphenyl)urea:

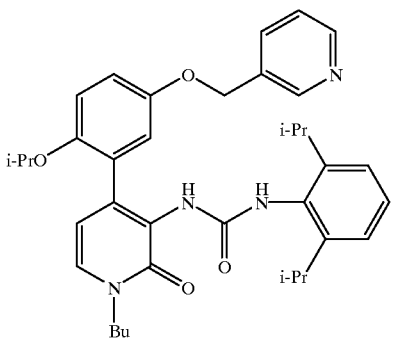

The hydrochloride of the title compound was obtained in the same manner as in Example 10 from N-{1-butyl-2-oxo-4-(2-isopropoxy-5-hydroxy)phenyl-1,2-dihydropyridin-3-yl}-N'-(2,6-diisopropylphenyl)urea and 3-chloromethylpyridine hydrochloride.

M.p. 138–140° C. (flocculated and decomposed); IR (KBr) 3250, 3066, 2964, 2869, 1642,1606, 1545, 1498, 1468, 1383 cm$^{-1}$.

Example 43

Preparation of N-[1-butyl-2-oxo-4-{2-isopropoxy-5-(2-piperidinoethoxy)phenyl}-1,2-dihydropyridin-3-yl]-N'-(2,6-diisopropylphenyl)urea:

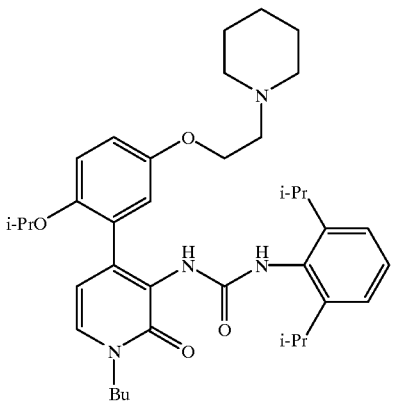

The hydrochloride of the title compound was obtained in the same manner as in Example 10 from N-{1-butyl-2-oxo-4-(2-isopropoxy-5-hydroxy)phenyl-1,2-dihydropyridin-3-yl}-N'-(2,6-diisopropylphenyl)urea and 1-(2-chloroethyl) piperidine hydrochloride.

M.p. 130–132° C. (flocculated and decomposed); IR (KBr) 3324, 2964, 2869, 1647, 1587, 1489, 1382, 1216 cm$^{-1}$.

Example 44

Preparation of N-[1-butyl-2-oxo-4-{2-isopropoxy-5-(2-morpholinoethoxy)phenyl}-1,2-dihydropyridin-3-yl]-N'-(2,6-diisopropylphenyl)urea:

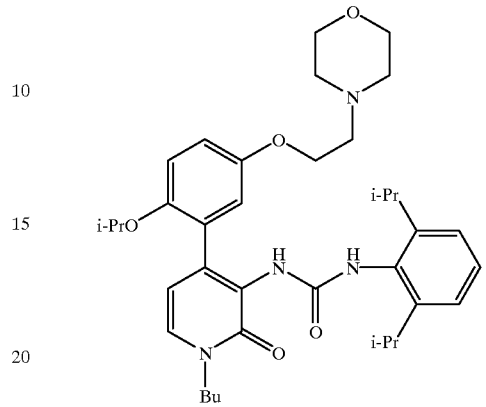

The hydrochloride of the title compound was obtained in the same manner as in Example 10 from N-{1-butyl-2-oxo-4-(2-isopropoxy-5-hydroxy)phenyl-1,2-dihydropyridin-3-yl}-N'-(2,6-diisopropylphenyl)urea and 4-(2-chloroethyl) morpholine hydrochloride.

M.p. 96–98° C. (flocculated and decomposed); IR (KBr) 3327, 2964, 2870, 1616, 1583, 1499, 1467, 1383 cm$^{-1}$.

Example 45

Preparation of N-[1-butyl-2-oxo-4-{2-isopropoxy-5-(2-diethylaminoethoxy)phenyl}-1,2-dihydropyridin-3-yl]-N'-(2,6-diisopropylphenyl)urea:

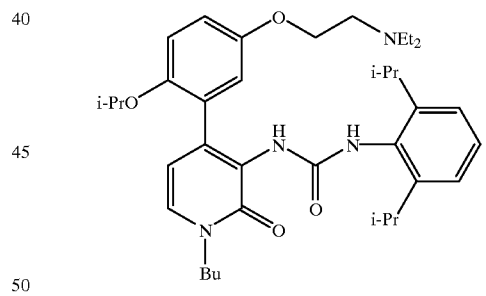

The hydrochloride of the title compound was obtained in the same manner as in Example 10 from N-{1-butyl-2-oxo-4-(2-isopropoxy-5-hydroxy)phenyl-1,2-dihydropyridin-3-yl}-N'-(2,6-diisopropylphenyl)urea and 2-chlorotriethylamine hydrochloride.

M.p. 73–75° C. (flocculated and decomposed); IR (KBr) 3318, 2963, 2870, 1646, 1582, 1498, 1468, 1383, 1214 cm$^{-1}$.

Example 46

Preparation of N-[1-butyl-2-oxo-4-[2-isopropoxy-5-{3-(1,2,4-triazol-1-yl)propoxy}phenyl]-1,2-dihydropyridin-3-yl]-N'-(2,6-diisopropylphenyl)urea:

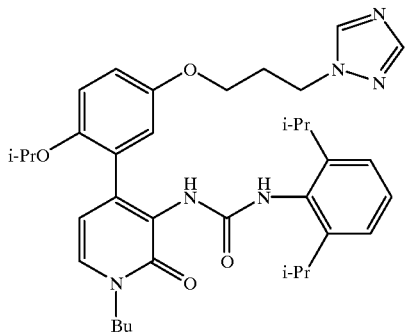

The hydrochloride of the title compound was obtained in the same manner as in Example 10 from N-{1-butyl-2-oxo-4-(2-isopropoxy-5-hydroxy)phenyl-1,2-dihydropyridin-3-yl}-N'-(2,6-diisopropylphenyl)urea and 1-(3-bromopropyl)-1,2,4-triazole.

M.p. 84–86° C. (flocculated and decomposed); IR (KBr) 3320, 2964, 2870, 1645, 1582, 1500, 1467, 1383, 1214 cm$^{-1}$.

Example 47

Preparation of N-[1-butyl-2-oxo-4-{2-isopropoxy-5-(4-pyridylmethoxy)phenyl}-1,2-dihydropyridin-3-yl]-N'-(2,6-diisopropylphenyl)urea:

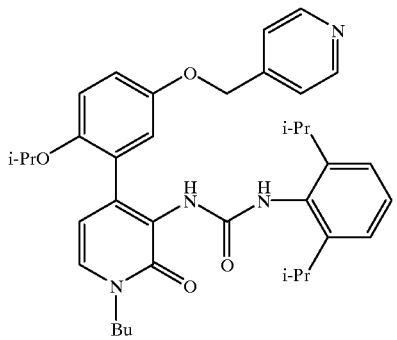

The hydrochloride of the title compound was obtained in the same manner as in Example 10 from N-{1-butyl-2-oxo-4-(2-isopropoxy-5-hydroxy)phenyl-1,2-dihydropyridin-3-yl}-N'-(2,6-diisopropylphenyl)urea and 4-chloromethylpyridine hydrochloride.

M.p. 95–97° C. (decomposed); IR (KBr) 3254, 2963, 2869, 1644, 1605, 1501, 1468, 1383, 1224 cm$^{-1}$.

Example 48

Preparation of N-{1-butyl-2-oxo-4-(2-isopropoxy-4-methoxy)phenyl-1,2-dihydropyridin-3-yl}-N'-{2,4-bis(methylthio)-6-methylpyridin-3-yl}urea:

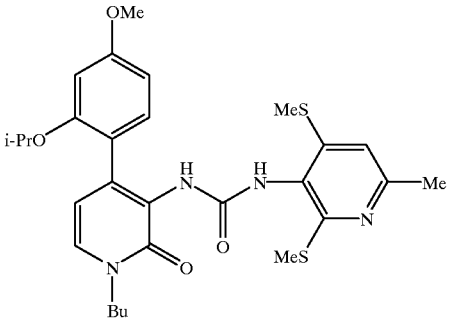

To a solution of N-{1-butyl-2-oxo-4-(2-isopropoxy-4-hydroxy)-phenyl-1,2-dihydropyridin-3-yl}-N'-(2,4-bis(methylthio)-6-methylpyridin-3-yl}urea (880 mg, 1.62 mmol) in dimethyolformamide (10 ml) were added potassium carbonate (689 mg, 4.99 mmol) and methyl iodide (1.55 ml, 2.49 mmol), and the mixture was stirred at about 50° C. for 6 hours. The mixture was diluted with ethyl acetate, and the reaction was quenched by addition of water, and the mixture was extracted with ethyl acetate. The organic layer was washed with water and a saturated aqueous sodium chloride solution, and the solvent was evaporated under reduced pressure to give a crude product. The crude product thus obtained was purified by silica gel column chromatography (ethyl acetate), and crystallized from ethyl acetate/diethyl ether to give the title compound.

The crystals thus obtained were dissolved in tetrahydrofuran (4 ml) under heating, and converted into a hydrochloride thereof with iN hydrochloric acid/diethyl ether (1 ml). To the mixture was added diethyl ether (10 ml) for crystallization, and the crystals were collected by filtration to give the hydrochloride of the title compound (391 mg, 0.68 mmol).

M.p. 212–214° C. (flocculated and decomposed); IR (KBr) 3245, 2959, 1691, 1611, 1530, 1442, 1382, 1304 cm$^{-1}$.

Example 49

Preparation of N-[1-butyl-2-oxo-4-{2-isopropoxy-4-(3-pyridylmethoxy)phenyl}-1,2-dihydropyridin-3-yl]-N'-(2,4-bis(methylthio)-6-methylpyridin-3-yl}urea:

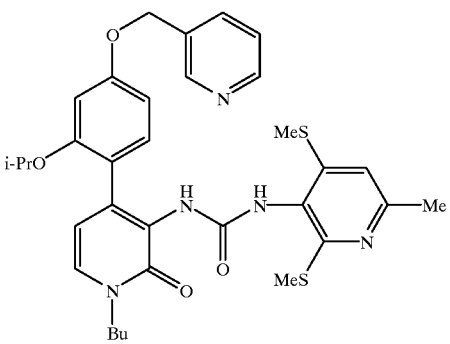

The hydrochloride of the title compound was obtained in the same manner as in Example 10 from N-{1-butyl-2-oxo-4-(2-isopropoxy-4-hydroxy)phenyl-1,2-dihydropyridin-3-yl}-N'-{2,4-bis(methylthio)-6-methylpyridin-3-yl}urea and 3-chloromethylpyridine hydrochloride.

M.p. 176–178° C. (flocculated and decomposed); IR (KBr) 3424, 2958, 1689, 1608, 1570, 1430, 1383, 1304 cm$^{-1}$.

Example 50

Preparation of N-[1-butyl-2-oxo-4-{2-isopropoxy-4-(2-piperidinoethoxy)phenyl}-1,2-dihydropyridin-3-yl]-N'-(2,6-diisopropylphenyl)urea:

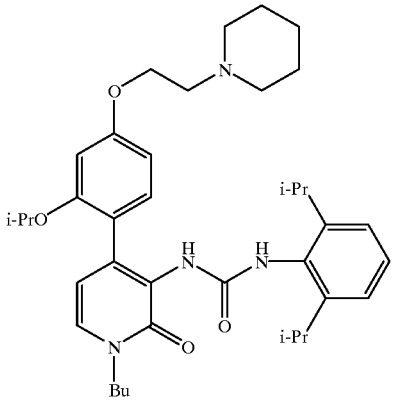

The hydrochloride of the title compound was obtained in the same manner as in Example 10 from N-{1-butyl-2-oxo-4-(2-isopropoxy-4-hydroxy)phenyl-1,2-dihydropyridin-3-yl}-N'-(2,6-diisopropylphenyl)urea and 1-(2-chloroethyl)piperidine hydrochloride.

M.p. 122–124° C. (flocculated and decomposed); IR (KBr) 3338, 2963, 1646, 1578, 1508, 1466, 1301, 1190, 1110 cm$^{-1}$.

Example 51

Preparation of N-[1-butyl-2-oxo-4-{2-isopropoxy-4-(3-piperidinopropoxy)phenyl}-1,2-dihydropyridin-3-yl]-N'-(2,6-diisopropylphenyl)urea:

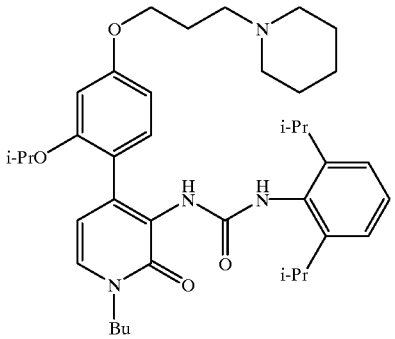

The hydrochloride of the title compound was obtained in the same manner as in Example 10 from N-{1-butyl-2-oxo-4-(2-isopropoxy-4-hydroxy)phenyl-1,2-dihydropyridin-3-yl}-N'-(2,6-diisopropylphenyl)urea and 1-(3-chloropropyl)piperidine hydrochloride.

M.p. 116–118° C. (flocculated and decomposed); IR (KBr) 3400, 2962, 1644, 1578, 1466, 1383, 1300, 1190, 1111, 926 cm$^{-1}$.

Example 52

Preparation of N-[1-butyl-2-oxo-4-(2-isopropoxy-4-(2-morpholinoethoxy)phenyl)-1,2-dihydropyridin-3-yl]-N'-(2,6-diisopropylphenyl)urea:

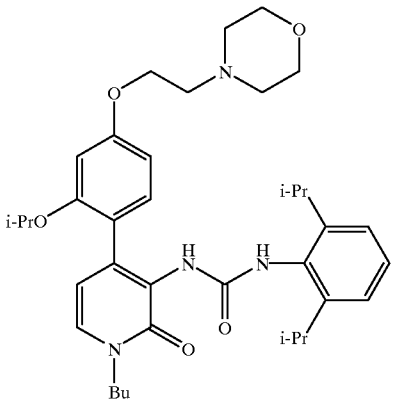

The hydrochloride of the title compound was obtained in the same manner as in Example 10 from N-{1-butyl-2-oxo-4-(2-isopropoxy- 4-hydroxy)phenyl-1,2-dihydropyridin-3-yl}-N'-(2,6-diisopropylphenyl)urea and 4-(2-chloroethyl)morpholine hydrochloride.

M.p. 117–119° C. (flocculated and decomposed); IR (KBr) 3400, 2966, 1644, 1578, 1465, 1384, 1301, 1190, 1134, 1107 cm$^{-1}$.

Example 53

Preparation of N-[1-butyl-2-oxo-4-[2-isopropoxy-4-{3-(1,2,4-triazol-1-yl)propoxyphenyl}-1,2-dihydropyridin-3-yl]-N'-(2,6-diisopropylphenyl)urea:

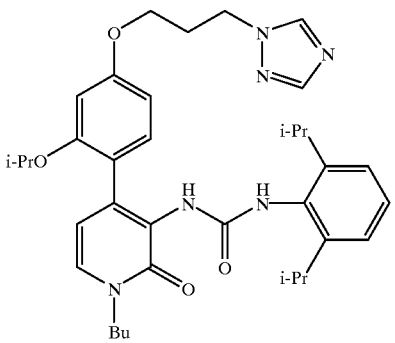

The hydrochloride of the title compound was obtained in the same manner as in Example 10 from N-{1-butyl-2-oxo-4-(2-isopropoxy-4-hydroxy)phenyl-1,2-dihydropyridin-3-yl}-N'-(2,6-diisopropylphenyl)urea and 1-(3-bromopropyl)-1,2,4-triazole.

M.p. 98–104° C. (flocculated and decomposed); IR (KBr) 3328, 2964, 1643, 1576, 1508, 1466, 1384, 1301, 1190, 1112 cm$^{-1}$.

Example 54

Preparation of N-{1-butyl-2-oxo-4-(2-methoxy-5-fluorophenyl)-1,2-dihydropyridin-3-yl}-N'-(2,6-diisopropylphenyl)urea:

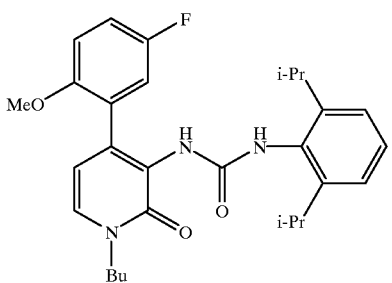

The title compound was obtained in the same manner as in Example 8 from 1-butyl-2-oxo-4-(2-methoxy-5-fluorophenyl)-1,2-dihydropyridine-3-carboxylic acid and 2,6-diisopropylaniline.

M.p. 165–166° C. (flocculated and decomposed); IR (KBr) 3321, 2961, 2872, 1701, 1644, 1579, 1517, 1467, 1258, 1210 cm$^{-1}$.

Example 55

Preparation of N-{1-butyl-2-oxo-4-(2-methoxy-5-fluorophenyl)-1,2-dihydropyridin-3-yl}-N'-{2,4-bis(methylthio)-6-methylpyridin-3-yl}urea:

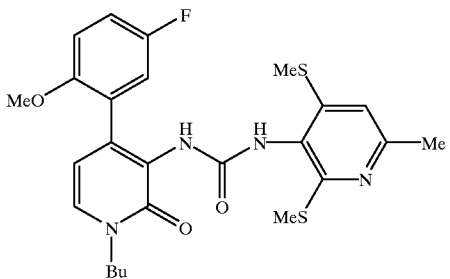

The title compound was obtained in the same manner as in Example 8 from 1-butyl-2-oxo-4-(2-methoxy-5-fluorophenyl)-1,2-dihydropyridine-3-carboxylic acid and 3-amino-2,4-bis(methylthio)-6-methylpyridine.

M.p. 194–196° C.; IR (KBr) 3319, 2958, 2928, 1701, 1642, 1579, 1500, 1434, 1212 cm$^{-1}$.

Example 56

Preparation of N-{1-butyl-2-oxo-4-(2-methoxyphenyl)-1,2-dihydropyridin- 3-yl}-N'-{2,4-bis(methylthio)-6-methylpyridin-3-yl}urea:

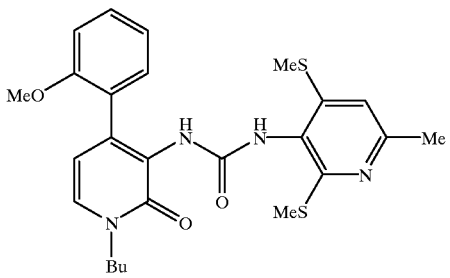

The title compound was obtained in the same manner as in Example 8 from 1-butyl-2-oxo-4-(2-methoxyphenyl)-1,2-dihydropyridine-3-carboxylic acid and 3-amino-2,4-bis(methylthio)-6-methylpyridine.

M.p. 196–199° C.; IR (KBr) 3318, 2958, 2925, 2872, 1701, 1641, 1578, 1516, 1255, 1211 cm$^{-1}$.

Example 57

Preparation of N-[1-butyl-2-oxo-4-{2-(3-dimethylaminopropoxy)phenyl}-1,2-dihydropyridin-3-yl]-N'-(2,6-diisopropylphenyl)urea:

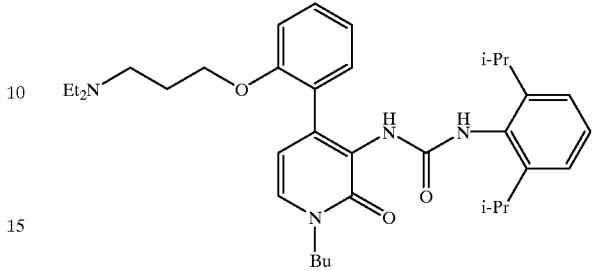

a) Preparation of 1-butyl-2-oxo-3-amino-4-(2-methoxyphenyl)-1,2-dihydropyridine:

The title compound was obtained in the same manner as in Example 3 from 1-butyl-2-oxo-3-carbamoyl-4-(2-methoxyphenyl)-1,2-dihydropyridine.

$^1$H NMR δ (DMSO-d$_6$) 0.93 (t, J=7.3 Hz, 3H), 3.76 (s, 3H), 4.53 (s, 2H).

b) Preparation of 1-butyl-2-oxo-3-amino-4-(2-hydroxyphenyl)-1,2-dihydropyridine:

The title compound was obtained in the same manner as in Example 9 from 1-butyl-2-oxo-3-amino-4-(2-methoxyphenyl)-1,2-dihydropyridine.

$^1$H NMR δ (DMSO-d$_6$) 0.90 (t, J=7.3 Hz, 3H), 3.89 (d, J=5.6, 2H), 7.14–7.22 (m, 2H).

c) Preparation of 1-butyl-2-oxo-3-amino-4-{2-(3-dimethylaminopropoxy)phenyl}-1,2-dihydropyridine:

The title compound was obtained in the same manner as in Example 10 from 1-butyl-2-oxo-3-amino-4-(2-hydroxyphenyl)-1,2-dihydropyridine and 3-dimethylaminopropyl chloride hydrochloride.

$^1$H NMR δ (DMSO-d$_6$) 0.89 (t, J=7.3 Hz, 3H), 2.10 (s, 6H).

d) Preparation of N-[1-butyl-2-oxo-4-{2-(3-dimethylaminopropoxy)phenyl-1,2-dihydropyridin-3-yl}-N'-(2,6-diisopropylphenyl)urea:

The title compound was obtained in the same manner as in Example 4 from 1-butyl-2-oxo-3-amino-4-{2-(3-dimethylaminopropoxy)phenyl}-1,2-dihydropyridine and 2,6-diisopropylaniline.

$^1$H NMR δ (DMSO-d$_6$) 0.88–1.07 (m, 15H), 2.18 (s, 6H).

The title compound was converted into a hydrochloride thereof in the same manner as in Example 10.

$^1$H NMR δ (DMSO-d$_6$) 0.85–1.10 (m, 15H), 1.28–1.40 (m, 2H), 2.51 (s, 3H), 2.53 (s, 3H), 3.00–3.10 (m, 2H).

IR (KBr) 3316, 2952, 2869, 1645, 1580, 1523, 1467, 1383, 1227 cm$^{-1}$.

Example 58

Preparation of N-[1-butyl-2-oxo-4-{2-(2-piperidinoethoxy-5-methoxyphenyl)}-1,2-dihydropyridin-3-yl]-N'-(2,6-diisopropylphenyl)urea:

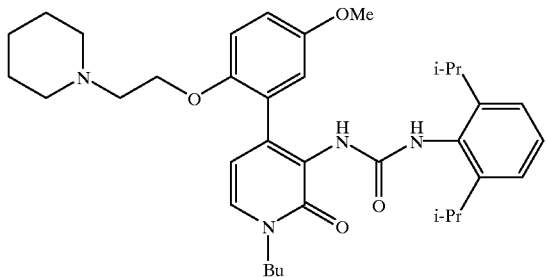
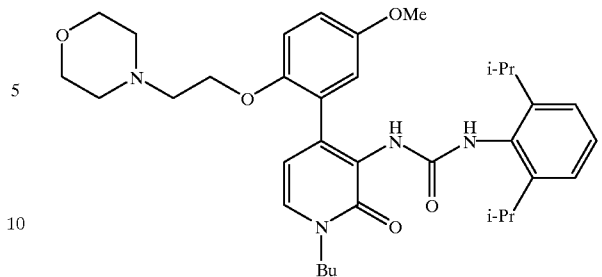

a) Preparation of 1-butyl-2-oxo-3-amino-4-(2-benzyloxy-5-methoxyphenyl)-1,2-dihydropyridine:

The title compound was obtained in the same manner as in Example 3 from 1-butyl-2-oxo-3-carbamoyl-4-(2-benzyloxy-5-methoxyphenyl)-1,2-dihydropyridine.

$^1$H NMR δ (DMSO-$d_6$) 0.90 (t, J=7.3 Hz, 3H), 3.71 (s, 3H), 4.65 (s, 2H), 5.02 (s, 2H), 6.03 (d, J=7.0 Hz, 1H).

b) Preparation of 1-butyl-2-oxo-3-amino-4-(2-hydroxy-5-methoxyphenyl)-1,2-dihydropyridine:

To a solution of 1-butyl-2-oxo-3-amino-4-(2-benzyloxy-5-methoxyphenyl)-1,2-dihydropyridine (1.20 g, 3.17 mmol) in methanol (20 ml) was added 10% Pd/C (50% wet, 300 mg), and the mixture was stirred at room temperature for one hour under hydrogen atmosphere. After confirming the completion of the reaction, the reaction solution was filtered through a cerite pad, and the filtrate was concentrated to give the title compound (883 mg) as pale yellow amorphous, which was used in the subsequent reaction without further purification.

$^1$H NMR δ (DMSO-$d_6$) 0.94 (t, J=7.3 Hz, 3H), 3.68 (s, 3H), 4.68 (s, 2H).

c) Preparation of 1-butyl-2-oxo-3-amino-4-{2-(2-piperidinoethoxy)-5-methoxyphenyl)-1,2-dihydropyridine:

The title compound was obtained in the same manner as in Example 10 from 1-butyl-2-oxo-3-amino-4-(2-hydroxy-5-methoxyphenyl)-1,2-dihydropyridine and 1-(2-chloroethyl)piperidine hydrochloride.

$^1$H NMR δ (DMSO-$d_6$) 0.91 (t, J=3 Hz, 3H), 1.25–1.43 (m, 8H), 1.61–1.68 (m, 2H), 2.29–2.32 (m, 2H), 2.50–2.56 (m, 2H), 3.72 (s, 3H), 4.71 (br s, 2H).

d) Preparation of N-[1-butyl-2-oxo-4-{2-(2-piperidinoethoxy)-5-methoxyphenyl}-1,2-dihydropyridin-3-yl]-N'-(2,6-diisopropylphenyl)urea:

The title compound was obtained in the same manner as in Example 4 from 1-butyl-2-oxo-3-amino-4-{2-(2-piperidinoethoxy)-5-methoxyphenyl}-1,2-dihydropyridine and 2,6-diisopropylaniline.

$^1$H NMR δ (DMSO-$d_6$) 0.82–0.98 (m, 15H), 1.23–1.42 (m, 8H), 1.62–1.67 (m, 2H), 2.82–2.87 (m, 2H), 3.67 (s, 3H), 3.91–3.97 (m, 4H).

The title compound was converted into a hydrochloride thereof in the same manner as in Example 10.

M.p. 146–148° C.;

$^1$H NMR δ (DMSO-$d_6$) 0.82–1.14 (m, 19H), 1.26–1.37 (m, 2H), 1.60–1.69 (m, 2H), 3.73 (s, 3H), 7.89 (s, 1H), 7.98 (s, 1H); IR (KBr) 3307, 2961, 2870, 1646, 1587, 1499, 1467, 1383, 1216 cm$^{-1}$.

Example 59

Preparation of N-[1-butyl-2-oxo-4-(2-(2-morpholinoethoxy)-5-methoxyphenyl}-1,2-dihydropyridin-3-yl]-N'-(2,6-diisopropylphenyl)urea:

a) Preparation of 1-butyl-2-oxo-3-amino-4-{2-(2-morpholinoethoxy)-5-methoxyphenyl}-1,2-dihydropyridine:

The title compound was obtained in the same manner as in Example 10 from 1-butyl-2-oxo-3-amino-4-(2-hydroxy-5-methoxyphenyl)-1,2-dihydropyridine and 4-(2-chloroethyl)morpholine hydrochloride.

$^1$H NMR δ (DMSO-$d_6$) 0.90 (t, J=7.3 Hz, 3H), 3.71 (s, 3H), 4.68 (s, 3H).

b) Preparation of N-[1-butyl-2-oxo-4-{2-(2-morpholinoethoxy)-5-methoxyphenyl}-1,2-dihydropyridin-3-yl]-N'-(2,6-diisopropylphenyl)urea:

The title compound was obtained in the same manner as in Example 4 from 1-butyl-2-oxo-3-amino-4-{2-(2-morpholinoethoxy)-5-methoxyphenyl}-1,2-dihydropyridine and 2,6-diisopropylaniline.

$^1$H NMR δ (DMSO-$d_6$) 0.85–0.99 (m, 15H), 2.82–2.90 (m, 2H), 3.46–3.52 (m, 4H), 3.68 (s, 3H), 3.91–4.06 (m, 4H).

The title compound was converted into a hydrochloride thereof in the same manner as in Example 10.

M.p. 156–158° C. (decomposed);

$^1$H NMR δ (DMSO-$d_6$) 0.90–1.08 (m, 15H), 2.80–3.05 (m, 2H), 3.20–3.45 (m, 2H), 3.67–3.76 (m, H), 4.27–4.33 (br, 2H); IR (KBr) 3308, 2963, 2871, 1813, 1646, 1590, 1500, 1466, 1216 cm$^{-1}$.

Example 60

Preparation of N-[1-butyl-2-oxo-4-[2-{3-(1,2,4-triazol-1-yl)propoxy}-5-methoxyphenyl]-1,2-dihydropyridin-3-yl]-N'-(2,6-diisopropylphenyl)urea:

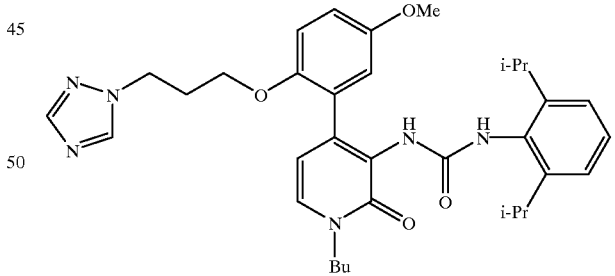

a) Preparation of 1-butyl-2-oxo-3-amino-4-[2-{3-(1,2,4-triazol-1-yl)propoxy}-5-methoxyphenyl]-1,2-dihydropyridine:

The title compound was obtained in the same manner as in Example 10 from 1-butyl-2-oxo-3-amino-4-(2-hydroxy-5-methoxyphenyl)-1,2-dihydropyridine and 1-(3-bromopropyl)-1,2,4-triazole.

$^1$H NMR δ (DMSO-$d_6$) 0.88 (t, J=7.3 Hz, 3H), 3.68 (s, 3H), 4.70 (s, 2H), 7.93 (s, 1H), 8.36 (s, 1H).

b) Preparation of N-[1-butyl-2-oxo-4-[2-{3-(1,2,4-triazol-1-yl)-propoxy}-5-methoxyphenyl}-1,2-dihydropyridin-3-yl]-N'-(2,6-diisopropylphenyl)urea:

The title compound was obtained in the same manner as in Example 4 from 1-butyl-2-oxo-3-amino-4-[2-{3-(1,2,4-triazol-1-yl)-propoxy}-5-methoxyphenyl]-1,2-dihydropyridine and 2,6-diisopropylaniline.

$^1$H NMR δ (DMSO-$d_6$) 0.85–1.02 (m, 15H), 2.75–2.90 (m, 2H), 3.68 (s, 3H), 7.94 (s, 1H), 8.27 (s, 1H).

The title compound was converted into a hydrochloride thereof in the same manner as in Example 10.

$^1$H NMR δ (DMSO-$d_6$) 0.84–1.05 (m, 15H), 1.23–1.35 (m, 2H), 2.05–2.12 (m, 2H), 3.68 (s, 3H), 3.84–3.96 (m, 4H), 7.82 (s, 1H), 7.85 (s, 1H), 8.04 (s, 1H), 8.46 (s, 1H); IR (KBr) 3307, 2963, 2871, 1642, 1580, 1502, 1468, 1217 cm$^{-1}$.

Example 61
Preparation of N-[1-butyl-2-oxo-4-{2-(3-piperidinopropoxy)-5-methoxyphenyl}-1,2-dihydropyridin-3-yl]-N'-(2,6-diisopropylphenyl)urea:

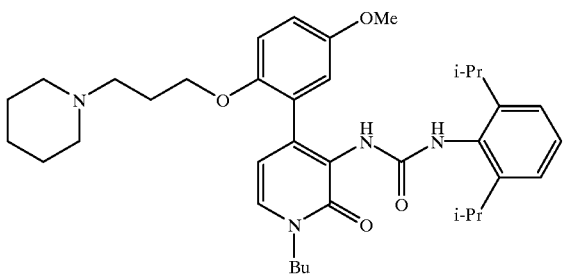

a) Preparation of 1-butyl-2-oxo-3-amino-4-{2-(3-piperidinopropoxy)-5-methoxyphenyl}-1,2-dihydropyridine:

The title compound was obtained in the same manner as in Example 10 from 1-butyl-2-oxo-3-amino-4-(2-hydroxy-5-methoxyphenyl)-1,2-dihydropyridine and 1-(3-chloropropyl)piperidine hydrochloride.

$^1$H NMR δ (DMSO-$d_6$) 0.90 (t, J=7.3 Hz, 3H), 1.22–1.45 (m, 8H), 1.57–1.74 (m, 4H), 3.72 (s, 3H), 3.86–3.92 (m, 4H), 4.61 (s, 2H).

b) Preparation of N-[1-butyl-2-oxo-4-{2-(3-piperidinopropoxy)-5-methoxyphenyl)-1,2-dihydropyridin-3-yl]-N'-(2,6-diisopropylphenyl)urea:

The title compound was obtained in the same manner as in Example 4 from 1-butyl-2-oxo-3-amino-4-{2-(3-piperidinopropoxy)-5-methoxyphenyl}-1,2-dihydropyridine and 2,6-diisopropylaniline.

$^1$H NMR δ (DMSO-$d_6$) 0.85–1.11 (m, 15H), 1.29–1.44 (m, 8H), 1.63–1.73 (m, 4H), 2.81–2.87 (m, 2H), 3.67 (s, 3H), 3.86–3.97 (m, 4H), 7.68 (s, 1H), 7.77 (s, 1H).

The title compound was converted into a hydrochloride thereof in the same manner as in Example 10.

M.p. 173–176° C. (decomposed);

$^1$H NMR δ (DMSO-$d_6$) 0.80–1.10 (m, 15H), 1.95–1.99 (m, 2H), 2.76–2.82 (m, 2H), 2.94–3.02 (m, 2H), 3.12–3.16 (m, 2H), 3.70 (s, 3H), 3.80–4.05 (m, 4H), 7.91 (s, 1H), 8.03 (s, 1H); IR (KBr) 3244, 2960, 2869, 1694, 1596, 1499, 1468, 1215 cm$^{-1}$.

Example 62
Preparation of N-1-butyl-2-oxo-4-{2-(3-pyridylmethoxy)-5-methoxyphenyl}-1,2-dihydropyridin-3-yl]-N'-(2,6-diisopropylphenyl)urea:

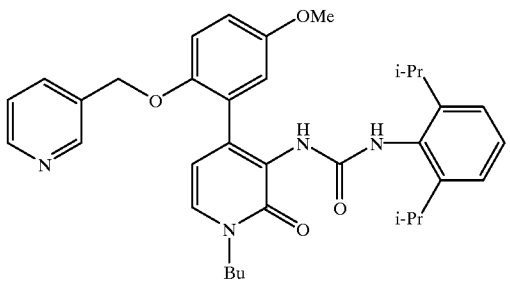

a) Preparation of 1-butyl-2-oxo-3-amino-4-{2-(3-pyridylmethoxy)-5-methoxyphenyl}-1,2-dihydropyridine:

The title compound was obtained in the same manner as in Example 10 from 1-butyl-2-oxo-3-amino-4-(2-hydroxy-5-methoxyphenyl)-1,2-dihydropyridine and 3-chloromethylpyridine hydrochloride.

$^1$H NMR δ (DMSO-$d_6$) 0.89 (t, J=7.3 Hz, 3H), 3.72 (s, 3H), 4.69 (s, 2H), 5.07 (s, 2H).

b) Preparation of N-[1-butyl-2-oxo-4-{2-(3-pyridylmethoxy)-5-methoxyphenyl}-1,2-dihydropyridin-3-yl]-N'-(2,6-diisopropylphenyl)urea:

The title compound was obtained in the same manner as in Example 4 from 1-butyl-2-oxo-3-amino-4-{2-(3-pyridylmethoxy)-5-methoxyphenyl}-1,2-dihydropyridine and 2,6-diisopropylaniline.

$^1$H NMR δ (DMSO-$d_6$) 0.82–1.30 (m, 15H), 3.69 (s, 3H), 5.03 (s, 2H), 6.82–6.86 (m, 2H), 6.98–7.14 (m, 4H), 7.79 (s, 1H), 7.85 (s, 1H), 8.54 (s, 1H).

The title compound was converted into a hydrochloride thereof in the same manner as in Example 10.

M.p. 138–141° C. (decomposed);

$^1$H NMR δ (DMSO-$d_6$) 0.80–1.08 (m, 15H), 1.27–1.37 (m, 2H), 1.62–1.70 (m, 2H), 2.70–2.90 (m, 2H), 3.70 (s, 3H), 5.21 (s, 2H), 8.81 (s, 1H);

IR (KBr) 2870, 1756, 1712, 1644, 1580, 1500, 1469, 1197 cm$^{-1}$.

Example 63
Preparation of N-{1-butyl-2-oxo-4-(2-isopropoxy-5-benzyloxyphenyl)-1,2-dihydropyridin-3-yl}-N'-{2-tert-butyl-5-(1-pyrazolylmethyl)phenyl}urea:

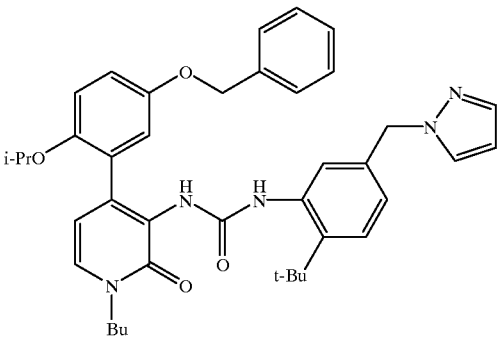

The title compound was obtained in the same manner as in Example 8 from 1-butyl-2-oxo-4-(2-isopropoxy-5-benzyloxyphenyl)-1,2-dihydropyridine-3-carboxylic acid and 2-tert-butyl-5-(1-pyrazolylmethyl)aniline, and further the hydrochloride thereof was obtained in the same manner as in Example 10.

M.p. 102–103° C.; IR (KBr) 2963, 2872, 1645, 1578, 1528, 1498 cm$^{-1}$.

Example 64

Preparation of N-{1-butyl-2-oxo-4-(2-isopropoxy-5-hydroxyphenyl)-1,2-dihydropyridin-3-yl}-N'-{2-tert-butyl-5-(1-pyrazolylmethyl)phenyl}urea:

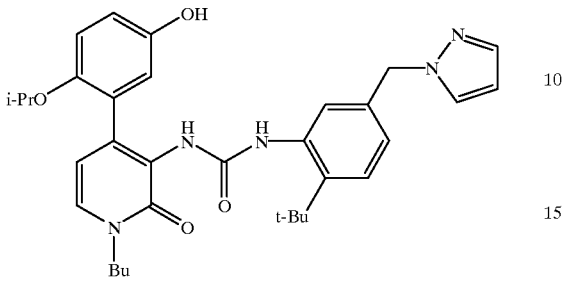

The title compound was obtained in the same manner as in Example 58 b) from N-{1-butyl-2-oxo-4-(2-isopropoxy-5-benzyloxyphenyl)-1,2-dihydropyridin-3-yl}-N'-{2-tert-butyl-5-(1-pyrazolylmethyl)phenyl}urea, and further the hydrochloride thereof was obtained in the same manner as in Example 10.

M.p. 142–143° C.; IR (KBr) 2968, 2873, 1645, 1578, 1539, 1497 cm$^{-1}$.

Example 65

Preparation of N-{1-butyl-2-oxo-4-(2-isopropoxy-5-methoxyphenyl)-1,2-dihydropyridin-3-yl}-N'-{2-tert-butyl-5-(1-pyrazolylmethyl)phenyl}urea:

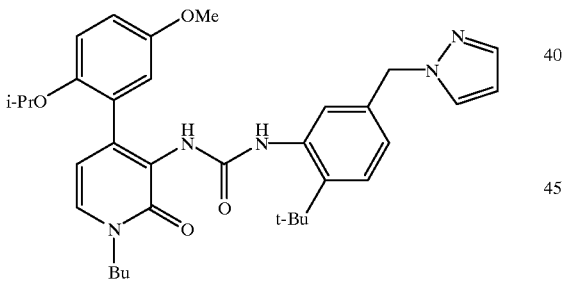

The title compound was obtained in the same manner as in Example 48 from N-{1-butyl-2-oxo-4-(2-isopropoxy-5-hydroxyphenyl)-1,2-dihydropyridin-3-yl}-N'-{2-tert-butyl-5-(1-pyrazolylmethyl)phenyl}urea, and further the hydrochloride thereof was obtained in the same manner as in Example 10.

M.p. 99–100° C.; IR (KBr) 2963, 2873, 1644, 1580, 1421 cm$^{-1}$.

Example 66

Preparation of N-1-butyl-2-oxo-4-{2-isopropoxy-5-(3-pyridylmethoxy)phenyl}-1,2-dihydropyridin-3-yl]-N'-{2-tert-butyl-5-(1-pyrazolylmethyl)phenyl}urea:

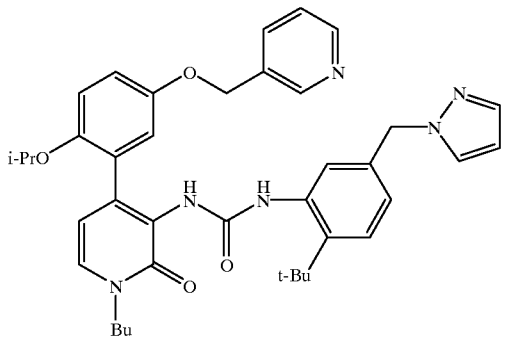

The hydrochloride of the title compound was obtained in the same manner as in Example 10 from N-{1-butyl-2-oxo-5-(2-isopropoxy-5-hydroxyphenyl)-1,2-dihydropyridin-3-yl}-N'-{2-tert-butyl-5-(1-pyrazolylmethyl)phenyl}urea and 3-chloromethylpyridine.

$^1$H NMR δ (DMSO-d$_6$) 0.94 (t, J=7.3 Hz, 3H), 1.13 (d, J=6.0 Hz, 6H), 1.17 (s, 9H), 3.96 (t, J=7.0 Hz, 2H), 7.20 (d, J=8.8 Hz, 1H).

Example 67

Preparation of N-{1-butyl-2-oxo-4-(2-isopropoxy-4-benzyloxyphenyl)-1,2-dihydropyridin-3-yl}-N'-{2-tert-butyl-5-(1-imidazolylmethyl)phenyl}urea:

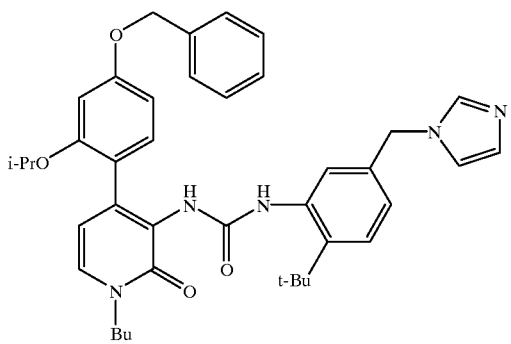

The title compound was obtained in the same manner as in Example 8 from 1-butyl-2-oxo-4-(2-isopropoxy-4-benzyloxyphenyl)-1,2-dihydropyridine-3-carboxylic acid and 2-tert-butyl-5-(1-imidazolylmethyl)aniline, and the hydrochloride thereof was further obtained in the same manner as in Example 10.

M.p. 138–140° C.; IR (KBr) 2963, 2871, 1643, 1607, 1574, 1541 cm$^{-1}$.

Example 68

Preparation of N-{1-butyl-2-oxo-4-(2-isopropoxy-4-hydroxyphenyl)-1,2-dihydropyridin-3-yl}-N'-{2-tert-butyl-5-(1-imidazolylmethyl)phenyl}urea:

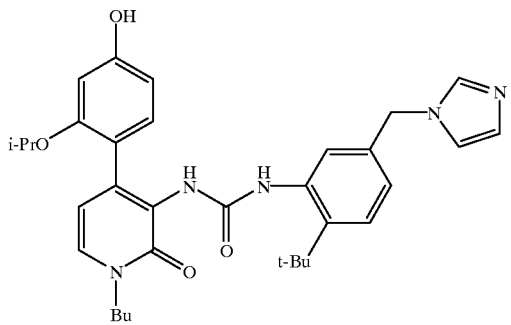

The title compound was obtained in the same manner as in Example 58 b) from N-{1-butyl-2-oxo-4-(2-isopropoxy-4-benzyloxyphenyl)-1,2-dihydropyridin-3-yl}-N'-{2-tert-butyl-5-(1-imidazolylmethyl)phenyl}urea, and the hydrochloride thereof was further obtained in the same manner as in Example 10.

M.p. 162–163° C.; IR (KBr) 2962, 2872, 1642, 1610, 1579, 1541 cm$^{-1}$.

Example 69

Preparation of N-{1-butyl-2-oxo-4-(2-isopropoxy-4-methoxyphenyl)-1,2-dihydropyridin-3-yl}-N'-{2-tert-butyl-5-(1-imidazolylmethyl)phenyl}urea:

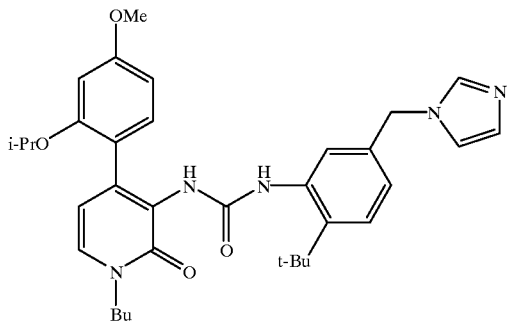

The title compound was obtained in the same manner as in Example 48 from N-{1-butyl-2-oxo-4-(2-isopropoxy-4-hydroxyphenyl)-1,2-dihydropyridin-3-yl}-N'-{2-tert-butyl-5-(1-imidazolylmethyl)phenyl}urea, and further the hydrochloride thereof was obtained in the same manner as in Example 10.

M.p. 147–148° C.; IR (KBr) 2962, 2871, 1646, 1604, 1508, 1466 cm$^{-1}$.

Example 70

Preparation of N-[1-butyl-2-oxo-4-{2-isopropoxy-4-(3-pyridylmethoxy)phenyl}-1,2-dihydropyridin-3-yl]-N'-{2-tert-butyl-5-(1-imidazolylmethyl)phenyl}urea:

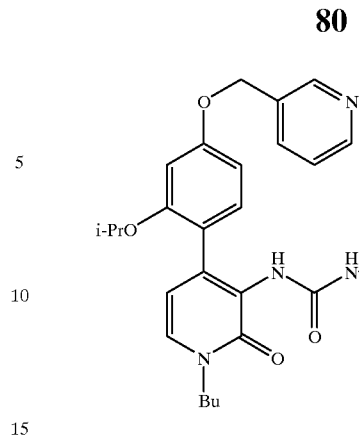

The title compound was obtained in the same manner as in Example 10 from N-{1-butyl-2-oxo-4-(2-isopropoxy-4-hydroxyphenyl)-1,2-dihydropyridin-3-yl}-N'-{2-tert-butyl-5-(1-imidazolylmethyl)phenyl}urea and 3-chloromethylpyridine, and the hydrochloride thereof was further obtained in the same manner as in Example 10.

$^1$H NMR δ (DMSO-d$_6$) 0.94 (t, J=7.3 Hz, 3H), 1.13 (d, J=6.0 Hz, 6H), 1.17 (s, 9H), 5.15 (s, 2H), 5.24 (s, 2H), 7.20 (d, J=8.8 Hz).

M.p. 111–112° C.; IR (KBr) 2964, 2872, 1643, 1607, 1577, 1543 cm$^{-1}$.

Reference Example 1

Preparation of 1-butyl-3-carbamoyl-4-(3-methoxyphenyl)-1,2-dihydro-2-oxo-1,8-naphthyridine:

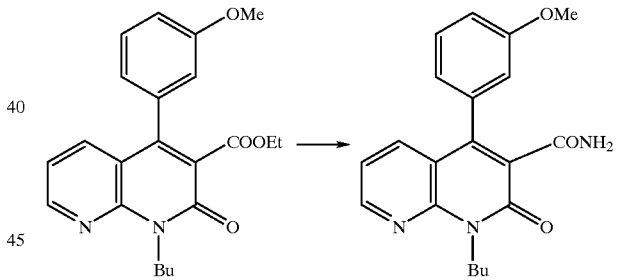

A mixture of 1-butyl-3-ethoxycarbonyl-4-(3-methoxyphenyl)-1,2-dihydro-2-oxo-1,8-naphthyridine (45.0 g, 120 mmol), formamide (15.5 ml, 390 mmol) and dimethylformamide (120 ml) was dissolved at 60° C., and thereto was added a 25% solution of sodium methoxide in methanol (108 ml, 390 mmol), and the mixture was stirred at 60° C. for 9 hours. The mixture was cooled to 0° C., and thereto was added water (1.2 liter), and the mixture was stirred for 15 minutes. The precipitated solid was collected by filtration, washed with ethanol, and dried to give the title compound (37.8 g, yield; 87%) as white powder.

M.p. 239–240° C.

Reference Example 2

Preparation of 1-butyl-3-carbamoyl-4-(3-methoxyphenyl)-1,2-dihydro-2-oxo-1,8-naphthyridine:

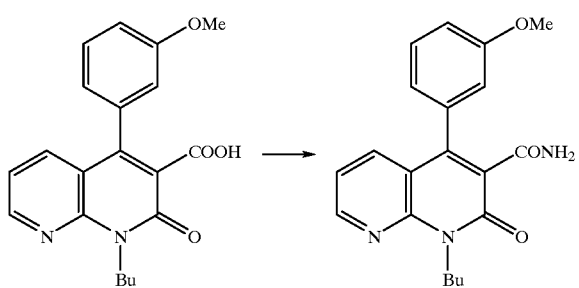

To a suspension of 1-butyl-3-carboxy-4-(3-methoxyphenyl)-1,2-dihydro-2-oxo-1,8-naphthyridine (10.0 g, 28.4 mmol) in toluene (300 ml) was added thionyl chloride (2.95 g, 34.1 mmol), and the mixture was stirred at room temperature for 0.5 hour, and then stirred at 90–100° C. for 6 hours. After allowed to cool, the mixture was concentrated under reduced pressure. To the concentrated residue was added toluene, and the mixture was concentrated again under reduced pressure. The concentrated residue was dissolved in dioxane (100 ml), and the mixture was added dropwise into conc. aqueous ammonia (80 ml) in an ice-bath. The mixture was stirred at room temperature for 6 hours, and poured into water. The precipitated crystals were collected by filtration, dispersed in ethanol (50 ml), and the mixture was stirred for one hour. The solid thus obtained was collected by filtration to give the title compound (9.12 g, 24.8 mmol, yield; 87%) as colorless powder.

M.p. 239–240° C.

Reference Example 3
Preparation of 2-(butylamino)-3-(3-methoxybenzoyl)pyridine:

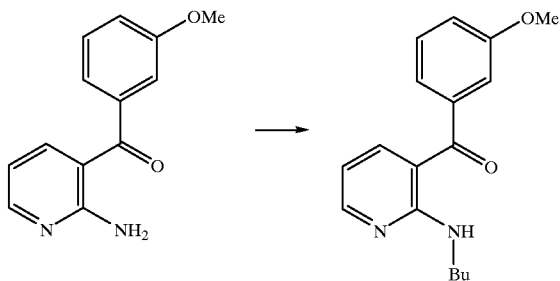

To a suspension of sodium hydride (60%, 578 mg, 14.5 mmol) in tetrahydrofuran (15 ml) was added dropwise a solution of 3-(2-aminopyridyl)-(3-methoxyphenyl)ketone (3.00 g, 13.1 mmol) in tetrahydrofuran (24 ml) under ice-cooling, and further thereto was added dropwise a solution of butyl iodide (3.63 g, 19.7 mmol) in tetrahydrofuran at room temperature, and the mixture was stirred at 50–60° C. for 6 hours. The mixture was cooled to room temperature, and thereto was added water. The mixture was extracted with toluene, and washed successively with a 5% aqueous sodium hydrogen carbonate solution, water and a 5% aqueous sodium chloride solution, dried over magnesium sulfate, and concentrated under reduced pressure. The residue was purified by silica gel column chromatography (ethyl acetate/hexane=¼) to give the title compound (2.96 g, 10.4 mmol, 79%) as yellow oil.

$^1$H NMR δ (CDCl$_3$) 0.98 (3H, t, J=7.3 Hz), 1.43–1.55 (2H, m), 1.65–1.75 (2H, m), 3.56–3.62 (2H, m), 3.85 (3H, s), 6.47 (1H, dd, J=7.9 Hz, 4.8 Hz), 7.06–7.13 (3H, m), 7.37 (1H, dd, J=8.3 Hz, 8.3 Hz), 7.76 (1H, dd, J=7.9 Hz, 2.0 Hz), 8.32 (1H, dd, J=4.8 Hz, 2.0 Hz), 8.82 (1H, brs)

Reference Example 4
Preparation of 2-{(N-butyl-N-phthalimideacetyl)amino}-3-(3-methoxybenzoyl)pyridine:

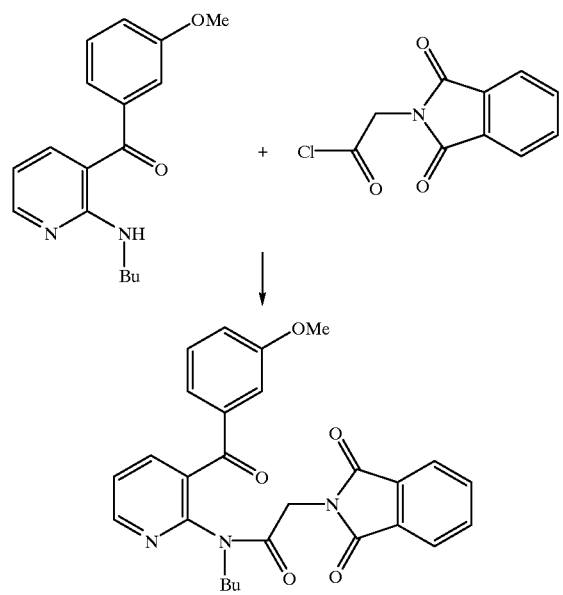

To a suspension of N-phthaloylglycine (4.76 g, 23.2 mmol) in toluene (24 ml) were added thionyl chloride (5.08 ml, 69.6 mmol) and dimethylformamide (0.4 ml), and the mixture was stirred at 50–60° C. for 30 minutes. After allowed to cool, the solvent was evaporated under reduced pressure. The residue was subjected twice to azeotropic distillation with toluene, and the residue was suspended in dioxane (20 ml). The mixture was added dropwise to a solution of 2-(butylamino)-3-(3-methoxybenzoyl)pyridine (3.30 g, 11.6 mmol) in pyridine (27 ml) at room temperature. The mixture was stirred at 50–60° C. for one hour, stirred at 60–70° C. for one hour, and further stirred at 70–80° C. for one hour. The mixture was cooled to room temperature, and water was added therein, and the mixture was extracted with ethyl acetate. The extract was washed with successively with 1N hydrochloric acid, water, a 5% aqueous sodium hydrogen carbonate solution, and a 5% aqueous sodium chloride solution, dried over anhydrous magnesium sulfate, concentrated under reduced pressure, and purified by silica gel column chromatography (ethyl acetate/hexane=½) to give the title compound (3.77 g, 8.00 mmol, 69%) as yellow amorphous.

$^1$H NMR δ (CDCl$_3$) 0.74 (3H, t, J=7.3 Hz, 3 Hz), 1.11–1.23 (2H, m), 1.36–1.43 (2H, m), 3.36–3.46 (2H, m), 3.88 (3H, s), 4.45 (2H, s), 7.11–7.25 (2H, m), 7.27–7.51 (2H, m), 7.67–7.75 (3H, m), 7.77–7.94 (3H, m), 8.74 (1H, s).

Reference Example 5
Preparation of 1-butyl-2-oxo-4-(3-methoxy)phenyl-1,2-dihydropyridine-3-carboxylic acid:
a) Preparation of ethyl 2-cyano-3-(3-methoxy)phenyl-crotonate:

To a solution of 3-methoxyacetophenone (25 g, 166 mmol) in toluene (40 ml) were added ethyl cyanoacetate (18.8 g, 166 mmol), ammonium acetate (2.6 g, 33.2 mmol) and acetic acid (7.6 ml, 133 mmol), and the mixture was stirred under reflux for about 6 hours. To the reaction solution was added water, and the mixture was extracted with ethyl acetate. The extract was washed with a saturated aqueous sodium chloride solution and dried over magnesium sulfate. The solvent was evaporated under reduced pressure, and the resulting residue was purified by silica gel column chromatography (ethyl acetate:hexane=1:10) to give the title compound (13.9 g, yield; 34%) as brown oil.

$^1$H NMR δ (CDCl$_3$) 1.14 and 1.26 (t and t, J=7.2 and 7.2 Hz, 3H), 2.53 and 2.68 (s and s, 3H), 3.80 and 3.83 (s and s, 3H), 4.12 and 4.34 (q and q, J=7.2 and 7.2 Hz, 2H), 6.68–6.75 and 6.91–7.02 (m and m, 3H), 7.26–7.39 (m, 1H).

b) Preparation of ethyl 2-oxo-4-(3-methoxy)phenyl-1,2-dihydropyridine-3-carboxylate:

To ethyl 2-cyano-3-(3-methoxy)phenyl-crotonate (12.3 g, 50.1 mmol) was added N,N-dimethylformamide dimethyl acetal (17 ml), and the mixture was stirred at room temperature for about 5 hours. The solvent was evaporated under reduced pressure, and thereto was added 80% aqueous acetic acid solution (625 ml), and the mixture was stirred under reflux for about 2 hours. The solvent was evaporated under reduced pressure, and water was added to the reaction solution, and the mixture was extracted with ethyl acetate. The extract was washed with a saturated aqueous sodium chloride solution, and dried over anhydrous magnesium sulfate. The solvent was evaporated under reduced pressure, and the resulting residue was purified by silica gel column chromatography (ethyl acetate:hexane=2:1) to give the title compound (8.69 g, yield; 67%) as brown crystals.

M.p. 153–156° C.; IR (KBr) 3433, 1727, 1646, 1531 cm$^{-1}$.

c) Preparation of ethyl 1-butyl-2-oxo-4-(3-methoxy)phenyl-1,2-dihydropyridine-3-carboxylate:

To a solution of ethyl 2-oxo-4-(3-methoxy)phenyl-1,2-dihydropyridine-3-carboxylate (7.69 g, 29.9 mmol) in DMF (60 ml) were added potassium carbonate (12.4 g, 89.7 mmol) and butyl iodide (5.1 ml, 44.9 mmol), and the mixture was stirred at room temperature for about 3 hours. Water was added to the reaction solution, and the mixture was extracted with ethyl acetate. The extract was washed with a saturated aqueous sodium chloride solution, and dried over magnesium sulfate. The solvent was evaporated under reduced pressure, and the resulting residue was purified by silica gel column chromatography (ethyl acetate:hexane=1:1) to give the title compound (7.65 g, yield; 78%) as brown oil.

$^1$H NMR δ (CDCl$_3$) 0.97 (t, J=7.3 Hz, 3H), 1.11 (t, J=7.2 Hz, 3H), 1.37–1.47 (m, 2H), 1.73–1.83 (m, 2H), 3.82 (s, 3H), 3.97 (t, J=7.3 Hz, 2H), 4.19 (q, J=7.2 Hz, 2H), 6.23 (d, J=7.0 Hz, 1H), 6.92–7.01 (m, 3H), 7.26–7.34 (m, 2H); IR (neat) 2960, 1732, 1650, 1600 cm$^{-1}$.

d) Preparation of 1-butyl-2-oxo-4-(3-methoxy)phenyl-1,2-dihydropyridine-3-carboxylic acid:

To a solution of ethyl 1-butyl-2-oxo-4-(3-methoxy)phenyl-1,2-dihydropyridine-3-carboxylate (6.05 g, 18.4 mmol) in ethanol (30 ml) was added sodium hydroxide (2.94 g, 73.5 mmol), and the mixture was stirred under reflux for about 7 hours. The pH value of the mixture was adjusted to pH 3 with 3N aqueous hydrochloric acid solution, and the precipitated crystals were collected by filtration, and dried to give the title compound (5.00 g, yield; 90%) as brown crystals.

M.p. 108–110° C.; IR (KBr) 3420, 1737, 1627, 1568 cm$^{-1}$.

Reference Example 6

Preparation of 1-butyl-2-oxo-4-(3-bromo)phenyl-1,2-dihydropyridine-3-carboxylic acid:

The title compound was obtained in the same manner as in Reference Example 5.

$^1$H NMR δ (CDCl$_3$) 1.01 (t, J=7.3 Hz, 3H), 1.40–1.47 (m, 2H), 1.79 (m, 2H), 4.11 (t, J=7.5 Hz, 2H), 6.37 (d, J=7.0 Hz, 1H), 7.20 (d, J=7.7 Hz, 1H), 7.28 (dd, J=7.7, 7.7 Hz, 1H), 7.40 (dd, J=2.0, 2.0 Hz, 1H), 7.53 (d, J=7.7 Hz, 1H), 7.56 (d, J=7.0 Hz, 1H);

M.p. 139–142° C.; IR (KBr) 3437, 1732, 1626, 1565 cm$^{-1}$.

Reference Example 7

Preparation of 1-butyl-2-oxo-4-(3-bromo)phenyl-5-methyl-1,2-dihydropyridine-3-carboxylic acid:

The title compound was obtained in the same manner as in Reference Example 5.

$^1$H NMR δ (CDCl$_3$) 1.02 (t, J=7.3 Hz, 3H), 1.41–1.48 (m, 2H), 1.79–1.86 (m, 2H), 1.80 (s, 3H), 4.09 (t, J=7.3 Hz, 2H), 7.00 (ddd, J=1.5, 1.5, 7.7 Hz, 1H), 7.20 (dd, J=1.5, 1.5 Hz, 1H), 7.32 (dd, J=7.7, 7.7 Hz, 1H), 7.44 (d, J=1.1 Hz, 1H), 7.51 (ddd, J=1.1, 1.5, 7.7 Hz, 1H);

M.p. 197–198° C.; IR (KBr) 3437, 3068, 1732, 1633, 1564 cm$^{-1}$.

Reference Example 8

Preparation of 1-butyl-2-oxo-4-(5-bromo-2-methoxy)phenyl-1,2-dihydropyridine-3-carboxylic acid:

The title compound was obtained in the same manner as in Reference Example 5.

$^1$H NMR δ (CDCl$_3$) 1.01 (t, J=7.3 Hz, 3H), 1.38–1.57 (m, 2H), 1.79–1.89 (m, 2H), 3.74 (s, 3H), 4.03–4.16 (m, 2H), 6.35 (d, J=6.8 Hz, 1H), 6.80 (d, J=8.8 Hz, 1H), 7.19 (d, J=2.6 Hz, 1H), 7.45 (dd, J=2.6, 8.8 Hz, 1H), 7.56 (d, J=6.8 Hz, 1H);

M.p. 179–180° C.; IR (KBr) 3436, 3033, 2969, 1720, 1623, 1568 cm$^{-1}$.

Reference Example 9

Preparation of 1-butyl-2-oxo-4-(2,5-dimethoxy)phenyl-1,2-dihydropyridine-3-carboxylic acid:

The title compound was obtained in the same manner as in Reference Example 5.

$^1$H NMR δ (CDCl$_3$) 1.01 (t, J=7.5 Hz, 3H), 1.45 (tq, J=7.5, 7.5 Hz, 2H), 1.84 (tt, J=7.5, 7.5 Hz, 2H), 3.72 (s, 3H), 3.77 (s, 3H), 4.01–4.12 (br, 2H), 6.39 (d, J=6.8 Hz, 1H), 6.67 (dd, J=0.7, 2.6 Hz, 1H), 6.84–6.88 (m, 2H), 7.53 (d, J=6.8 Hz, 1H).

Reference Example 10

Preparation of 1-butyl-2-oxo-4-(2-methoxy-5-benzyloxy)phenyl-1,2-dihydropyridine-3-carboxylic acid:

The title compound was obtained in the same manner as in Reference Example 5.

$^1$H NMR δ (CDCl$_3$) 1.01 (t, J=7.3 Hz, 3H), 1.44 (tq, J=7.3, 7.3 Hz, 2H), 1.84 (tt, J=7.3, 7.3 Hz, 2H), 3.72 (s, 3H), 4.11 (br, 2H), 5.01 (s, 2H), 6.37 (d, J=7.0 Hz, 1H), 6.76 (d, J=3.1 Hz, 1H), 6.85 (d, J=9.0 Hz, 1H), 6.96 (dd, J=3.1, 9.0 Hz, 1H), 7.30-7.44 (m, 5H), 7.52 (d, J=7.0 Hz, 1H).

Reference Example 11

Preparation of 1-butyl-2-oxo-4-(2-isopropoxy-4-benzyloxy)phenyl-1,2-dihydropyridine-3-carboxylic acid:

The title compound was obtained from 1-acetyl-2-isopropoxy-4-benzyloxybenzene in the same manner as in Reference Example 5.

$^1$H NMR δ (CDCl$_3$) 1.00 (t, J=7.3 Hz, 3H), 1.23 (d, J=5.5 Hz, 6H), 1.43 (tq, J=7.3, 7.3 Hz, 2H), 1.83 (tt, J=7.3, 7.3 Hz, 2H), 4.08 (br, 2H), 4.45 (qq, J=5.5, 5.5 Hz, 1H), 5.06 (s, 2H), 6.40 (d, J=6.8 Hz, 1H), 6.55 (d, J=2.2 Hz, 1H), 6.59 (dd, J=2.2, 8.4 Hz, 1H), 7.05 (d, J=8.4 Hz, 1H), 7.31– 7.49 (m, 6H).

The ACAT inhibitory activity of the present compounds can be evaluated by the following method.

Experiment

1. Assay of ACAT Inhibitory Activity in a Specimen Prepared from Rabbit Liver:

An enzyme specimen ACAT was prepared according to the method disclosed in the literature: J. Lipid. Research, 30, 681–690, 1989, from the liver of New Zealand white rabbit, which had been fed with 1% cholesterol feed for one month. The ACAT activity was determined according to the method disclosed in the literature: J. Lipid Research, 24, 1127–1134, 1983, i.e., using radioactive [1-$^{14}$C]oleoyl-CoA and endogenous cholesterol contained in the liver microsome, and calculated from the radioactivity of the labeled cholesterol oleate. The results are shown in Table 13.

TABLE 13

| Test compound (Example No.) | ACAT inhibitory activity IC$_{50}$ (nM) |
| --- | --- |
| 18 (hydrochloride) | 295 |

2. Assay of ACAT Inhibitory Activity in the Macrophage Derived from Rat Peritoneal:

The rat peritoneal-derived macrophage was prepared according to the method disclosed in the literature: Biochimica et Biophysica Acta, 1126, 73–80, 1992. The ACAT activity was determined by a modified method of the method disclosed in the above literature: Biochimica et Biophysica Acta, 1126, 73–80, 1992, i.e., using radioactive [9,10-$^{3}$H] oleic acid and exogenous cholesterol contained in the liposome which was re-constituted according to the method disclosed in the literature: Biochimica et Biophysica Acta, 1213, 127–134, 1994, and calculated from the radioactivity of the labeled cholesterolyl oleate. The results are shown in Table 14.

TABLE 14

| Test compound (Example No.) | ACAT inhibitory activity IC$_{50}$ (nM) |
| --- | --- |
| 18 (hydrochloride) | 16 |

INDUSTRIAL APPLICABILITY

The pyridone derivative and the aminopyridone derivative can safely be prepared by the present invention. Besides, the pyridone derivative of the present invention and a salt thereof strongly inhibits ACAT activity in a specimen of rabbit liver or in rat peritoneal-derived macrophage. Therefore, the pyridone derivative of the present invention or a salt thereof is useful not only as an agent for treatment of hyperlipidemia, but also in the prophylaxis or therapeutic treatment of atherosclerosis per se or various diseases accompanied by atherosclerosis, for example, cerebral infarction, cerebral thrombosis, transient cerebral ischemia, angina pectoris, myocardial infarction, peripheral thrombus or occlusion.

What is claimed is:

1. A process for preparing an aminopyridone derivative of the formula (5):

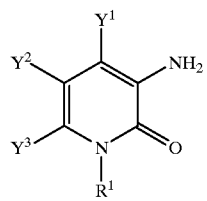

(5)

wherein $R^1$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group; $Y^1$ is a hydrogen atom, an alkyl group, a substituted alkyl group, a cycloalkyl group, a substituted cycloalkyl group, an aromatic group, or a substituted aromatic group; and $Y^2$ and $Y^3$ are independently a hydrogen atom, a halogen atom, a hydroxy group, a cyano group, a trifluoromethyl group, a nitro group, an amino group, a mono-lower alkylamino group, a di-lower alkylamino group, a lower alkoxy group, a lower alkylthio group, a lower alkylsulfinyl group, a lower aikylsulfonyl group, an alkyl group, a substituted alkyl group, a cycloalkyl group, a substituted cycloalkyl group, an aromatic group, a substituted aromatic group, or $Y^2$ and $Y^1$ may combine each other together with the carbon atoms to which they bond, and form a substituted or unsubstituted pyridine ring, which comprises heating a compound of the formula (8):

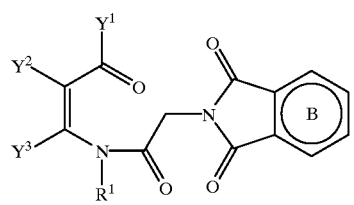

(8)

wherein $R^1$, $Y^1$, $Y^2$ and $Y^3$ are as defined above, and Ring B is a substituted or unsubstituted benzene ring, in the presence of a base, to give a compound of the formula (9):

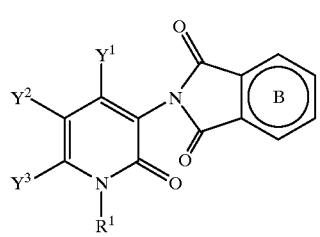

(9)

wherein $R^1$, $Y^1$, $Y^2$, $Y^3$ and Ring B are as defined above, followed by removing the protecting phthaloyl group thereof.

2. The process for preparing the aminopyridone derivative according to claim 1, wherein $Y^2$ and $Y^3$ combine each other together with the carbon atoms to which they bond, and form a substituted or unsubstituted pyridine ring, and said pyridine ring is a group of the following formula (a), (b) or (c):

a substituted or unsubstituted pyridine ring, and said pyridine ring is a group of the following formula (a):

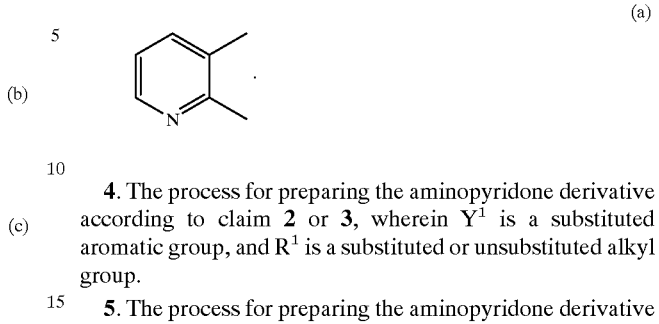

4. The process for preparing the aminopyridone derivative according to claim 2 or 3, wherein $Y^1$ is a substituted aromatic group, and $R^1$ is a substituted or unsubstituted alkyl group.

5. The process for preparing the aminopyridone derivative according to claim 4, wherein $Y^1$ is a 3-methoxyphenyl group, and $R^1$ is a butyl group.

* * * * *

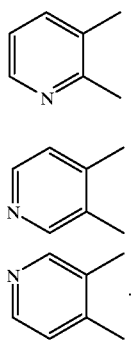

3. The process for preparing the aminopyridone derivative according to claim 1, wherein $Y^2$ and $Y^3$ combine each other together with the carbon atoms to which they bond, and form